(12) United States Patent
Kraus et al.

(10) Patent No.: US 9,978,159 B2
(45) Date of Patent: May 22, 2018

(54) METHOD AND APPARATUS FOR MOTION CORRECTION AND IMAGE ENHANCEMENT FOR OPTICAL COHERENCE TOMOGRAPHY

(71) Applicants: Friedrich-Alexander-Universitaet Erlangen-Nuernberg, Erlangen (DE); Massachusetts Institute of Technology, Cambridge, MA (US)

(72) Inventors: Martin F. G. Kraus, Cambridge, MA (US); Benjamin M. Potsaid, Cambridge, MA (US); James G. Fujimoto, Cambridge, MA (US); Markus Anton Mayer, Cambridge, MA (US); Ruediger Bock, Cambridge, MA (US); Joachim Hornegger, Cambridge, MA (US)

(73) Assignee: Friedrich-Alexander-Universitaet Erlangen-Nuernberg, Erlangen (DE)

( * ) Notice: Subject to any disclaimer, the term of this patent is extended or adjusted under 35 U.S.C. 154(b) by 0 days. days.

(21) Appl. No.: 14/980,466

(22) Filed: Dec. 28, 2015

(65) Prior Publication Data

US 2017/0140560 A1 May 18, 2017

Related U.S. Application Data

(63) Continuation of application No. 13/097,785, filed on Apr. 29, 2011, now Pat. No. 9,269,144.

(Continued)

(51) Int. Cl.
*G06T 7/30* (2017.01)
*G06T 11/00* (2006.01)
(Continued)

(52) U.S. Cl.
CPC .......... *G06T 11/006* (2013.01); *A61B 3/0025* (2013.01); *A61B 3/102* (2013.01);
(Continued)

(58) Field of Classification Search
None
See application file for complete search history.

(56) References Cited

U.S. PATENT DOCUMENTS 7,365,856 B2    4/2008  Everett et al.
8,004,517 B1 *  8/2011  Edelsbrunner .......... G06T 17/20
                                                      345/419
(Continued)

FOREIGN PATENT DOCUMENTS

EP         1 118 962 A1    7/2001
WO    WO 2006/077107 A1    7/2006
(Continued)

OTHER PUBLICATIONS

Zawadzki, R.J. et al., "Correction of motion artifacts and scanning beam distortions in 3D ophthalmic optical coherence tomography imaging," Progress in Biomedical Optics and Imaging, Proceedings of SPIE—Ophthalmic Technologies XVII 2007 SPIE US, vol. 6426, 2007, pp. 1-11.*

(Continued)

*Primary Examiner* — Said Broome
(74) *Attorney, Agent, or Firm* — Foley Hoag LLP

(57) ABSTRACT

Images of an object, such as OCT scans of a human eye, can include distortions and data gaps due to relative motion of the object and the image acquisition device. Methods and systems for correction of such distortions and data gaps are described herein. Motion-corrected data is arrived at by applying three-dimensional transforms to input three-dimensional data sets that represent at least partially overlapping regions of the imaged object. The three dimensional trans- (Continued)

forms are computed based on an objective function that accounts for similarity between the transformed three-dimensional data sets and the estimated motion of the object relative to an imaging instrument. Methods and systems described herein advantageously eliminate the need for postulated assumptions and reliance on landmarks and are capable of filling data gaps, thereby producing high quality, undistorted images of objects subject to movement during imaging. Multiple motion-corrected data sets can be merged or combined to produce a data set with improved image quality.

28 Claims, 37 Drawing Sheets

Related U.S. Application Data

(60) Provisional application No. 61/329,347, filed on Apr. 29, 2010.

(51) Int. Cl.
 | | | |
 |---|---|---|
 | *A61B 3/10* | (2006.01) | |
 | *A61B 3/00* | (2006.01) | |
 | *G06T 7/246* | (2017.01) | |

(52) U.S. Cl.
 CPC .............. *G06T 7/248* (2017.01); *G06T 7/30* (2017.01); *G06T 2207/10101* (2013.01)

(56) References Cited

U.S. PATENT DOCUMENTS

| | | | |
|---|---|---|---|
| 2005/0249398 A1* | 11/2005 | Khamene | G06T 7/38 382/154 |
| 2006/0034374 A1 | 2/2006 | Park et al. | |
| 2008/0021882 A1 | 1/2008 | Pu et al. | |
| 2009/0103049 A1 | 4/2009 | McLean et al. | |
| 2010/0166280 A1 | 7/2010 | Endo et al. | |

FOREIGN PATENT DOCUMENTS

| | | |
|---|---|---|
| WO | WO 2011/139895 | 11/2011 |
| WO | WO-2011/139895 A1 | 11/2011 |

OTHER PUBLICATIONS

Notification of Transmittal of the International Search Report and the Written Opinion of the International Searching Authority for Int'l Application No. PCT/US2011/034572; 13 pages, dated Sep. 14, 2011.

Kraus, M. et al., "Combination of Multiple Motion Corrected OCT Volume Scans for Noise Reduction and Extraction of Arbitrary Cross-Sectional Images," ARVO Abstract Only, 2 pages, Retrieved from the Internet on Feb. 16, 2010 from http://www.abstractsonline.com/submit/SubmitPrinterFriendlyVersion.as . . . .

Kraus, M. et al., "Motion Artifact Correction in OCT Volume Scans Using Image Registration," ARVO Abstract Only, 3 pages, Retrieved from the Internet on Apr. 12, 2009 from http://www.abstractonline.com/submit/SubmitPrint . . . .

Ricco, S. et al., "Correcting Motion Artifacts in Retinal Spectral Domain Optical Coherence Tomography via Image Registration," Sep. 20, 2009, Medical Image Computing and Computer-Assisted Intervention a Miccai 2009, Springer Berlin Heidelberg, Berlin, Heidelberg, pp. 100-107, XP019130304.

Tolliver, D.A. et al., Carnegie Mellon, UPMC Eye Center "An In-painting Method for Combining Multiple SD-OCT Scans With Applications in Z-Motion Recovery, Noise Reduction and Longitudinal Studies," Tuesday, May 5, 2009, 1 page.

Zawadzki, R.J. et al., "Correction of motion artifacts and scanning beam distortions in 3D ophthalmic optical coherence tomography imaging," Progress in Biomedical Optics and Imaging—Proceedings of SPIE—Ophthalmic Technologies XVII 2007 SPIE US, vol. 6426, 2007, XP000002657496.

Notification Concerning Transmittal of International Preliminary Report on Patentability and International Preliminary Report on Patentability for Int'l Application No. PCT/US2011/034572, "Method and Apparatus for Motion Correction and Image Enhancement for Optical Coherence Tomography," dated Nov. 8, 2012.

\* cited by examiner

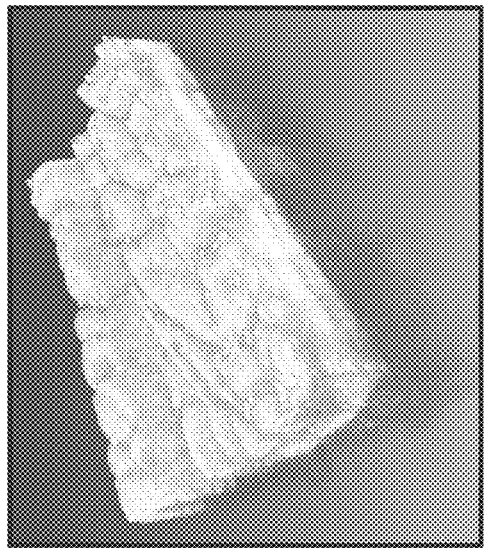
FIG. 3C
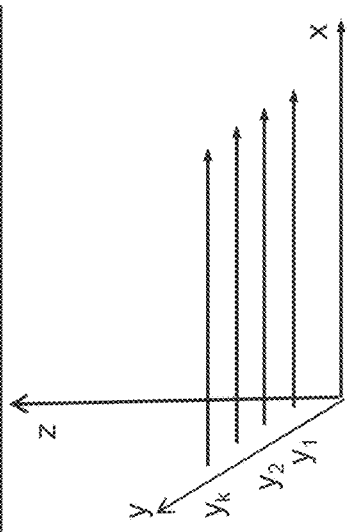
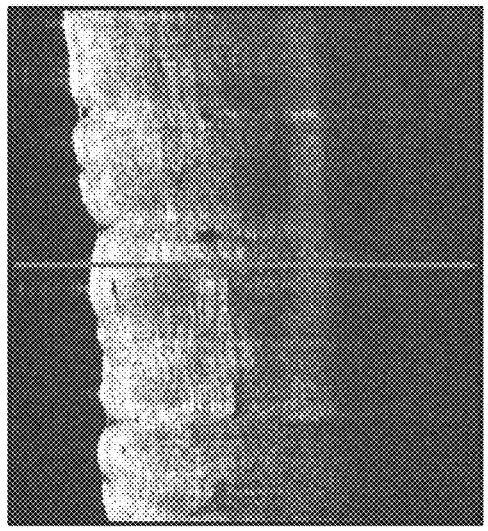
FIG. 3B
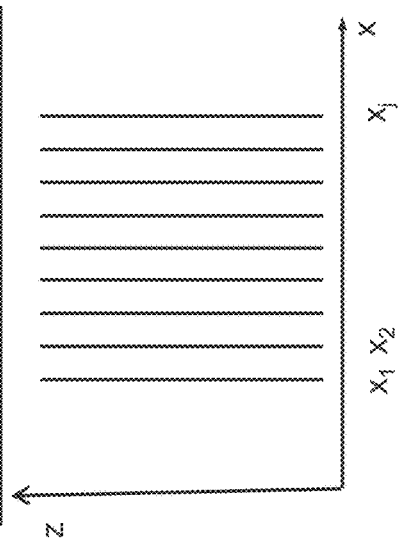
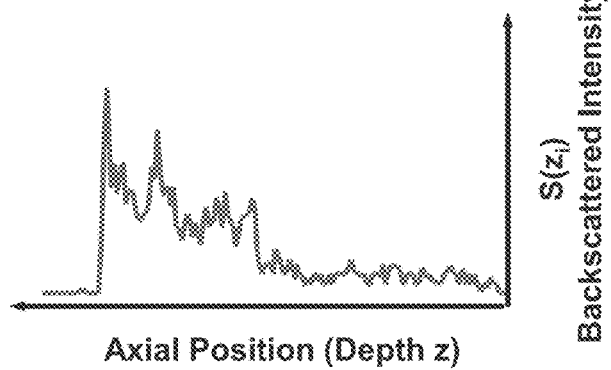
FIG. 3A

Motion artifacts

X (Fast Scan Direction)
Z (Depth) Direction

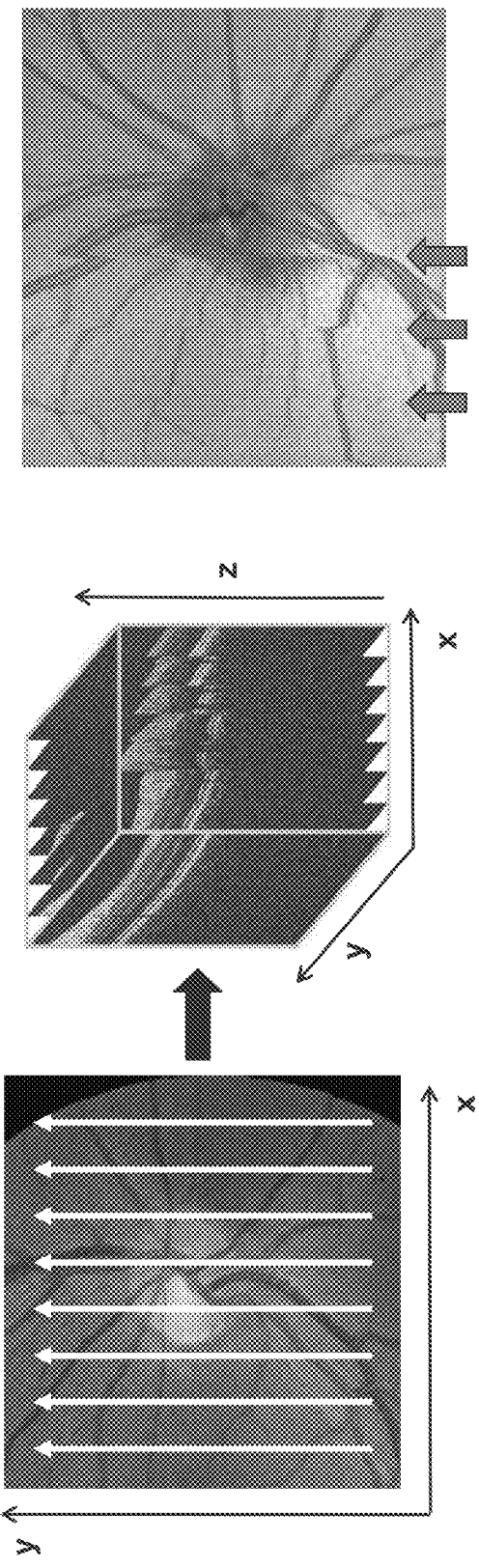

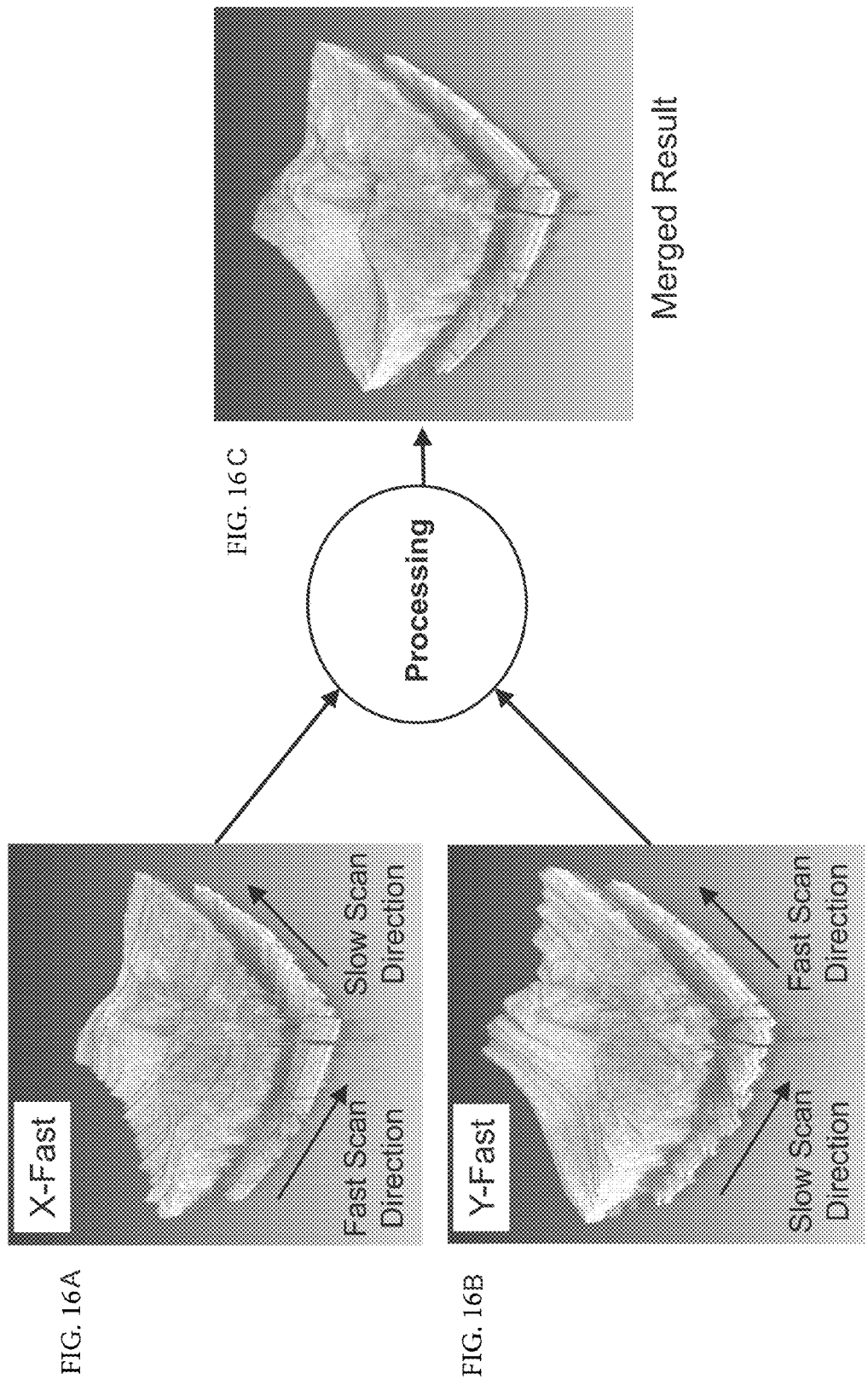

Merged result

Cross section from Vol 2

Cross section from Vol 1

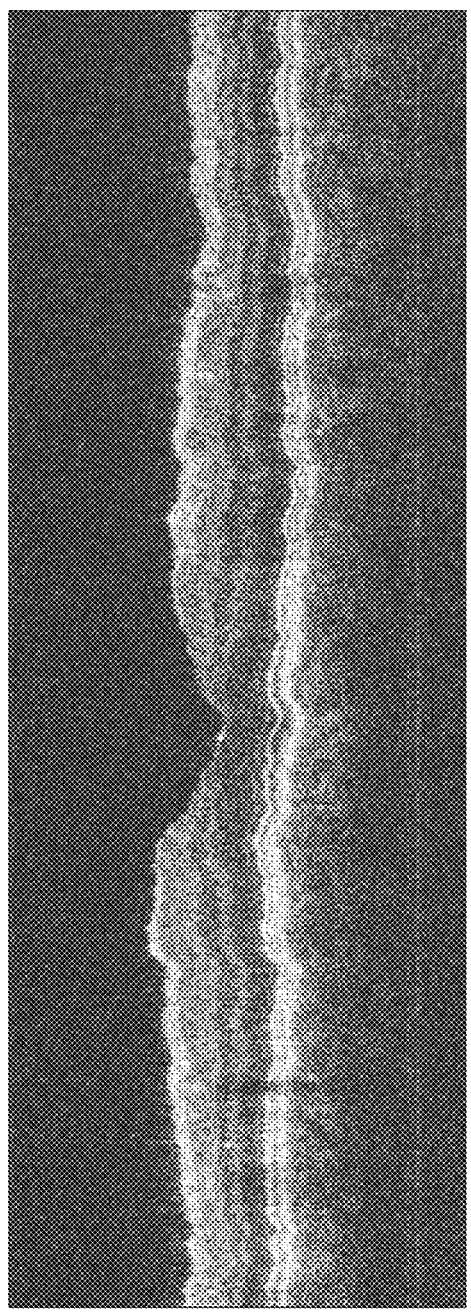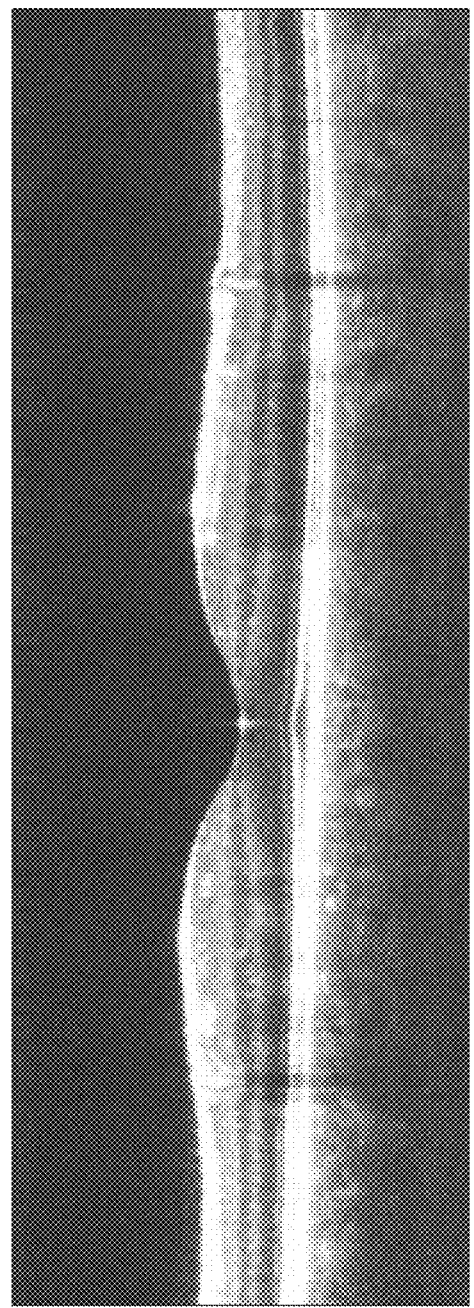
FIG. 22A
FIG. 22B

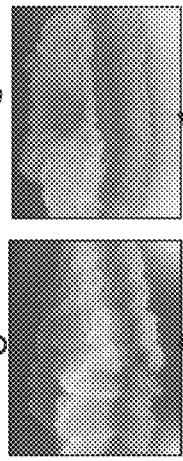
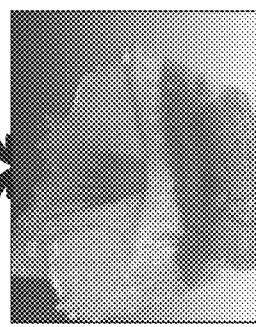
FIG. 24C
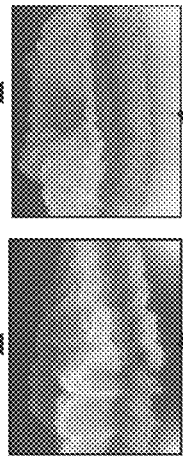
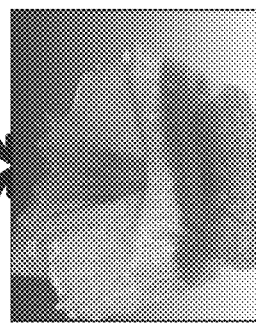
FIG. 24B
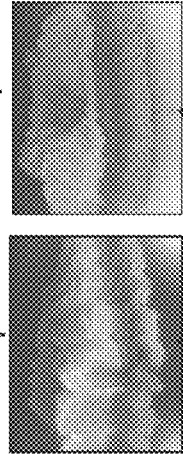
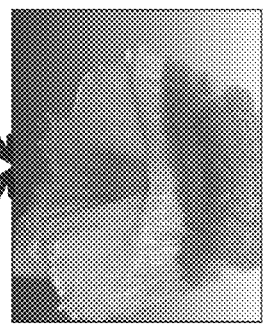
FIG. 24A Registered Merged1

Registered Merged2

Registered Merged3

Figure 29: Sequential sampling pattern

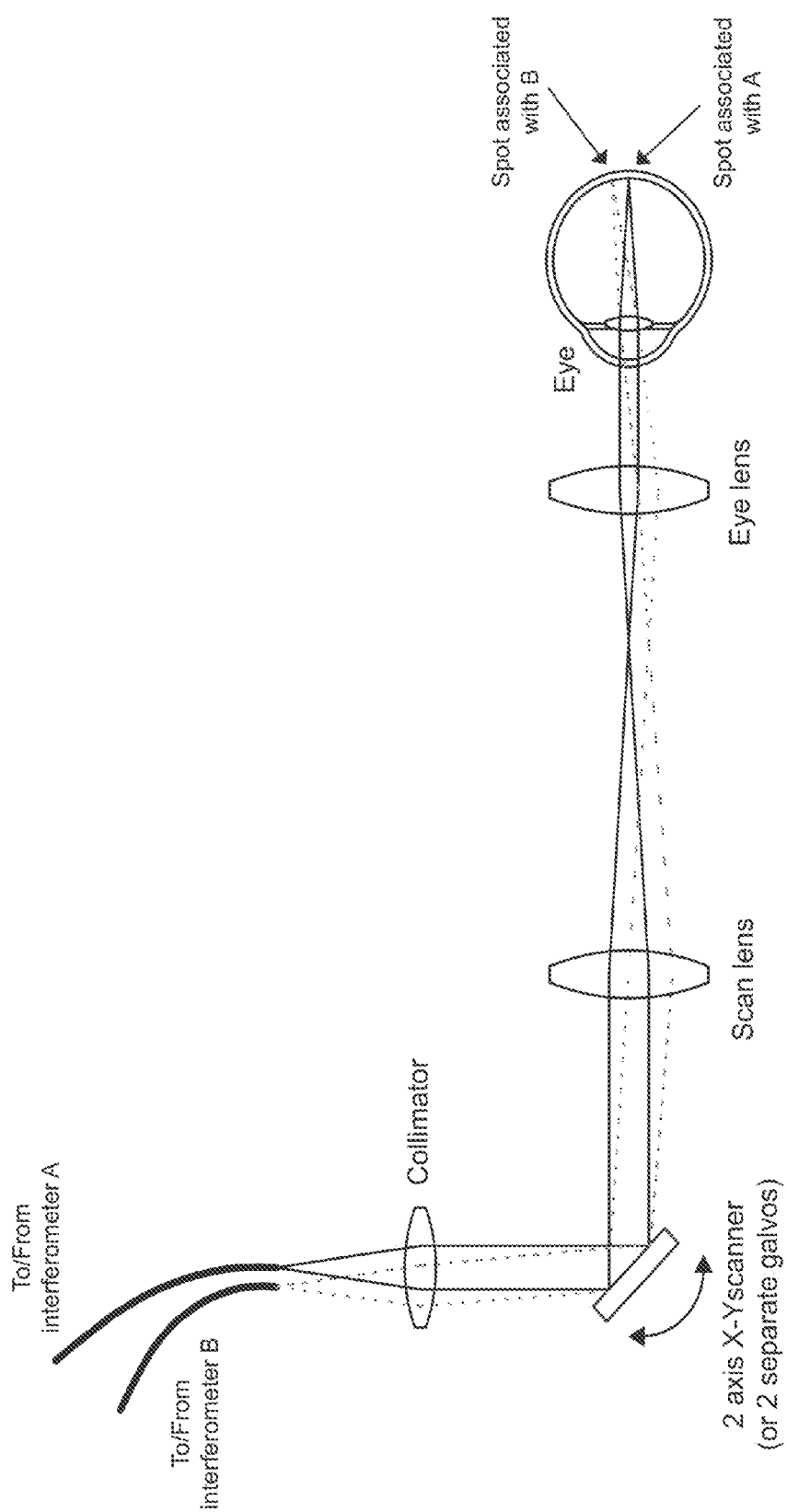

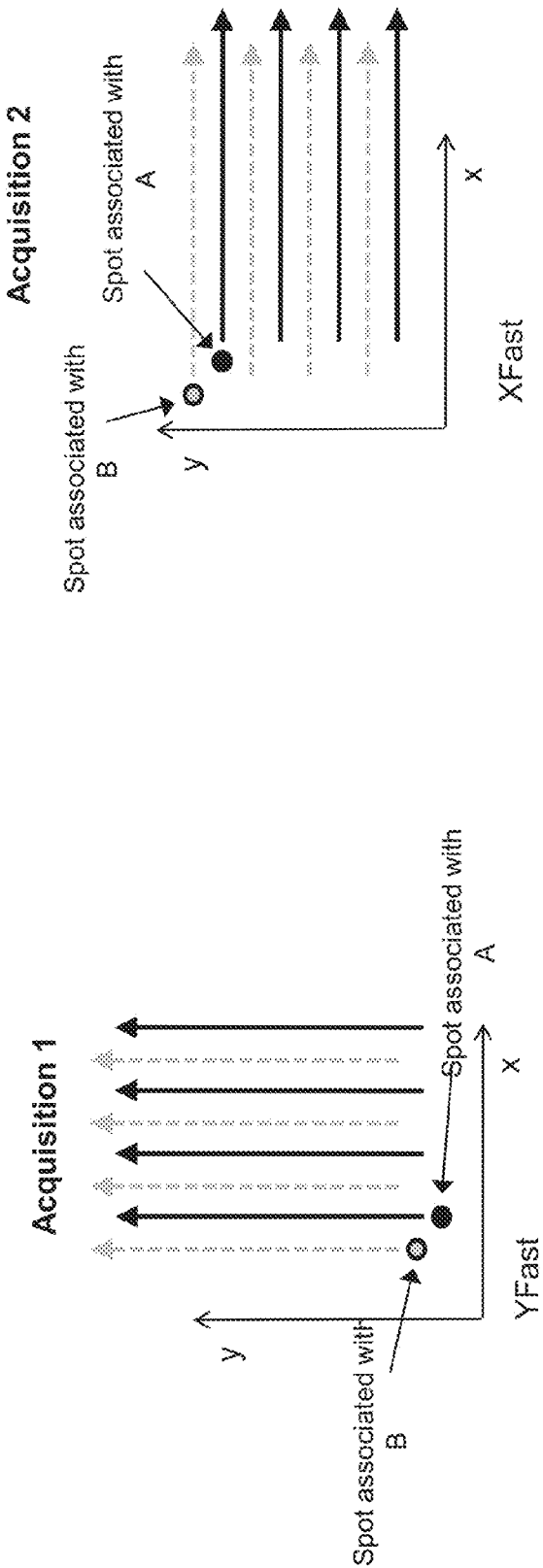

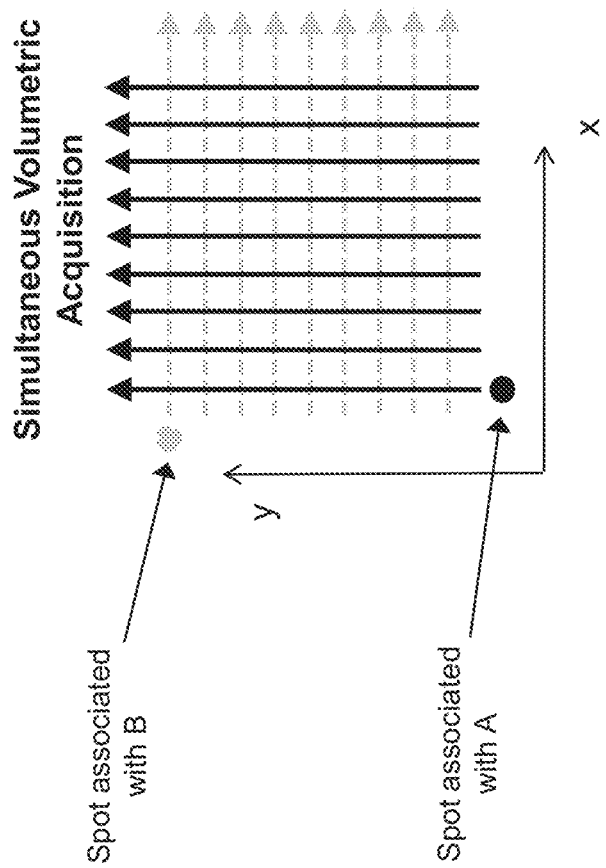

METHOD AND APPARATUS FOR MOTION CORRECTION AND IMAGE ENHANCEMENT FOR OPTICAL COHERENCE TOMOGRAPHY

RELATED APPLICATION

This application is a continuation of U.S. application Ser. No. 13/097,785, filed Apr. 29, 2011, which claims the benefit of U.S. Provisional Application No. 61/329,347, filed on Apr. 29, 2010. The entire teachings of the above application(s) are incorporated herein by reference.

GOVERNMENT SUPPORT

The invention was supported, in whole or in part, by grants R01-EY011289-24 and R01-CA075289-13 from the NIH and contracts FA9550-07-1-0101 and FA9550-07-1-0014 from the Air Force Office of Scientific Research. The Government has certain rights in the invention.

BACKGROUND

Optical coherence tomography (OCT) acquires cross-sectional images and volumetric data sets by measuring the echo time delay and magnitude of backscattered or back-reflected light from inside an object material or biological tissue (e.g., a human eye). Relative movement of the object and the data acquisition device give rise to the distortion and errors in the acquired image.

SUMMARY

One example embodiment of the present invention is a method of processing data sets. The method comprises computing, based on a value of an objective function, one or more three-dimensional transforms, each associated with a respective three-dimensional data set, said three-dimensional data sets representing at least partially overlapping regions of an object, wherein said computing includes evaluating the objective function. In this embodiment, the objective function is evaluated by (a) calculating similarity between (i) two or more three-dimensional data sets in a transformed state, or (ii) two or more preprocessed three-dimensional data sets in the transformed state, and (b) estimating motion of the object relative to an imaging instrument. The method further includes applying at least one three-dimensional transform to its respective three-dimensional data set or to a derivative three-dimensional data set corresponding to the respective three-dimensional data set to obtain at least one motion-corrected data set.

Another example embodiment of the present invention is a system for processing data sets, comprising a computing module configured to compute, based on a value of an objective function, one or more three-dimensional transforms, each associated with a respective three-dimensional data set, said three-dimensional data sets representing at least partially overlapping regions of an object, wherein said computing includes evaluating the objective function. In this embodiment, the objective function is evaluated by (a) calculating similarity between (i) two or more three-dimensional data sets in a transformed state, or (ii) two or more preprocessed three-dimensional data sets in the transformed state, and (b) estimating motion of the object relative to an imaging instrument. The system further includes a motion-correction module, configured to apply at least one three-dimensional transform to its respective three-dimensional data set corresponding to the respective three-dimensional data set or to a derivative three-dimensional data set to obtain at least one motion-corrected data set.

Another example embodiment of the present invention is a non-transitory computer-readable medium having thereon a sequence of instructions, which, when executed by a processor, cause the processor to compute, based on a value of an objective function, one or more three-dimensional transforms, each associated with a respective three-dimensional data set, said three-dimensional data sets representing at least partially overlapping regions of an object, wherein the instructions that cause the processor to compute the one or more three-dimensional transforms include instructions to cause the processor to evaluate the objective function. In this embodiment, the objective function is evaluated by (a) calculating similarity between (i) two or more three-dimensional data sets in the transformed state, or (ii) two or more preprocessed three-dimensional data sets in the transformed state, and (b) estimating motion of the object relative to an imaging instrument. The sequence of instructions, when executed by a processor, further cause the processor to apply at least one three-dimensional transform to the respective three-dimensional data set or to a derivative three-dimensional data set to obtain at least one motion-corrected data set.

Yet another example embodiment of the present invention is a method of processing OCT data sets, comprising acquiring two or more three-dimensional OCT data sets representing at least partially overlapping regions of an object, wherein at least one data set is acquired using a scan pattern complementary with respect to a scan pattern of at least one other data set, and computing a three-dimensional transform for each data set using an objective function. In this embodiment, the objective function (a) favors computed similarity between the three-dimensional data sets in the transformed state, and (b) penalizes motion of the object relative to an imaging instrument. The method further includes applying at least one three-dimensional transform to its respective data set to obtain at least one motion-corrected data set.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 3A through 3C are illustrations of one-dimensional (panel A), two-dimensional (panel B), and three-dimensional (panel C) Optical Coherence Tomography data sets.

FIG. 11A is a fundus photograph with arrows indicating the fast scanning direction superimposed.

FIG. 11B is a set of cross sectional images from a three-dimensional OCT data set of an optic nerve head of a human retina.

FIG. 11C is an OCT fundus image showing transverse motion effects.

FIGS. 16A through 16C are illustrations of 3D motion correction: panel A shows a first three dimensional data set with the fast raster scan in the x direction; panel B shows a second three dimensional data set with the fast raster scan in the y direction; panel C shows the merged motion-corrected image.

FIGS. 22A and 22B are illustrations of motion correction methods described herein: panel A is an OCT cross sectional image extracted from an uncorrected three dimensional data set; panel B is an OCT cross sectional image extracted from a three dimensional data set generated by registering and merging six overlapping three dimensional data sets.

FIGS. 24A through 24C are illustrations of acquiring and motion correcting and merging disjoint data sets of the same object to assess reproducibility between data sets. Panel A is set of volumetric renderings of a first pair of three dimensional data sets acquired with a fast scan in the X direction and a fast scan in the Y direction, and the three-dimensional rendering of the resulting first registered and merged three dimensional data set (bottom). Panel B is set of volumetric renderings of a second pair of three dimensional data sets acquired with a fast scan in the X direction and a fast scan in the Y direction, and the three-dimensional rendering of the resulting second registered and merged three dimensional data set (bottom). Panel C is set of volumetric renderings of a third pair of three dimensional data sets acquired with a fast scan in the X direction and a fast scan in the Y direction, and the three-dimensional rendering of the resulting third registered and merged three dimensional data set (bottom).

FIG. 34A is a schematic diagram of a two-spot scanning apparatus with coupled scan motion that can be used to practice the methods of the present invention.

FIG. 34B is an example two spot raster scan pattern with the fast scan in the y direction.

FIG. 34C is an example two spot raster scan pattern with the fast scan in the x direction.

FIG. 35B is an example scan pattern with two independently controlled spots that acquires two raster scanned data sets simultaneously with different fast scan directions.

DETAILED DESCRIPTION

Figure 1:
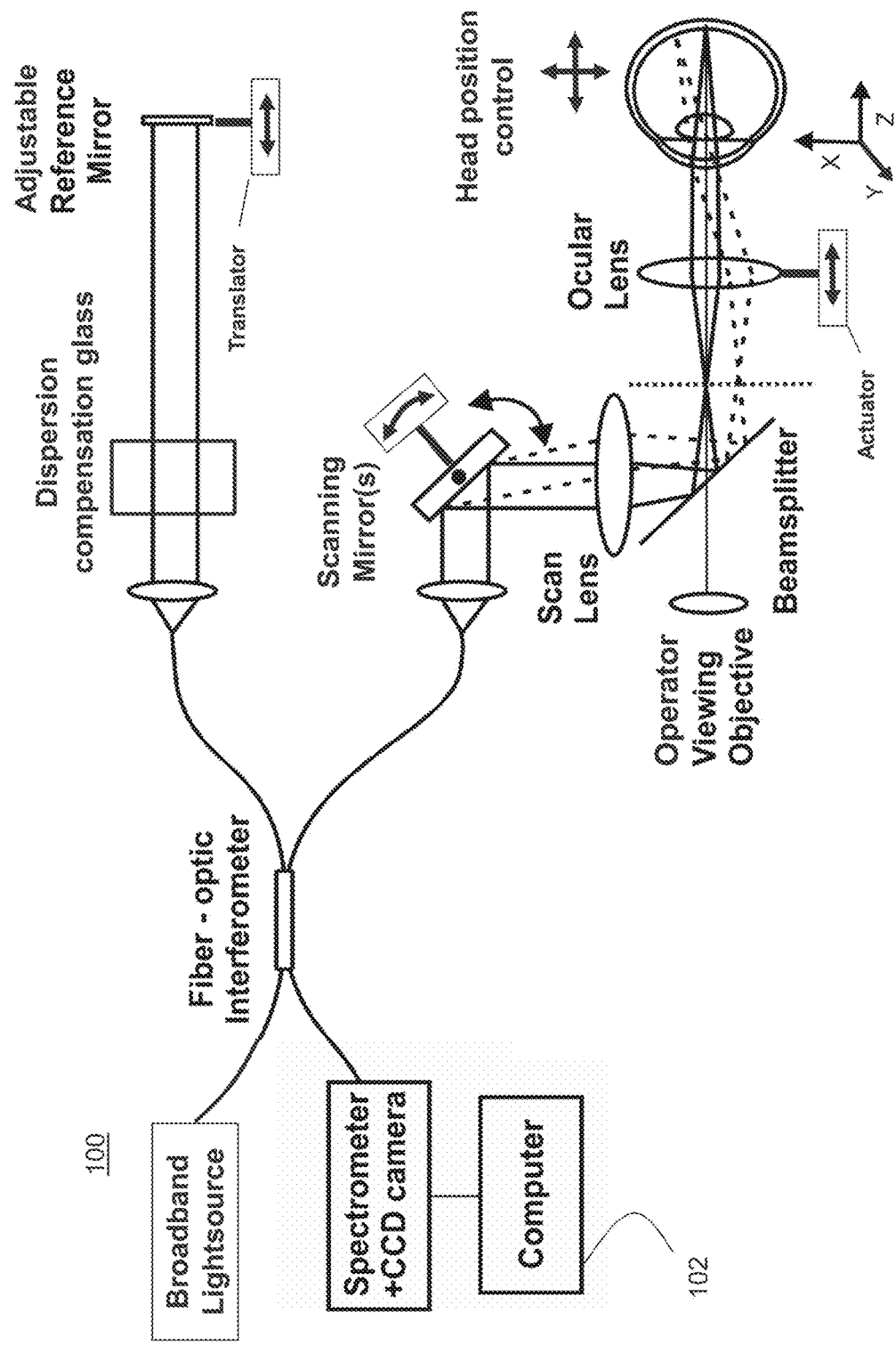
FIG. 1 is a schematic diagram of a spectral/Fourier domain ophthalmic OCT apparatus.
Figure 2:
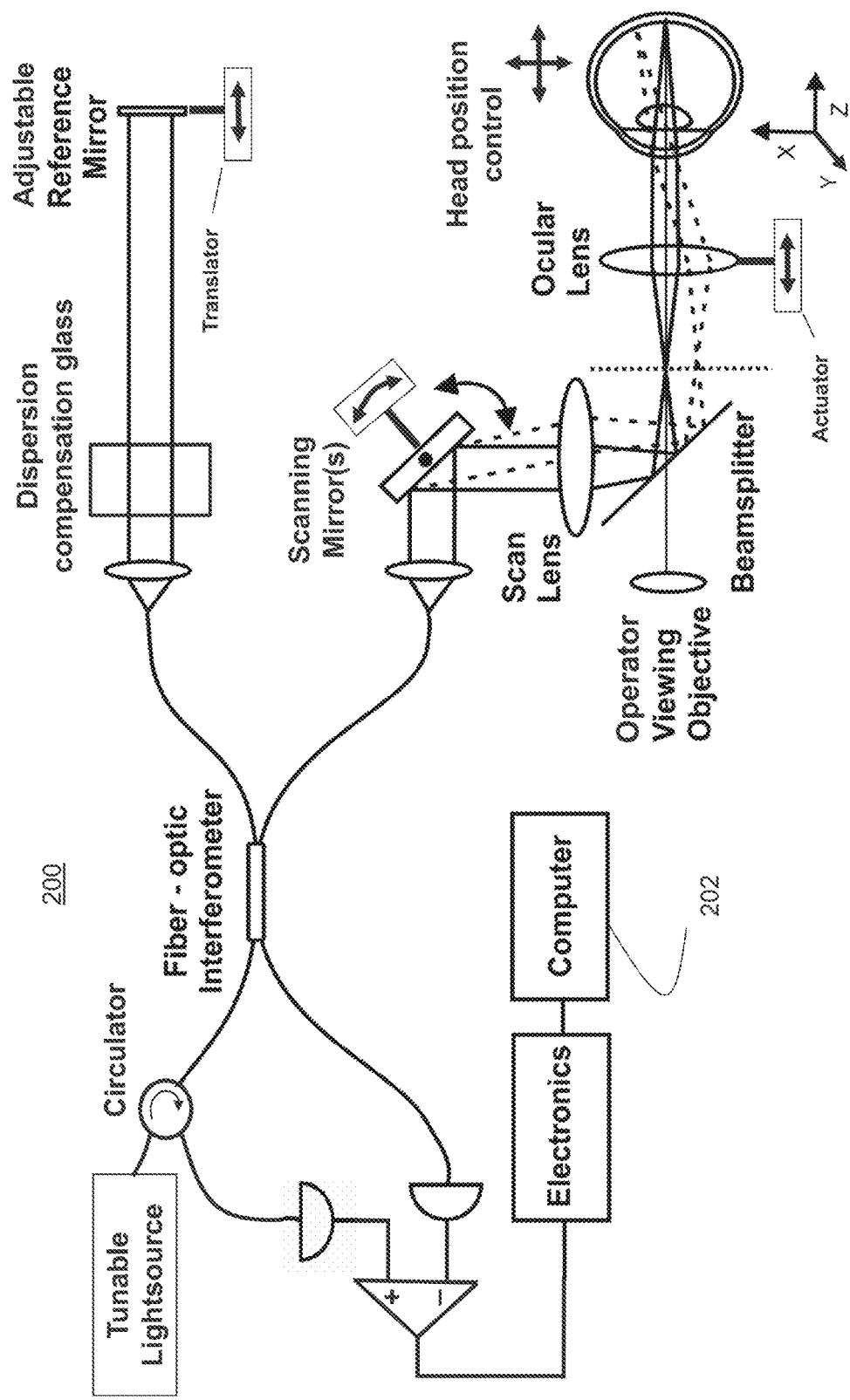
FIG. 2 is a schematic diagram of a swept source/Fourier domain ophthalmic OCT apparatus.

Optical coherence tomography (OCT) acquires cross-sectional images and volumetric data sets by measuring the echo time delay and magnitude of backscattered or back-reflected light from inside an object material or biological tissue. Examples of ophthalmic OCT imaging apparatus are shown in FIG. 1 and FIG. 2. Axial scan or A-scan information about structure versus depth can be measured by directing an optical beam on the object material or tissue and measuring the echo time delay of backscattered or back-reflected light. FIG. 3A shows an example of an axial scan signal. In FIG. 3A, the axial scan measures signal versus depth information in the z direction.

Cross-sectional images or B-scans can be generated by transverse scanning the optical beam across the object material or tissue and performing successive axial scan (A-scan) measurements. FIG. 3B shows an example of a two-dimensional OCT scan image with the beam scanned in the transverse x direction, with successive axial scan measurements performed at positions x1, x2, etc. This generates a two dimensional array which represents the backscattering or back-reflection in the x-z plane of the object material or tissue. This two dimensional information can be displayed as a false color or grey scale image.

Figure 4:
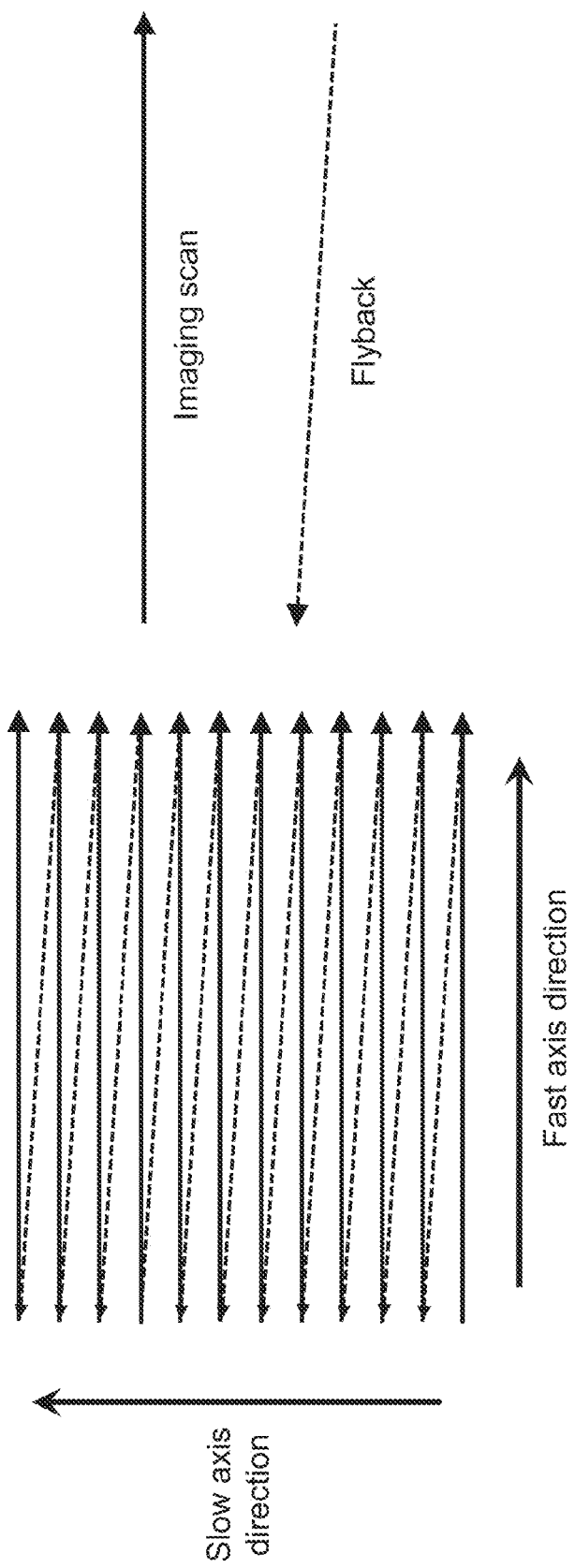
FIG. 4 is an illustration of a raster scan pattern.
Figures 5A, 5B, 5C:
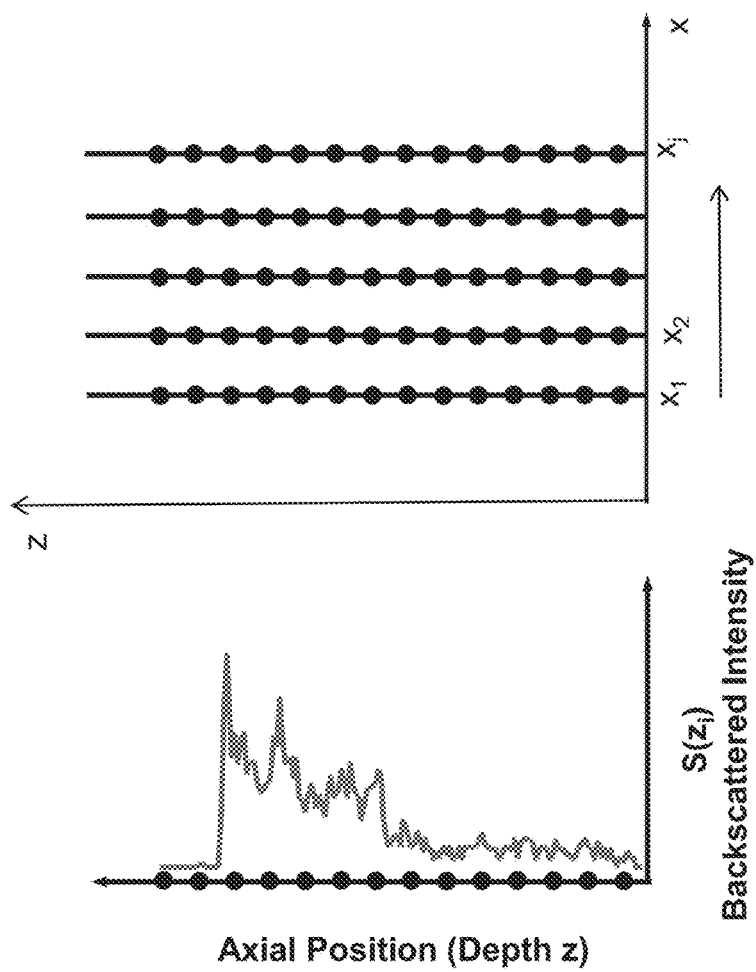
FIGS. 5A through 5C are illustrations of one-dimensional (panel A), two-dimensional (panel B), and three-dimensional (panel C) Optical Coherence Tomography data sets.

Volumetric (i.e. three-dimensional) 3D-OCT or three-dimensional OCT datasets can be generated by performing successive transverse B-scans in different transverse planes using for example a raster type scan pattern. FIG. 3C shows an example of a 3D-OCT volumetric data set generated from a sequence of transverse scans along the x direction (B-scans) performed at different positions displaced in the y direction y1, y2, etc. The example shows a three-dimensional data set acquired by a series of transverse scans in a raster scan pattern. FIG. 4 is an illustration of a typical scan pattern having a slow direction and a fast direction. However, it is recognized that there are many other scan patterns and ways to acquire 3D-OCT volumetric data. In general, a three-dimensional OCT dataset is generated by sweeping a beam of light over an object while recording A-Scan data. The beam is swept according to a trajectory as defined by a scan pattern. The scan pattern positions the beam at positions on the imaged object at points in time from which A-Scan data is recorded successively. It is generally the case that the OCT data sets are composed of individual pixels or voxels in a 1D, 2D, or 3D data set, as shown in FIGS. 5A through 5C. FIG. 5A is a plot of backscatter intensity as a function of axial position and represents a one-dimensional axial data along z direction. FIG. 5B is a schematic representation of a two-dimensional data set having an axial (Z) and a transverse (X) directions, in which each array at position $x_i$ represents one A-scan. FIG. 5C is a schematic representation of a three-dimensional data set having an axial (Z) and two transverse directions (X and Y). The elements of three-dimensional data set are traditionally referred to as voxels.

Additionally, one of ordinary skill in the art of OCT will appreciate that, in general, an OCT dataset can contain multiple data channels, such as amplitude, intensity, phase, polarization, spectroscopic information, and Doppler shift, among others. A three-dimensional dataset associates data values from these data channels with positions in a three-dimensional OCT device or instrument coordinate system.

OCT Embodiments

OCT can be performed using different embodiments including 1) an interferometer with a broadband light source and scanning optical reference delay line (known as time domain detection), 2) an interferometer with a broadband light source and a spectrometer for signal detection (known as Fourier/spectral domain OCT, spectral radar, or by other names) or 3) an interferometer with a frequency swept light source (known as swept source/Fourier domain OCT, optical frequency domain imaging, or by other names). FIG. 1 shows an example spectral/Fourier domain OCT imaging apparatus 100, that includes computer 102. FIG. 2 shows an example swept source/Fourier domain imaging apparatus 200 that includes computer 202. The Fourier domain detection embodiments have the advantage of very rapid acquisition speeds and are preferred for 3D-OCT volumetric imaging.

Effects of Motion in OCT Imaging

Figure 6A:
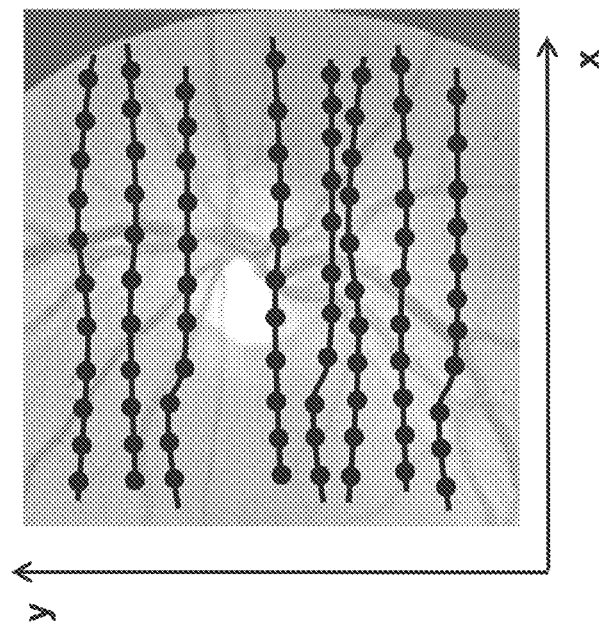
FIGS. 6A and 6B are illustrations of sampling distortions during image acquisition: panel A shows scanner coordinates, and panel B shows corresponding object sampling locations superimposed on the fundus photo of a human eye.
Figure 6B:
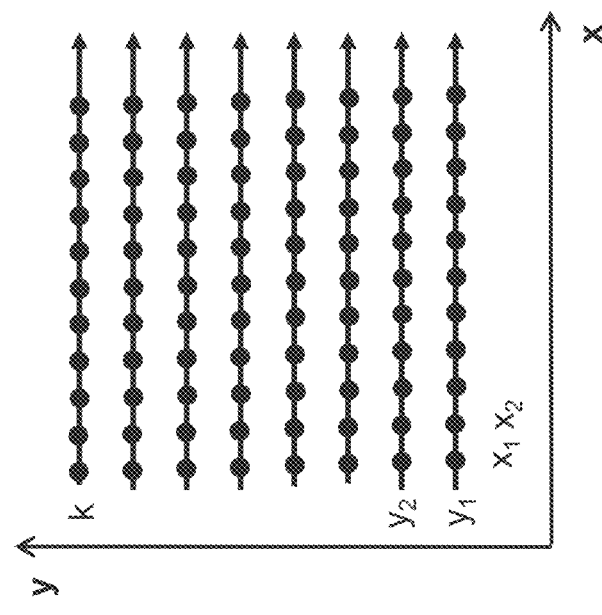

Since a 3D-OCT image or volumetric dataset is not acquired at a single point of time, but is composed of successive acquisitions of multiple A-scans performed in a transverse scanning pattern, where each A-scan is acquired sequentially at a different time, relative motion between the OCT scanning device and the object can occur during a single or in between multiple consecutive acquisitions. FIG. 6A and FIG. 6B show an example of OCT imaging of the retina of the eye in which the OCT scan pattern (FIG. 6A) is affected by eye motion (FIG. 6B). FIG. 6A shows a two-dimensional subset of a three-dimensional data set (an XY-plane having a fixed value of z), having superimposed on it the schematic representation of the points from which the data was acquired by a scanner in the scanner coordinates. FIG. 6B is OCT image of a human retina having superimposed on it a schematic representation of the points at which the data was acquired by the scanner in the object coordinates. As can be seen, motion causes the OCT beam position on the object being imaged to differ from the desired beam position determined by the OCT scanning device. This motion affects the transverse position of the beam in the x-y plane. In addition, motion can also occur in the axial or z direction. OCT imaging in the human eye, ophthalmic OCT, is a major clinical application of OCT technology. In ophthalmic OCT, axial motion can occur as the result of heartbeat which causes fluctuations in intraocular pressure. Transverse motion can result from eye tremor, drift or saccades (rapid motions) from changes in the patient's direction of gaze. Motion can also occur in the X, Y, and Z directions because of head or body motion of the subject (patient) taking place during acquisition.

Figure 7D:
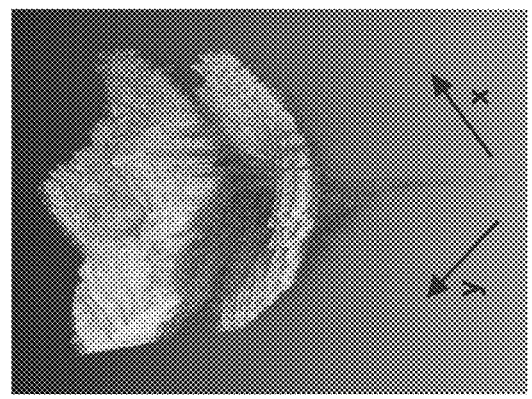
FIG. 7D is a rendering of three-dimensional OCT data set of an optic nerve head of a human retina.
Figure 7C:
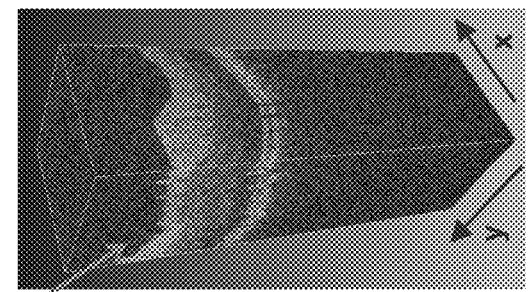
FIG. 7C is a rendering of a three-dimensional OCT data set of an optic nerve head of a human retina showing volumetric rendering.
Figure 7B:
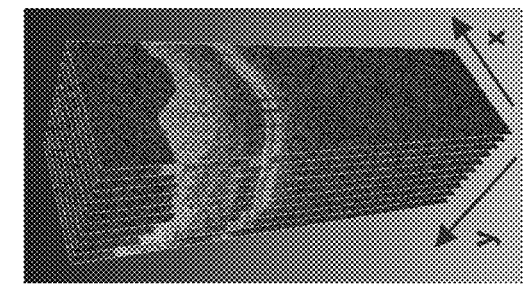
FIG. 7B is a set of cross sectional images from a three-dimensional OCT data set of an optic nerve head of a human retina showing individual cross-sectional images.
Figure 7A:
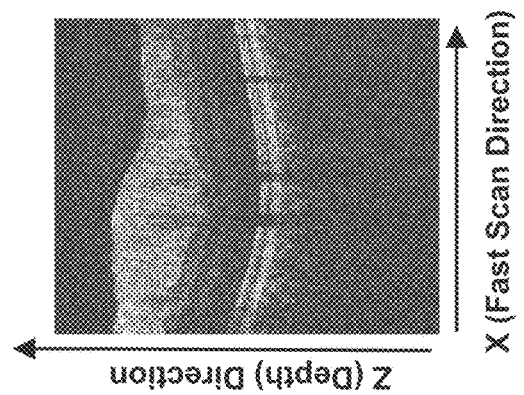
FIG. 7A is a cross-sectional image of a three-dimensional OCT data set of an optic nerve head in a human retina.

FIG. 7A through FIG. 7D show the effects of axial eye motion which is seen as distortion of topography in the 3D-OCT volumetric data set. FIG. 7A is showing a single cross section along the x-direction as acquired by an OCT device. FIG. 7B is showing how a three dimensional XFAST dataset can be constructed from multiple of these x-direction cross-sections. FIG. 7C is showing a view of the outer planes of the dataset cube. This view shows that there is axial motion visible along the y direction. FIG. 7D is a 3D rendering of said dataset.

The example illustrated in FIG. 7A through FIG. 7D shows a volumetric OCT data set acquired by rapid scanning in the x direction, using the scan pattern shown in FIG. 6A and FIG. 6B. Cross-sectional images may be extracted from the 3D-OCT volumetric data set. A cross-sectional image which is extracted along the x direction, corresponding to the direction of fast scanning, has minimal motion artifacts and more accurately represents the retinal structure and topography. In contrast, a cross-sectional image which is extracted along the y direction has significant motion artifacts in the axial direction. The wavy appearance of the retinal image does not represent the true contour of the retina, but is a distortion artifact of axial motion. This occurs because axial scans along the y direction are acquired with greater time separation than in the x direction when this scan pattern is used. In this example, the x direction is along the direction of the raster scan that has lower time difference between adjacent A-Scans. This direction is called the fast direction or fast axis. The y direction is perpendicular and is also referred to as the slow direction because the time difference between adjacent A-Scans is higher. In general, axial motion compromises the integrity of 3D-OCT volumetric data sets by distorting topography and producing distortion in any cross-sectional OCT images which are extracted from the volumetric data set along a direction where the axial scans are separated in time.

Figures 8A, 8B:
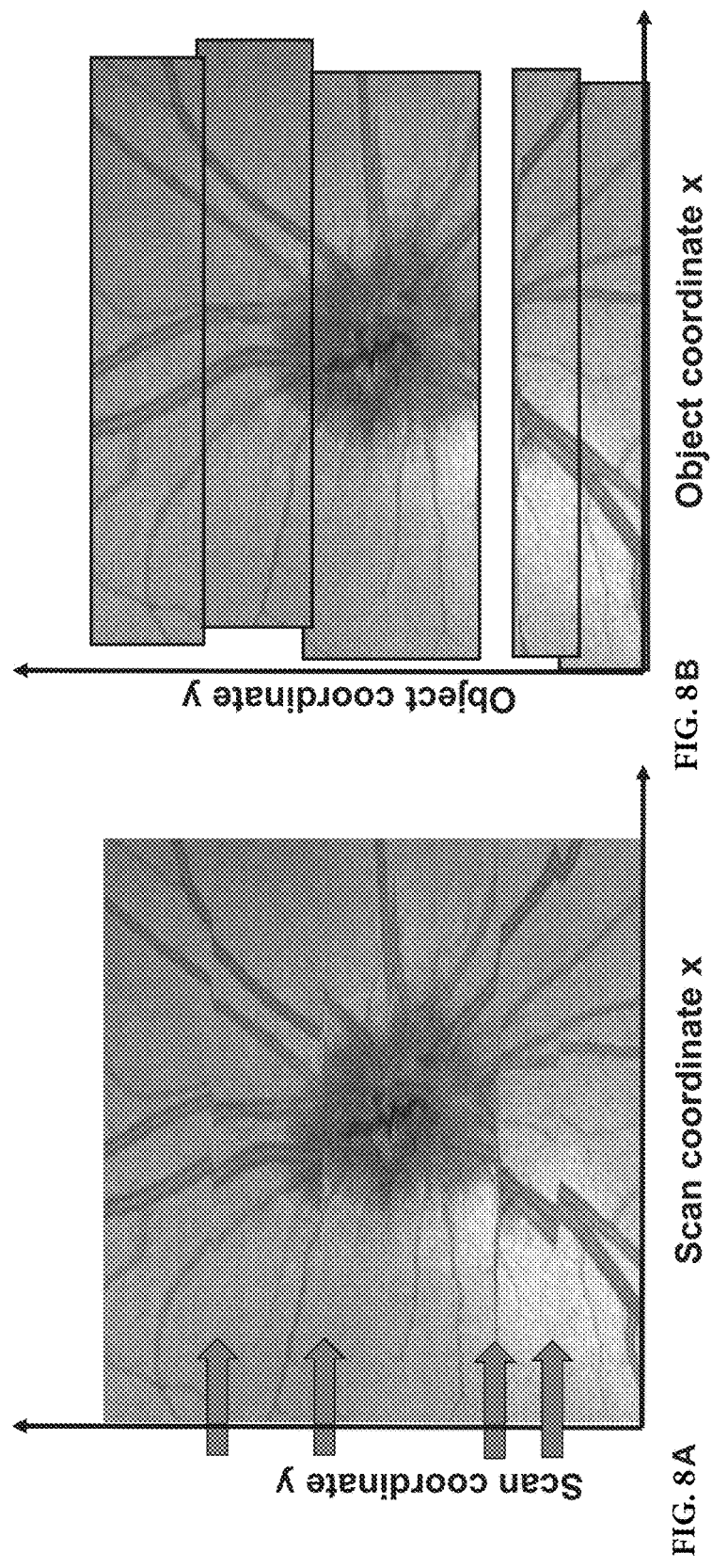
FIGS. 8A and 8B are illustrations of effects of transverse motion during image acquisition: panel A shows the distorted OCT fundus image in scanner coordinates; panel B shows superimposed images of overlapping regions in object coordinates.

Along with axial motion, transverse motion generally occurs during data acquisition. FIG. 8A and FIG. 8B show the effects of transverse motion. FIG. 8A is an image of a human eye obtained by axially summing the pixels (summing along the A-scan) in the 3D-OCT volumetric data set. This image is called an en face image, an OCT fundus image, or summed voxel projection. The process of summing the OCT intensity signal in the axial direction essentially collects all of the backscattered or back-reflected light and generates an image which is analogous to a photograph of the retina. The en face image in FIG. 8A shows the effects of rapid transverse eye motion, known as saccades, where the subject changed the direction of gaze. These rapid transverse motions are evident as discontinuities in the en face OCT fundus image as indicated by the arrows in FIG. 8A. This occurs because there is a difference in the expected transverse position of the OCT beam as determined by the OCT instrument scanning coordinate system, versus the real position of the retina determined by the object or retina coordinate system. This effect is shown in FIG. 8B where portions of the en face OCT fundus image obtained from the 3D-OCT volumetric data set have been registered to the real positions on the retina in the object or retinal coordinate system. Rapid transverse eye motion produced by saccades can cause the OCT beam to scan overlapping regions of the retina; or can cause the OCT beam to miss some regions of the retina, resulting in unscanned regions, or gaps in the dataset.

While this example shows the effects of rapid discontinuous movement of the eye, it is understood that there can also be smaller, slow and continuous movement such as tremor or drift. These will produce distortion of the OCT volumetric data set and corresponding en face OCT fundus images. This distortion can also occur in the axial as well as transverse direction. Relative motion between the OCT instrument and object being imaged can occur in a wide range of applications such as OCT microscopy in surgery, internal body OCT imaging, imaging of living specimens, or in using hand held OCT imaging instruments.

Relative motion between the OCT instrument and object material or tissue being imaged can therefore compromise the integrity of OCT images or 3D-OCT volumetric data sets, so that they do not accurately represent the true structure of the object material or tissue being imaged. This can reduce the reproducibility of quantitative measurements of structure or morphometry as well as functional measurements such as blood flow measurements using OCT doppler methods. Motion artifacts can also compromise the ability to accurately perform repeated imaging measurements over different time points and compare data obtained over time. The ability to perform accurate imaging measurements over time is important for many clinical applications of OCT which involve diagnosis or tracking disease progression.

Existing Techniques for Motion Correction in OCT Imaging

To compensate for motion distortion, some established OCT instruments employ active tracking hardware. These instruments have a separate tracking hardware subsystem that measures the position of the object tissue being imaged and modifies the scanning pattern of the OCT beam such that the desired position on the object tissue is scanned, even in the presence of object motion. However tracking hardware adds additional cost and complexity to an OCT system. In addition, under certain circumstances, the image acquisition times using tracking hardware can be much longer than without.

Other approaches for motion correction are software based and depend upon comparison of the 3D-OCT volumetric dataset to a motion free reference image, such as a photograph of the object or tissue being imaging. In ophthalmology, the photograph is referred to as a fundus photograph of the retina and is a standard ophthalmic diagnostic. Since the photograph is acquired at a single point in time and produces an en face image of the object tissue, it accurately represents the transverse features of the tissue. However, software which corrects for motion in a 3D-OCT volumetric dataset using a motion free reference image is limited to using 2D image information in the reference image, rather than 3D information. This limits the accuracy of the motion correction. Also, these techniques alone cannot correct for axial motion in the 3D-OCT volumetric dataset. Therefore, a need exists for improved methods of motion correcting 3D OCT data. Methods that do not require additional instrument hardware and that effectively correct for both axial and lateral motion are desirable. However, it is possible to use additional sources of information in certain embodiments. For example, it is possible to provide an initial estimate of motion in order to reduce the computation time for motion correction and registration.

Described herein are methods and apparatus to compensate motion artifacts occurring during optical coherence tomography (OCT) scanning. Example embodiments provide accurate and reproducible registration of motion corrupted OCT volumetric datasets, producing datasets without motion artifacts and which accurately represent the true structure of the object being imaged. Example methods do not require the use of a motion-free, reference image. Multiple motion corrected volumetric datasets can be merged to obtain a volumetric dataset having improved quality and signal-to-noise ratio compared to an individual volumetric dataset. Embodiments compensate for missing data from motion during acquisition and allow the acquisition of large datasets and longer acquisition times than possible without motion correction and merging.

Described herein are methods and apparatus which can correct for motion distortion in 3D-OCT volumetric datasets due to relative motion between the instrument and the object material or tissue. Example embodiments can also register and combine or merge multiple 2D and 3D OCT datasets to generate datasets which have improved image quality and completeness. Example methods work by first acquiring multiple 2D and 3D-OCT volumetric datasets using complementary scanning patterns in a subset of the acquisitions. At least one of the acquired datasets should be a 3D-OCT volumetric dataset. Each of the datasets acquired can have motion artifacts. Different complementary scan patterns are used which are designed to more accurately measure features of the object material or tissue by rapidly scanning along different directions or trajectories. The example methods include registering the multiple 2D and 3D-OCT datasets with respect to each other by transforming the data sets so that they favor similarity between registered datasets, while placing a penalty on the motion as it is implied by the registration transforms. The resulting registered 3D-OCT volumetric datasets are corrected for motion and accurately represent the true structure of the object tissue being imaged.

Furthermore, example embodiments can combine or merge multiple, registered OCT datasets to create enhanced quality datasets. The combined or merged dataset has improved signal to noise, reduced speckle noise and improved continuity of structural features. These improvements in dataset image quality enable improved segmentation or automatic measurement of structural features in applications which require quantitative assessment.

As noted previously, motion of the object tissue during scanned dataset acquisition can result in gaps (FIG. 8A and FIG. 8B) due to unscanned regions of the object. Example methods of registering and combining or merging different datasets enables substantially complete datasets to be created, even when individual acquired datasets are missing data. It should be noted that merging of the motion corrected data is not required. Motion corrected, but not merged, datasets can be generated using the methods described herein to achieve improved accuracy in the topological, structural, functional and morphological information of the data.

In many applications, the size of 3D-OCT volumetric datasets, as well as the image acquisition time, is limited by relative motion of the object to the OCT scanner. The source of this relative motion can either be motion of the scanned object, motion of the OCT device itself as can be the case when the instrument is not stable or for handheld OCT devices, or any combination of the preceding sources of motion. The motion can cause image distortion as well as incomplete datasets from unscanned regions of the object. For example, in ophthalmology, dataset acquisition times are typically limited to a few seconds due to patient eye motion and blinking. Embodiments enable the motion correction and registration of volumetric datasets as well as the generation of a substantially complete dataset from multiple dataset acquisitions. These features enable the acquisition of very large data sets as well as significantly increase the imaging time for which usable data can be obtained.

Many clinical applications require quantitative measurement of features in 3D-OCT volumetric datasets. In ophthalmology, quantitative measurement of the retinal nerve fiber layer thickness, retinal thickness or ganglion cell layer thickness is useful as a diagnostic for glaucoma, glaucomatous disease progression or response to treatment. Quantitative measurement of other features such as lesion structure and size, including lesions such as drusen, subretinal fluid or choroidal neovascular membranes are important indicators for age related macular degeneration.

The accuracy and reproducibility of quantitative measurement is limited by the accuracy and quality of 3D-OCT volumetric datasets. The accuracy with which the 3D-OCT volumetric datasets represents the true structure of the object tissue is important since distortion of the volumetric dataset with respect to true structure means that quantitative measurements are performed in the wrong location. Furthermore, motion and resulting distortion will be different in different volumetric datasets, decreasing the reproducibility of quantitative measurements. By enabling motion correction and accurate volumetric imaging of true tissue structure, and by enabling the acquisition of complete datasets in the presence of motion, example embodiments enable improved accuracy and reproducibility of quantitative measurement. In addition, by improving the image quality, the performance and accuracy of quantitative measurement is further improved.

Many clinical applications require imaging at multiple points in time, such as at different examinations at different times followed by quantitative comparison of volumetric dataset information across these different time points. These applications include the tracking of disease progression and response to therapy. In addition, imaging in small animal models is an important approach for pharmaceutical development and drug discovery. The ability to more accurately track small changes over time can improve the efficiency of these studies by reducing the number of animals required or decreasing the time required for the study by enabling smaller changes to be accurately measured with improved statistical significance. Example embodiments enable 3D-OCT volumetric datasets acquired at different time points to be registered with respect to each other. The registration of volumetric data at different time points enables accurate comparison of the volumetric datasets and accurate quantitative measurement of changes between the datasets. In this application, it should be noted that the datasets from different time points can be registered both with respect to true tissue structure, but also with respect to each other. However, the datasets from different time points are not necessarily merged or combined, but rather are used as inputs to quantitative measurement techniques which measure changes. These changes are indicative of disease progression or response to therapy.

Example embodiments include methods and apparatus to compensate motion artifacts occurring in optical coherence tomography (OCT) acquisitions due to object or instrument movement during the acquisition process. Example embodiments also include methods and apparatus to merge data from multiple volume scans. The example embodiments are described in the context of ophthalmic OCT imaging, but it is recognized that they may be used for other applications.

In general, scanning imaging devices, such as OCT, do not acquire the data all at once. Instead, data is acquired by successively sampling the object or target, acquiring sequential axial scans or A-scans at different times. In the case of in vivo scanning of a human eye or retina, eye motion relative to the instrument is common during the acquisition. Due to this motion, object regions are not uniformly sampled (FIG. 6A and FIG. 6B). The result is that motion artifacts affect the structure (FIG. 7A through 7D) and integrity of acquired data (FIG. 8A and FIG. 8B).

Embodiments are able to (i) compensate for these motion artifacts using two or more motion distorted acquisitions of the approximately same object region, but of varying sampling or scan pattern, (ii) merge the corrected data to gain data of enhanced data quality and morphological accuracy.

Figure 9:
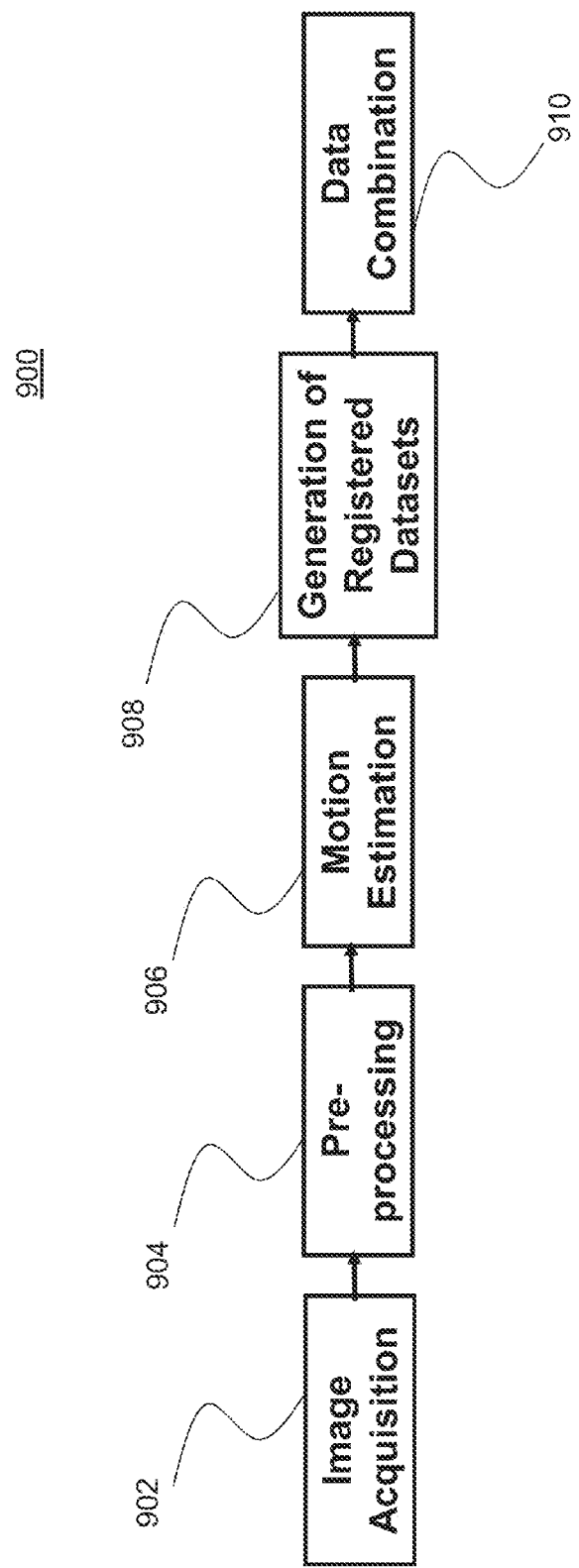
FIG. 9 is a flowchart illustrating an example embodiment of a method described herein.

FIG. 9 is a flow chart illustrating an example embodiment of a method 900 of the present invention. Method 900 can be executed by, for example, computer 102 of device 100 shown in FIG. 1 or computer 202 of device 200 shown in FIG. 2.

Method 900 includes at least the following operations:
902: Image acquisition;
904: Data preprocessing;
906: Motion estimation;
908: Generation of registered (motion corrected) datasets; and
910: Data combination (merging).

Figure 12:
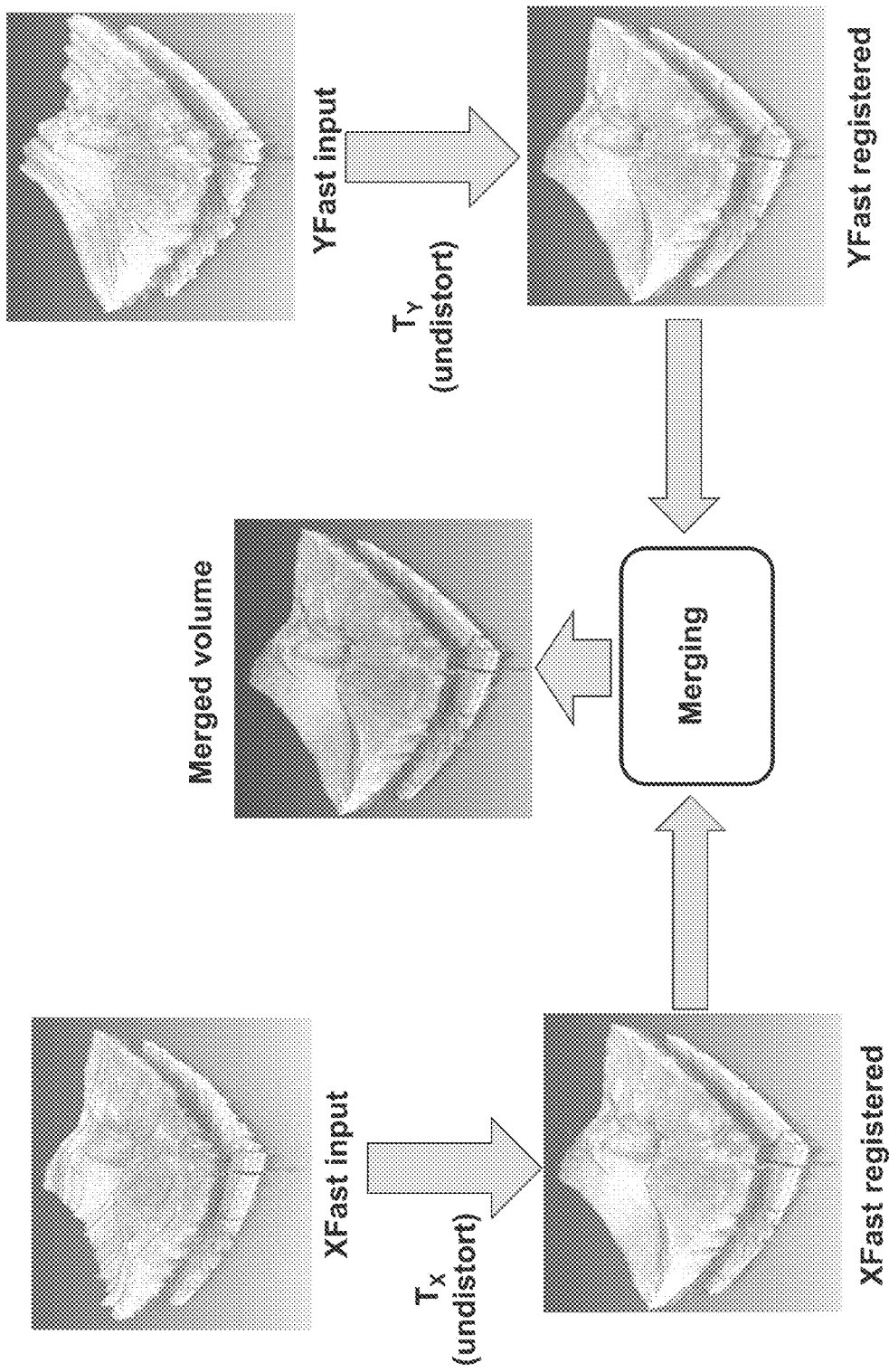
FIG. 12 illustrates a registration and merging principle.

A useful embodiment of motion correction described herein is to utilize the spatial correlation and/or time structure of the data of the input volumes to detect distortion and estimate the relative motion between object and scanner. This motion information can then be used to construct un-distorted views or data sets of the individual volumes. These un-distorted data sets or volumes can then be combined or merged into a single volume that is both motion artifact free and has improved image quality. Using the three-dimensional data sets shown in FIG. 10A and FIG. 11A, an overview of the motion correction and merging operations for two data sets is shown in FIG. 12. It is recognized that motion correction and merging can be generalized to more than two data sets.

Image Acquisition

Figure 10C:
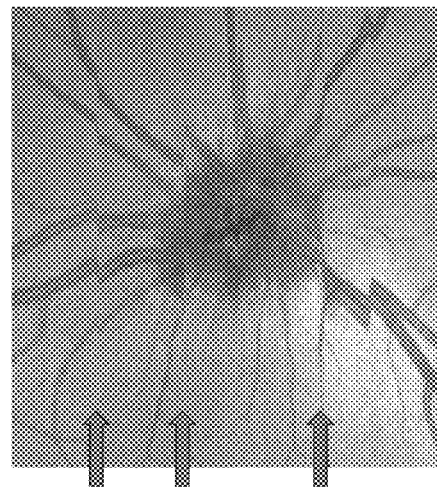
FIG. 10C is an OCT fundus image showing transverse motion effects.

In order to estimate and compensate for eye motion occurring in the volume, as well as fill in gaps in individual data sets, two or more volumes are acquired, where at least one of the volumes has a scan pattern that is considered complementary to at least one scan pattern associated with another volumetric data set. In the example embodiment which acquires data using raster scans, two raster scan patterns are considered complementary if the fast scan direction of one raster scan is at an angle of close to or at 90 degrees to the fast scan direction of the other raster scan, making the fast scan directions substantially orthogonal. Substantially here means that the absolute difference from a 90 degree angle does not exceed 10 degrees. FIG. 10A illustrates a scan pattern in which the fast scan direction of a raster scan is in the x direction, called an XFast scan pattern. FIG. 11A illustrates a complementary scan pattern in which the fast scan direction of a raster scan is in the y direction, called a YFast scan pattern. In this example, the fast scan directions of the volumes are acquired substantially orthogonal to each other in the coordinate system of the OCT device. Acquired in this manner, the complementary orthogonal volumes are affected differently by motion, which improves the motion correction. It is understood that the fast scan directions do not necessarily have to coincide with x and y directions of the OCT device coordinate system, but may be rotated by an arbitrary angle in the transverse plane of the OCT device coordinate system. In this particular example embodiment, the sets of A-Scan sampling locations in the OCT device centric coordinate system associated with the scan pattern of each volume are the same, or alternately, easily mappable to the same grid of locations. An example of an easily mappable set of sampling locations is two orthogonal raster scans covering the same area in the scan coordinate system, but with the scan patterns having a different number of A-Scans in the fast and slow directions. Scan patterns used in clinical practice often include more A-Scans in the fast direction than in the slow direction to balance sampling density with acquisition time and data set size. In the case when there are a different number of A-Scans in the fast and slow scan directions, the data can be mapped to a common grid of locations by resampling or interpolating as an intermediate step in the process. For example, in the specific case that there are more A-Scans in the fast direction than in the slow direction, OCT data can be resampled along the fast direction so that the resulting number of sampling points in the fast direction becomes the same as the number of sampling points in the slow direction.

For any given scan pattern, there is an association of every A-Scan with a device centric coordinate system, as well as an approximate time at which the A-Scan is imaged. The time at which an A-scan is imaged could be referenced to the start of the acquisition of the volume, for example, or any other temporal point of reference. The example embodiment uses knowledge of the time at which A-scans were acquired. However, time information does not have to be provided by the OCT device itself, but can be calculated from knowledge of the scan pattern without the OCT device having explicit support of A-Scan time-stamping. Therefore, it is understood that explicit time stamping of A-Scans is not a requirement for practicing methods and devices described herein.

In the example embodiment, 3D data sets are acquired where at least two of the scan patterns are complimentary. Thus, the sequence in which sampling locations are traversed is different between at least two of the scan patterns of the input data sets. The methods and apparatus described make use of the scan pattern related information to improve motion correction.

Figure 10B:
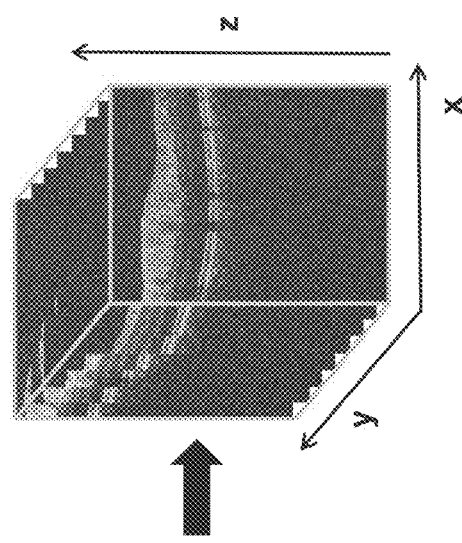
FIG. 10B is a set of cross sectional images from a three-dimensional OCT data set of an optic nerve head of a human retina.
Figure 10A:
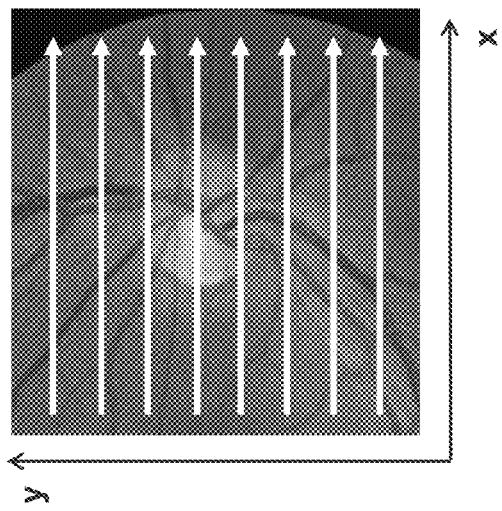
FIG. 10A is a fundus photograph with arrows indicating the fast scanning direction superimposed.

Examples of input data sets are shown in FIG. 10B and FIG. 11B, which show data acquired with a scanning priority in the x direction and scanning priority in the y direction, respectively. Both volumes show a distorted view of the true object structure and topography with low distortion along the respective fast axis and comparatively high distortion along the slow axis or direction. The correlation of observable motion characteristics with scan direction occurs because the distorting effects of the motion are smaller over shorter times. Discontinuities or gaps in the data are visible in the OCT fundus images for the two complementary data sets (FIG. 10C and FIG. 11C). Discontinuities can occur if there are rapid motions which result in rescanning of the same region of the object or missing regions of the object altogether.

It is implied that the OCT data is acquired in at least one step during the process. Systems and methods described herein can also process previously acquired OCT data.

Data Preprocessing

After the initial acquisition of the volumes, several optional preprocessing steps can be applied to the data. Preprocessing can reduce both the computation time as well as enhance the quality of the motion correction result.

Usually only a part of the region covered by a volume contains relevant structural information. For example, in most cases, only a sub range of the total axial range contains image data from the object tissue being imaged and no discriminating tissue features are visible outside of this region, since the object only covers a subset of the axial range of the OCT device. The region of interest for the motion correction therefore lies within the sub range where the object information is contained. Regions outside the region of interest where there is object information can be cropped out in the axial direction in order to reduce data size and computation time or complexity.

To speed up computation and reduce memory storage requirements, the data can also be reduced by down-sampling the volumes in the axial direction. In example embodiments, down-sampling is done using Gaussian reduction. However it is recognized that other methods may be used. The down-sampling may be applied multiple times. The resolution in the transverse direction is not influenced by this step. It is recognized that this step is optional and may be omitted in applications where very fine axial resolutions are desired.

Speckle noise present in the OCT images can reduce the accuracy of the image similarity measure. Effective noise suppression therefore can lead to better quality results. To avoid de-noising artifacts in volume positions where saccadic eye movement is present, median filtering is applied to each B-Scan separately instead of using a 3D technique. Typically in the example embodiment, a quadratic median window of size three or five is used. It is understood however that different noise reduction methods can also be used, such as 1D or 3D median filtering or 1D, 2D or 3D anisotropic diffusion, or other methods.

An intensity normalization of the image data can also be performed. In the example embodiment, a mean-variance normalization is employed which produces data with zero mean value and a variance of one. However it is recognized that other normalization methods may be used and normalization may be performed on amplitude, intensity, or other quantitative characteristics of the data. This operation can be performed on whole volumes. Alternatively, the data can be normalized on a per A-scan basis which is useful if there are non-uniform changes in brightness over a volume. This can occur if the OCT instrument has a significant variation in sensitivity with axial distance. Brightness, signal strength, or data value variation can also occur if there are vignetting artifacts in the OCT dataset, which can occur during retinal imaging when the OCT beam is at least partially obstructed by the iris or tissue surrounding the pupil of the eye. Correction of A-scan data value based on a known sensitivity vs. depth calibration can also be optionally applied.

It is implied that the OCT data is optionally preprocessed at least one step during the process. Systems and methods described herein can also operate on previously preprocessed data and process this data.

Motion Estimation

Example embodiments estimate the relative motion between the object and the OCT system during the scan procedure by using a registration process. An objective function is optimized (minimized or maximized depending on the formulation). The objective function takes into account the similarity between the two or more input dataset volumes. The spatial-temporal structure of the input data is also taken into account. The registration process yields several transforms or displacement fields, one for each volume. Each individual vector in each displacement field is related to a position on a 2D grid in the object coordinate system or object space or common motion corrected space. In this context, a 2D grid means that while the grid points itself have three-dimensional coordinates, the grid points form a plane. Therefore, there are only two degrees of freedom within the grid. The grid of positions corresponds to the common set of sampling locations in the OCT device coordinate system, mapped into the motion corrected space. Each transform or displacement field consists of three-dimensional vectors on this 2D object space grid, representing x, y and z displacements. For each volume and object space grid point, the corresponding displacement vector is used as an offset to sample the associated dataset data, which is defined in the OCT device coordinate system relative to the OCT device coordinate system location which corresponds to the object space grid point, in order to produce an interpolated A-Scan equivalent. Because of this, if suitable values are found for the displacements, the displacement fields can be used in conjunction with image resampling techniques to map data associated with the OCT data set from the uncorrected OCT device coordinate system to the common, motion correct object coordinate system. Therefore, the goal of correcting motion present in the acquired OCT datasets can be reached by finding said suitable values of each associated displacement field.

The Objective Function and its Optimization

In order to compute the transforms (displacement fields to undistort the data volumes), an objective function representing the registration goals is created and optimized with numerical computational techniques. The objective function itself takes the set of displacement field estimates, each of which is uniquely associated with one acquired data set, as parameters and produces a single real value as an output, as shown in FIG. 13.

Figure 13:
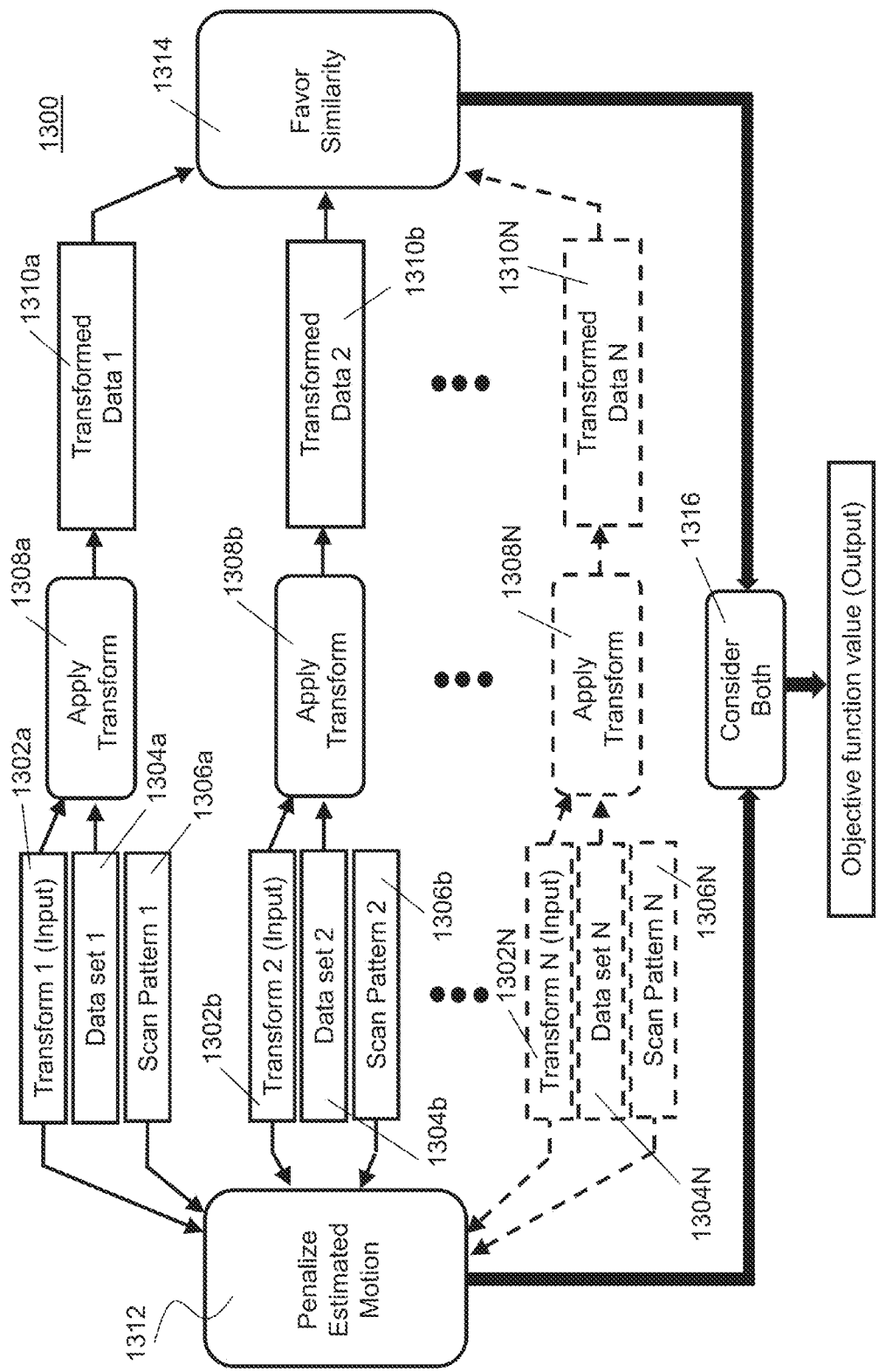
FIG. 13 is a flow-chart illustrating evaluation of an objective function according to an example embodiment of the present invention.

FIG. 13 is a flow chart showing process 1300 for evaluating an example objective function employed by the methods of the present invention. In steps 1302a, 1304a and 1306a, transform 1, data set 1 and scan pattern 1, respectively, are taken as inputs. In step 1308a, a transform 1 is applied to data set 1 to obtain transformed data 1. In steps 1302b, 1304b and 1306b, transform 2, data set 2 and scan pattern 2, respectively, are taken as inputs. In step 1308b, transform 2 is applied to data set 2 to obtain transformed data 2. In step 1312, transform 1, data set 1 and scan pattern 1 are compared with transform 2, data set 2 and scan pattern 2 to penalize estimated motion between the object and the scanning instrument. In step 1314, transformed data 1 and transformed data 2 are compared to favor similarity between two transformed data sets. In step 1316, the objective function is evaluated by assessing the relative strengths of the motion estimation penalty and the similarity.

Process 1300 can include additional steps, operating on transforms c through N, data sets c through N and scan patterns c through N.

Without loss of generality, this embodiment defines a lower objective function value to be better in the context of optimization. Therefore the optimization process consists of finding a suitable set of displacement fields that result in an objective function value, where a smaller value indicates a more suitable set of displacement fields. The objective function has two goals and: (1) favors high similarity among transformed volumes and (2) penalizes motion as modeled by the displacement fields or transforms.

Each data set acquired consists of possibly multiple data channels, defined on a discrete grid of data points in the OCT device centric coordinate system, as shown in FIG. 5. When a displacement field is applied to data values from an original or preprocessed OCT dataset, the offsets from the transform usually do not cause coordinates where data from the input dataset is to be mapped from to lay exactly on the discrete grid positions themselves, but in between grid positions. Because of this, image interpolation techniques are used to interpolate between values associated with grid positions in order to enable arbitrary positions to be sampled from the data. Example embodiments may employ cubic Hermite spline interpolation. This interpolation scheme, while still being computationally inexpensive to perform, enables the computation of smooth first derivatives, which is advantageous for the nonlinear optimization that is performed later. It is recognized that other interpolation techniques may be used depending upon the computation speed and performance requirements of the application.

When structural data from the input or preprocessed volumes, such as intensity data, is mapped to the common, motion-corrected object space using displacement fields with suitable values, the resulting mapped individual data sets are likely to be similar to each other. On the other hand, if the displacement fields are not calculated suitably, it is likely that the mapped structural data between multiple data sets is less similar. Therefore, one part of the objective function is to favor a high similarity between the set of transformed structural volume data. The data which is transformed and tested for similarity can be from the input datasets directly. In the case that one or more preprocessing steps have been applied to input datasets to generate preprocessed datasets, application of the transforms and similarity assessment can also be performed on preprocessed data sets. Volume data is transformed by mapping structural data values associated with the acquired data sets using the respective displacement fields which are input to the objective function. For each grid position, a value that becomes lower for progressively higher similarity between the mapped A-Scan data is computed and summed up over all grid positions. In the example embodiment, a sum of squared differences (SSD) approach is used to compute these values. In the case that there are only two acquired volumes, similarly mapped data between these two volumes is subtracted and squared directly to form the similarity indicator. In the case that there are more than two volumes, a set of pairings between mapped volumes is generated, SSD calculated for each pairing, and the values summed over all pairings. The pairings are chosen so that there is a graph structure with linkages formed by the pairings such that all volumes are at least connected. This means that when starting from any volume, any other volume can be reached by traversing the pairings between the volumes.

In general, when relative motion occurs during the acquisition, the position scanned on the object differs from the case where there is no motion and depends on the specific motions involved. However, the velocity and acceleration of the relative motion are limited, and the position is determined by the integration of the velocity over time. Because of this relationship, the expected magnitude of change in position between scanner and object is related to the amount of time having passed between acquiring different data samples. The embodiments incorporate information about the scan pattern to improve the motion correction.

It can be assumed that the relative motion between the instrument and the object has limited range, velocity, acceleration and frequency. The relative position is the integral of the relative velocity in time and there is a physical limit to the change in relative position within a certain timeframe. The purpose of the second goal of the motion estimation is to assure that the transforms that are estimated are found in such a way that the spatial-temporal structure associated with the sequential aspect of the data acquisition process is taken into consideration. The motion therefore has to be smooth in time. In the case of example embodiments, motion can be expressed as the derivative of the displacement field with respect to the time structure information. Example embodiments add a so-called regularizer to the objective function to include prior knowledge of the acquisition process that penalizes modeled motion. This regularizer calculates the sum over all grid points and all volumes of the square of the L2 norm of the derivative of the displacement field vectors with respect to time for each displacement field. The derivative can be calculated approximately, using finite differences or other known methods. A factor to treat the transverse and axial motion differently is introduced, which scales the axial dimension of the time derivative prior to application of said L2 norm squared. It is understood that the methods and systems described herein can also employ other regularizer formulations, which also penalize modeled motion.

In order to reach a good motion correction result, the two previously formulated objectives, i.e., structure similarity and smooth motion goal, should not be considered in isolation. It is preferable to include a balance between both goals. One way to construct the objective function from the two terms, each of which representing one goal, is to sum the two objectives (goals, or measures). A positive factor can be applied to one of the objectives before summation, to provide a relative weighting. This factor can be tuned for optimal performance and in general depends on the concrete set of input volumes and other settings. However in practice, the resulting motion correction quality is rather stable over a wide range of regularizer weighting factors.

To find a motion estimate, the objective function has to be optimized with respect to the displacement fields of the volumes. Example embodiments may use a line search based quasi-Newton nonlinear optimizer, e.g. the limited memory Broyden-Fletcher-Goldfarb-Shannon technique. However it is recognized that many other optimization techniques may be used. It is also understood that the optimization itself can be terminated at any time, for example for execution time reasons or because the current estimate is deemed good enough or close to optimum. Other termination criteria can also be used to practice the methods and devices described herein.

Figure 14:
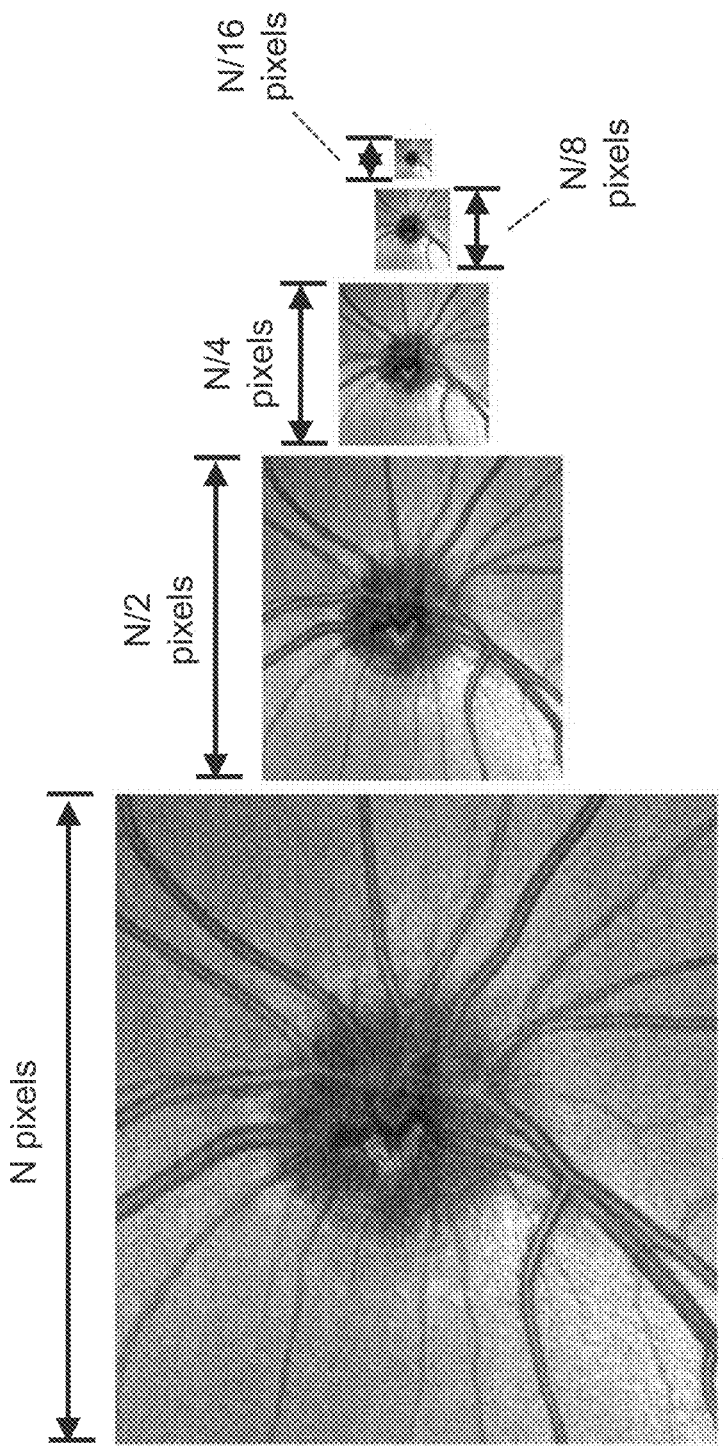
FIG. 14 is a collection of five images of the fundus of a human eye in en face view at five levels of resolution measured in pixels of the display.

In general, this and other non-linear optimizers only converge to a local optimum within a region around the starting point. To find a solution that is near a global optimum and reduce computation time, a multi-resolution approach is exploited. The complexity of the objective function is reduced a certain number of times, with each multi-resolution formulation, called a level. In practice, using five multi-resolution levels is often sufficient, but depends on the particular parameters and characteristics of the input data sets. Transforms that map the displacement field estimates from one level to a more complex one are formulated. For the purposes of computation, the data associated with the displacement field of each volume is treated as a 3 channel 2D image, one channel for each dimension of the displacement vectors, on the common grid in the object coordinate system. Standard image interpolation techniques are then used to generate higher resolution representations of this field. The original optimization problem is the most complex level. The complexity reduction is performed by re-sampling the dataset itself, as well as the associated time structure information to a smaller number of grid points. Successive data reduction on the image data results in a so called resolution pyramid, as shown in FIG. 14.

The optimization is performed at the coarsest pyramid level first until an optimum is reached or a certain number of iterations have been performed, or no better parameters can be found. Then the solution is mapped to the next level with higher complexity by using up-sampling. The result from a completed level forms the initialization for the next multi-resolution level optimization step. The optimization proceeds with this new level and initialization. Once this process finishes, the result is mapped to the next appropriate multi-resolution level. The process is repeated until the original resolution optimization process has finished.

The outcome of the completed optimization process is a set of displacement fields, one for each volume, which also can be considered motion estimates for the volumes.

Generation of Registered (Motion Corrected) Datasets

After the transforms or displacement fields have been estimated, one or more motion corrected data sets are constructed. Motion corrected data is generated by applying the corresponding calculated displacement to one or more of the input dataset's data channels, such as intensity, Doppler shift, or preprocessed versions thereof, depending on the specific application.

Instead of explicitly constructing the registered datasets, the data can also be partially constructed on demand by applying the transformation to the data set.

These motion corrected data sets can optionally be used in a data merging step described in the next sections. It is not necessary to merge data sets and motion corrected datasets may also be used themselves without merging, although merging has the advantage that it improves image quality.

Data Combination (Merging)

Figures 15A, 15B:
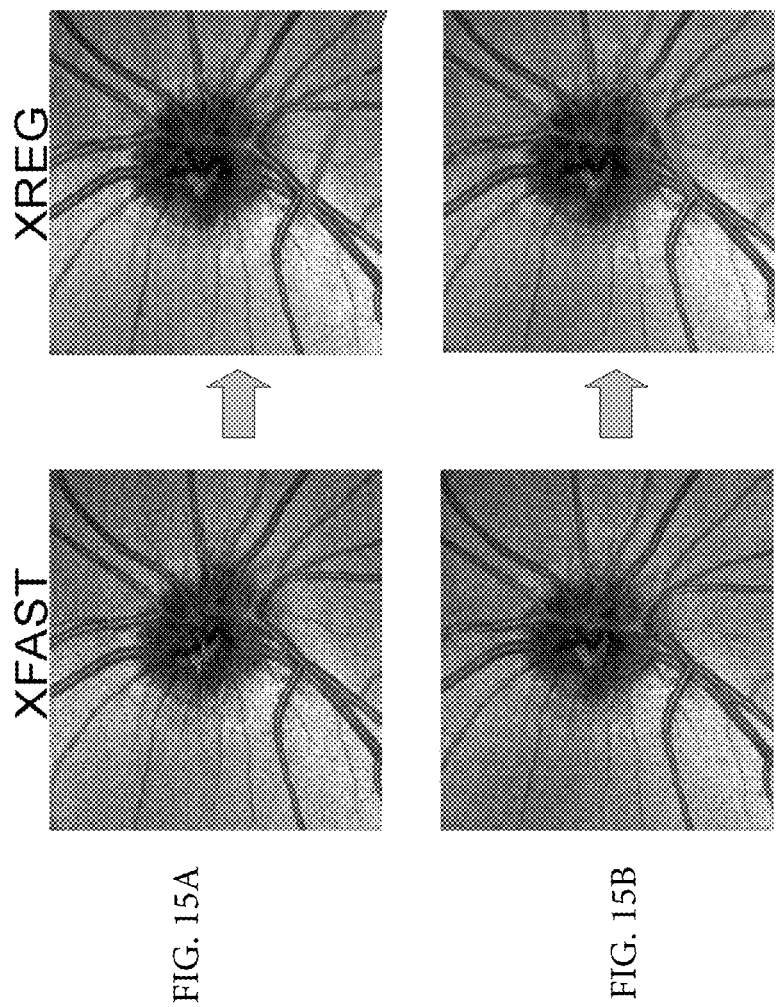
FIGS. 15A and 15B are illustrations of the registration and merging process of an example embodiment of the present invention.

The preceding motion compensation calculates a displacement field for each acquired volume. The displacement field models the movement of the target during the acquisition. The application of each displacement field to the associated distorted data set produces motion compensated data sets within a common space. Some example embodiments then combine these independent datasets to create one of higher quality. The relative quality of the data samples in the registered volumes is taken into account during this process. FIGS. 15A and 15B show a schematic diagram of an example merging process of the present invention that uses the example of two volume registrations. Specifically, FIGS. 15A and 15B represent a superimposition of OCT images of a human eye obtained by scans that employ orthogonal slow and fast directions, scan XFAST (panel A) and scan YFAST (panel B). Each scan is then registered (i.e. anatomical features of the image are assigned absolute coordinates, independent of the scanning device of the position of the object), creating registered scans XREG and YREG. Finally, registered scans are merged as described herein.

From the motion estimates, the input volumes are transformed to generate registered volumes. These volumes are then combined using a voxel-wise weighted sum between them. While some example embodiments use this technique, it is recognized that other techniques for combining or merging data are possible.

Due to relative motion between the instrument and object and the sequential sampling during acquisition, the object is sampled with varying coverage. Regions of the object could be either scanned several times (over-sampled) or not scanned at all (under-sampled). This scenario is illustrated in FIG. 8B. In the case of under-sampled regions, gaps occurring during motion compensation are interpolated from neighboring A-Scans in the input volume when mapping data into the common object space. Thus, these intensity values do not represent the actually acquired data but information from adjacent regions. However, if multiple volumes are combined or merged, under-sampled, unscanned regions are significantly reduced because data from other volumes is likely to be available over most of the unscanned region in a single volume.

It is possible to combine the motion compensated volumes by direct averaging, i.e. setting weights to 1/N for N volumes to be merged. However, a voxel that was mapped to a certain position in the object space grid to fill a corresponding hole in the input volume will then have the same contribution compared to A-Scans that contain true target data. This approach can result in a local degeneration of image quality.

One way to detect holes (voids) in data is to look for regions in the original volume that were sampled from more often than others during the production of the final registered volume. This measure, which is the same within each A-Scan in the registered volume, is called the sampling density. A relatively high sampling density is an indication that the region from the input volume was used to fill gaps in the registered volume. A second indication of sample quality is determined by assessing if a voxel in a registered volume was generated by sampling completely or partially outside of the input volume area. This measure is called sample validity.

One way to compute an estimate of sampling density is to first create a 2D image with a size being a multiple (for example 4 times) of the x/y size of the corresponding volume and to initialize all pixels of the image to a very small positive value. The bigger size of this image is used to achieve a certain degree of subpixel accuracy, for example a factor 4 will provide 2 additional bits of accuracy. This image represents the two dimensional area of the original volume corresponding to the two dimensional grid of A-Scans. Estimation is done by additively drawing a kernel, for example a truncated Gaussian, into this image for each sample that is taken to generate the registration result. The drawing itself is done by centering the kernel onto the position the sample was taken and adding the kernel values to the density estimation image values. If the kernel is partly outside of the image, the values can still be added at the nearest edge pixel in order to mirror the behavior in the volume sampling routines.

In order to use these estimation images for the weight computation they have to be mapped into the common object space. This can be done by applying the transversal components of the displacement fields to said image values, similar to the three-dimensional case, but without using the axial (z) displacement information. This process leads to a set of two dimensional images, one for each volume that are to be merged, that estimate sampling densities and exist on a two dimensional grid in the common object coordinate system.

A sample validity value can be generated corresponding to every voxel that is about to be merged by checking whether the data mapping process that generated said voxel sampled volume data that was mapped from outside of the area were data was collected in the OCT device coordinate system. In this case, sample validity is assigned a very low positive value. Otherwise, example embodiments assign the value 1 as sample validity.

Example embodiments combine the acquired volumes according to the estimated sampling density and sample validity to avoid the local quality degeneration mentioned before. Weights are generated from sampling density and sample validity which control the influence of each voxel for each data set in the final merged data set. For example, a weight can be assigned to each given data voxel of each registered volume in the following way: Assign a preliminary weight to the voxel by dividing the associated sample validity by the quantity one plus the associated sampling density, said quantity raised to a power of e.g. eight. This power parameter is subject to tuning and depends on the value ranges and distributions of sampling density and sample validity values. This step is followed by a normalizing step that scales weights, which are associated with a set of data values to be combined, by a common factor which assures that the sum over said weights equals 1. In addition, weights that are much lower than equal share can optionally be snapped to zero and the remaining weights renormalized. This process leads to weights that are higher when the sampling density is relatively low when compared to the other sampling densities. Weights are also higher if the sample validity is relatively high. This scheme leads to a lower influence of data samples that were only mapped to a specific position in the motion corrected object space to fill a gap in sampling of the originally acquired volume, thus increasing quality of the merged output.

After the weighted sum of the voxels is calculated for all values, a final optional post-processing step can perform thresholding and range conversion on the merged motion-corrected dataset.

General Description of Principles of Motion Correction

The following sections describe the general principles of motion correction. The steps shown need not necessarily be performed serially and may proceed in parallel when possible. FIG. 12 shows a high level flowchart of an example method. First, at least two OCT datasets are acquired. At least one of the datasets should be a dense scan of a region in the transverse plane. The data is then subjected to one or more optional preprocessing steps that are designed to improve the performance of example methods as well as the execution speed. The preprocessed data is then used for the actual motion estimation step, which finds a transform for each input dataset that corrects the distortion caused by motion during the dataset acquisition and also transform the datasets into a common space to correct motion. Once these transforms are found, one or more of them can be applied to the same data channel as used during the estimation process, or to different data channels from the same dataset, in order to generate one or more motion corrected datasets. Finally these motion corrected datasets can be combined to a single set that is both free of motion artifacts and also has improved data quality.

Dataset Acquisition

Example embodiments are described with respect to 2D and 3D-OCT volumetric data sets, but it is recognized that it can be applied to other imaging modalities that are characterized by a scanned data acquisition process which acquires image information at different positions on a sample material or tissue at different times. The multi-dimensional OCT datasets are composed of data samples which are acquired according to a specific scanning pattern. The acquisition of the dataset can be described using a three-dimensional instrument scanning coordinate system. This coordinate system can be defined by an origin and three orthogonal basis vectors. The first two basis vectors span the transverse plane of the OCT device. The third basis vector is perpendicular to the first two basis vectors and points in the axial direction (FIG. 3). The scanning range for the OCT beam in each of the two transverse directions is defined by a scan trajectory or scan pattern and determines the transverse region of the object material or tissue that is being imaged. The axial or depth measurement range of the OCT instrument determines the depth range of the object being imaged.

Figure 28:
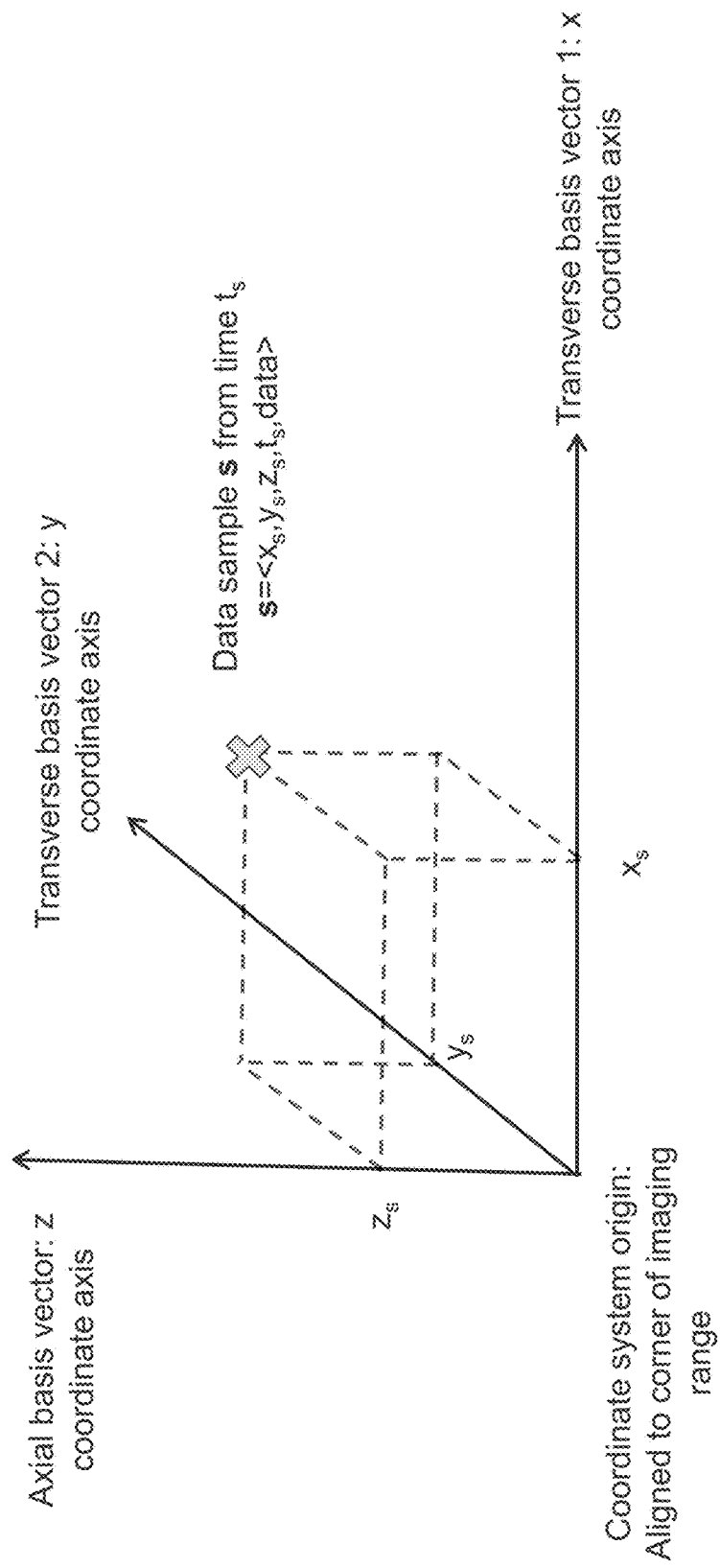
FIG. 28 is a schematic diagram of a general coordinate system employed by the example embodiments of the present invention.

The position of each sample of which the multi-dimensional OCT dataset is composed of can be specified relative to the said basis. The position is defined by a three-dimensional coordinate vector that specifies the location of said data sample in the scanning cube. The approximate absolute time relative to the start or the approximate difference in time relative to the last data sample that was captured is also known because there is timing information associated with the trajectory used to control the scanning mechanism for the beam positioning. If the relative time information between data samples and the starting point of the acquisition of a particular image is known, the absolute timing information, i.e. the total time passed since the first imaging sample of that particular image, can also be constructed. Using this information, the acquired image data can be fully described by the start time of the acquisition and a set of tuples, an ordered list of elements. The set size equals the total number of data samples that were captured for that image. FIG. 28 shows a schematic view of the relationship between a single data sample and the coordinate system. Each tuple $s=<xs,ys,zs,ts,data>$ consists of the data content of the sample itself, the three-dimensional coordinates relating to the position on the OCT scanning coordinate system and a time value is when the position was sampled.

Figure 29:
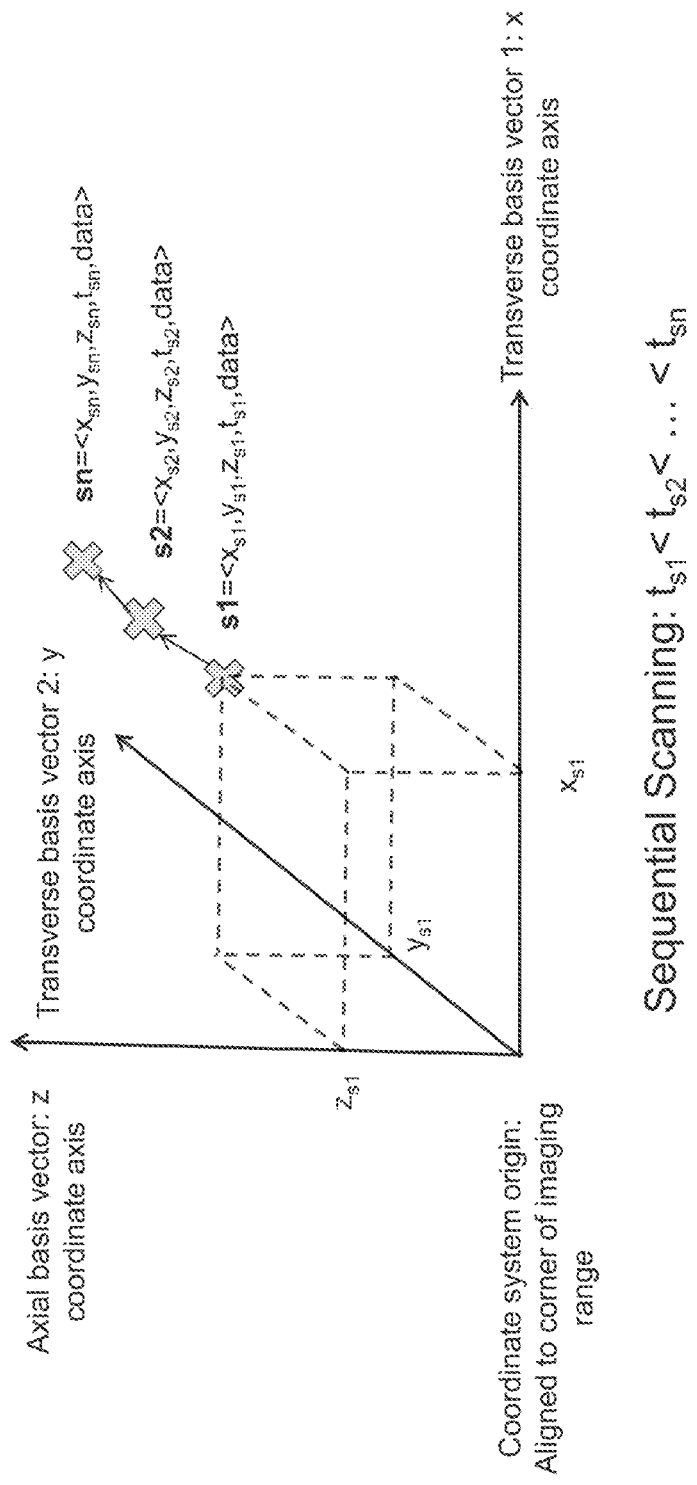
FIG. 29 is a schematic diagram of a sequential sampling pattern in the general coordinate system of FIG. 28

FIG. 29 shows an example of sequentially sampling multiple positions to form a dataset. Here, multiple data samples $s1$, $s2$ through $sn$ are collected. Because the example shows sequential scanning, the times associated with the data samples are sequentially increasing from one data sample to the next.

In cases where the OCT device acquires individual A-Scans substantially instantaneously (as is the case for Fourier Domain OCT) each A-Scan can be thought to acquire multiple data samples at different axial depths at the same time. Substantially instantaneously here means that each A-Scan is acquired within less than one millisecond. The samples along the axial direction of each A-Scan are obtained at the same transverse coordinate in the instrument coordinate system. The axial coordinates of the A-Scan's data samples are spaced equally in the z direction of the instrument coordinate system. Embodiments are assumed to be primarily used in conjunction with such systems which instantaneously acquire individual A-Scans. However, in the general, data samples of a dataset do not have this special relationship with each other. It is also recognized that optical refraction effects may result in changes in the direction of the OCT beam such that the axial direction is not necessarily aligned to the z axis. These cases can be treated by preprocessing OCT image datasets to compensate for refraction and are also supported by the example embodiments.

Furthermore, this model to describe image acquisition also applies to apparatus which simultaneous collects multiple data samples or A-Scans at once using multiple imaging beams. In this case, the associated time value will also be the same for the concurrently recorded data samples. The use of multiple imaging beams enables increases in data acquisition speed and in the case where multiple beams are scanned independently, enables enhanced correlations between the time structures of datasets which will improve registration performance.

The notion of complementary scan patterns can be explained mathematically by treating the 3D position of each data sample in the instrument coordinate system as a function or relation of time. This means that each time can be associated with one or more sampling positions. As time proceeds, a gradient-like concept can be defined that is a vector for each data sample pointing to the next corresponding data sample in time. Corresponding in this context means that the samples are recorded with the same imaging beam and/or are at the same axial scan index in the case of A-Scan based systems. The resulting vector field is unique for a specific scan pattern. Two scan patterns are said to be complementary if these vector fields are dissimilar or uncorrelated. A basic example of complementary scan patterns are raster type scan patterns with orthogonal fast axes (FIGS. 10A through 10C and FIGS. 11A through 11C). In general, the motion correction works best if the set of scan patterns that are used contains significantly complementary patterns.

In addition to the instrument scanner coordinate system, it is also possible to define a coordinate system on the object material or tissue being scanned. If there is no relative motion, then the instrument coordinates and the object coordinates have a fixed relation to each other and the 3D-OCT volumetric dataset accurately represents features in the object material or tissue. However, during dataset acquisition, the motion of the object material or tissue, as well as motion of the instrument, can contribute to distortion of the dataset because the actual position of the OCT beam on the object material or tissue as described by the object coordinate system differs from the desired position of the OCT beam as described by the instrument scanner coordinate system.

FIG. 10A through FIG. 10C show the example of a raster beam scanning pattern used in the standard case that the OCT device acquires instantaneous scans in the axial direction. In the raster pattern, axial scan data is acquired sequentially by fast scanning the OCT beam along a given transverse direction (the x direction in FIG. 10A or FIG. 10B) and repeating the fast transverse scan with the scan displaced progressively along a perpendicular direction (the y direction in FIG. 10A or FIG. 10B). The beam is repositioned to the beginning of each sequential fast scan by a flyback, a rapid scanning of the beam to the origin of the next transverse scan, as shown in FIG. 4. In this example, axial scan OCT data is not acquired during the time of the flyback. The raster scan can be thought of as acquiring a set of cross-sectional images, B-scans as shown in FIG. 10B. More generally, the collection of B-scans at different plane positions or equivalently the collection of axial scan data from a transverse region of the object material or tissue forms a 3D-OCT volumetric dataset.

The raster scan pattern obtains axial scan data at points spaced along a square or rectangular grid covering a transverse region of the object. Depending on the axial scan acquisition rate of the OCT instrument and the velocity of the OCT beam scanning, the axial scans may be acquired with different axial scan spacing in the x and y transverse directions. Example embodiments of motion correction registration and merging use axial scan positions which are equally spaced in the x and y transverse directions. This is because the complementary scan pattern which performs rapid scanning along the y direction will have axial scan data which have the same spacing as the scan pattern which rapidly scans along the x direction.

FIG. 30A through FIG. 30G show examples of OCT beam scanning patterns and the complementary patterns. A standard raster pattern and its complementary pattern is shown in FIG. 30A pattern (shows) (XFast and YFast). The bidirectional raster pattern (FIG. 30B and FIG. 30E) can be used if very high speed scanning is required. The bidirectional raster does not use a scanning flyback as in a standard raster (FIG. 30A) and scans the beam with substantially equal velocity in the forward and reverse scan directions. As used herein, two values of velocity are "substantially equal" is the two values differ by less than 10%. The bidirectional raster acquires data on both the forward and reverse scan, thereby optimizing the amount of axial scan data that can be obtained in a given measurement time. A bidirectional raster pattern acquires axial scan data that can have a varying spacing in the direction perpendicular to the scan. For the example of rapid scanning in the x direction shown in FIG. 30E left pattern, the axial scan spacing has a small variation in the y direction.

Figure 30:
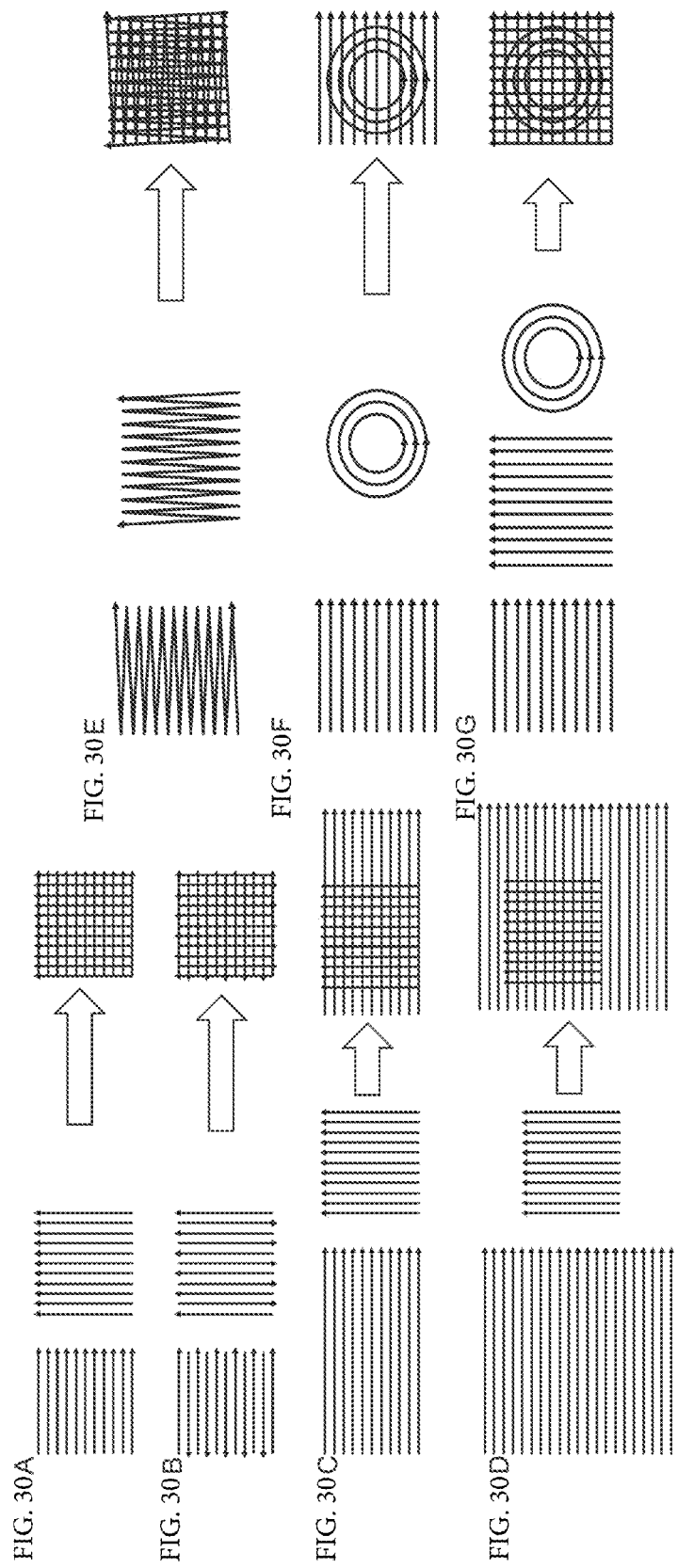
FIG. 30A is an illustration showing example complementary scan patterns where the arrows indicate scanning direction and the scan patterns are unidirectional raster scans.
FIG. 30B is an illustration showing example complementary scan patterns where the arrows indicate scanning direction and the scan patterns are bidirectional raster scans.
FIG. 30C is an illustration showing example complementary scan patterns where the arrows indicate scanning direction and one scan pattern is rectangular while the other scan pattern is square.
FIG. 30D is an illustration showing example complementary scan patterns where the arrows indicate scanning direction and one scan pattern is larger than the other scan pattern.
FIG. 30E is an illustration showing example complementary bidirectional scan patterns where the arrows indicate scanning direction and the raster scans are not parallel.
FIG. 30F is an illustration showing example complementary scan patterns where the arrows indicate scanning direction and one scan pattern is a raster scan while the other scan pattern is a cylindrical annulus scan.
FIG. 30G is an illustration showing example complementary scan patterns where the arrows indicate scanning direction and multiple scan patterns consisting of two raster scans and one cylindrical annulus scan are shown.

FIGS. 30 C, D, F and G show other examples of OCT beam scan patterns, including scanning a rectangular transverse region of the object material or tissue, scanning a cylindrical annulus, or scanning a large region and a complementary smaller region which is contained in or partially overlapping the larger region.

FIG. 30 D shows an example of a large square or rectangular region that is scanned rapidly in the x direction and complementary scan pattern consisting of a narrower region that is scanned rapidly in the y direction. The complementary scan pattern scans the entire y extent of the initial scan pattern, but a subset of the x extent. This type of scan pattern might be used in cases where there is insufficient time to allow scanning two complementary patterns which are substantially covering the same region. This type of pattern may also be used in cases where data from two equal regions does not have sufficient quality to permit the entire volumetric data set to be used for the registration. In this case, a subset of the data corresponding to the regions shown in FIG. 30 D could be extracted and used. It is recognized that the scan patterns shown in FIG. 30A through FIG. 30G represent examples and many other scan patterns are possible. It is also recognized that more than one complementary scan pattern can be used for a given scan pattern.

In example embodiments, multiple 3D-OCT volumetric datasets are acquired using complementary scanning patterns. However, it is also possible to acquire multiple 3D-OCT volumetric datasets with similar or complementary scan patterns with the same time interval using an OCT instrument having multiple OCT scanning beams. OCT instruments having multiple scanning beams enable high speed data acquisition because multiple axial scan data is acquired from different positions on the object material or tissue at the same time. For applications in clinical imaging, such as ophthalmology, safe tissue exposure limits the allowable incident optical exposure on a given position and therefore limits the maximum data acquisition rate because of signal to noise tradeoffs. The use of multiple beams can enable higher data rates. In addition image acquisition is also possible by using multiple beams as it is possible to simultaneously acquire data from complementary scan patterns. This has the advantage of enhancing performance of the motion correction, registration and merging. These embodiments are described in more detail in a later section.

The time information associated with each axial scan within a 3D-OCT volumetric data set is an important parameter because it is used as an input to the motion correction and registration. The relative motion between the OCT instrument and the object material or tissue is constrained to be within certain limits of amplitude, velocity, acceleration or frequency. These constraints on the allowable motion are used in conjunction with measures of volumetric data similarity during the motion correction process.

The following sections assume the general case of each dataset consisting of the set of tuples composed of 3D position in the imaging instrument coordinate system and associated time and actual data. If certain descriptions refer to the more specific case of instantaneous A-Scan based datasets, this fact is explicitly mentioned.

Data Preprocessing

Preprocessing of the dataset can consist of several steps in order to transform the input data to a form that is more suited for motion correction. In the following sections, these steps are described. In a practical implementation, any subset of these steps can be performed as preprocessing. Where possible, steps can be executed in parallel. The steps detailed in the following section do not necessarily have to be performed in the same order as given in the description.

Data Selection

One stage of preprocessing is to select what part of the incoming dataset is used for the motion correction, especially for evaluating similarity in a transformed state. The data used should contain information that is similar when data samples are captured at the same position at different time steps and dissimilar if the data samples were recorded at different positions in the object coordinate system. In addition, the data selected, along with further preprocessing, should be well suited for processing. The details of which depend on how the similarity goal between the actual data of the dataset is expressed in a particular embodiment.

OCT data can be expressed as interferometric data which is output from Fourier domain detection, as field amplitude data, complex field data, linear intensity data, log intensity data or in other forms. For imaging applications in materials or tissues where there is significant optical attenuation with depth, OCT data is usually viewed in log intensity or other compressed form to expand the viewable dynamic range of the image. It is also possible to obtain other types of data from OCT measurements such as Doppler flow, power Doppler, polarization sensitive, birefringence or degree of polarization non-uniformity, spectroscopic and others. For example embodiments, one typical type of data to select for processing is OCT intensity data. The intensity data can be linearly scaled or transformed to logarithmic or another compressed scale. In addition, the data can have further standard OCT processing steps applied, such as intensity thresholding to reduce noise, or rescaling to occupy the full dynamic range of the representation. It is also possible to use more than one type of input data as the basis for the subsequent processing steps. For example, log intensity data can be used for performing motion correction and registration, while the information about motion correction transforms can be used to motion correct and register other data which is obtained from the OCT measurement such as Doppler flow, power Doppler, polarization sensitive, birefringence, degree of polarization uniformity or spectroscopic data, among others.

Noise Reduction

In general, the input OCT data has background noise as well as speckle noise. Depending on the subsequent motion correction and registration processing steps, it is possible to perform image processing steps that decrease the noise level in the volumetric dataset. Noise reduction can be performed by processing each A-scan independently, processing a set of multiple A-scans that are close with respect to both time and space, or processing depending on spatial closeness in the data set as referenced from the instrument coordinate system. One example of noise reduction that can operate on intensity data is median filtering in 1D, 2D or 3D with a suitable window size. However, a wide range of other noise removal techniques can also be used.

Dataset Rescaling

In order to achieve high speed processing and address execution time limitations, it can be advantageous to rescale the dataset in one or more directions. In the context of a general dataset, rescaling means increasing or decreasing the number of tuples, such that the spacing of data samples, according to one or more dimensions in the instrument coordinate system, is changed. One example would be to reduce the resolution in the axial or transverse direction of each dataset. The amount of data that needs to be processed in subsequent steps is thereby reduced. Another example occurs in cases where the spacing between pixels in axial direction is different between input datasets. The data can be prepared by increasing or decreasing the axial resolution of one or more datasets by re-sampling so that axial spacing is equal for all datasets. The same process can be performed in the transverse directions if the pixel resolutions of the input datasets images given by the spacing of sample points in the scan coordinate system are not equal. In the case of raster type scans, a rescaling in the transverse direction is preferably performed along an axis where the time difference between the sampling points is smallest.

Feature Computation

Instead of using the data channels that were selected during preprocessing directly for the motion estimation, a feature computation step can be performed. The purpose of this step can be to enhance the performance of the motion correction step in conjunction with the concrete similarity measure that is used. Another advantage is that the dimensionality of the output data can be reduced with respect to the input dimensionality, while the information that can discriminate data from different positions of the object is kept. This can both decrease necessary computations during motion estimation and improve motion estimation results as ideally irrelevant information is discarded.

Data Normalization

In order to bring the data content of the datasets into a defined range and correct for global differences in the data range, normalization can be applied. One example is brightness differences when intensity data is used. Such differences can be caused by different parameters used for the standard OCT image processing or differences in the distance of the OCT device to the scanned object for sequential acquisitions. This effect can be caused by the so called sensitivity rolloff typical in OCT imaging systems that decreases average signal level depending on the axial scan depth. Effects such as vignetting can also cause brightness differences depending on the transverse position of the data sample relative to the beam.

One example of data normalization is to normalize the intensity distribution of each dataset such that the mean intensity, or other structural data value after normalization, is zero and the variance of the intensity is 1. A similar normalization that normalizes all datasets in the same way would do the same for the intensity distribution over all datasets. Finally, a mean and variance based normalization can be performed on each A-Scan individually. This way, brightness changing effects can also be effectively compensated.

Selection of Data Samples

When multiple datasets are used as inputs to example embodiments for motion correction, there can be cases where the scanning pattern for one or multiple input datasets covers a much larger region in the instrument scanning coordinate system than other inputs. The actual region of interest in the scanning coordinate system on which to perform motion correction on might also be a sub-region of the region that was covered by the original OCT sampling patterns for each input dataset.

In this case, a 3D region of interest can be defined either by user input or automatically. For example, automatic region of interest generation can be performed by taking the intersection of all input sampling regions as given by the sampling patterns. One particular way of representing a region of interest is as one or more oriented bounding boxes in the instrument coordinate system. Alternatively, shapes that are more suitable to predominantly circular or elliptical scan patterns can be used.

Figure 31:
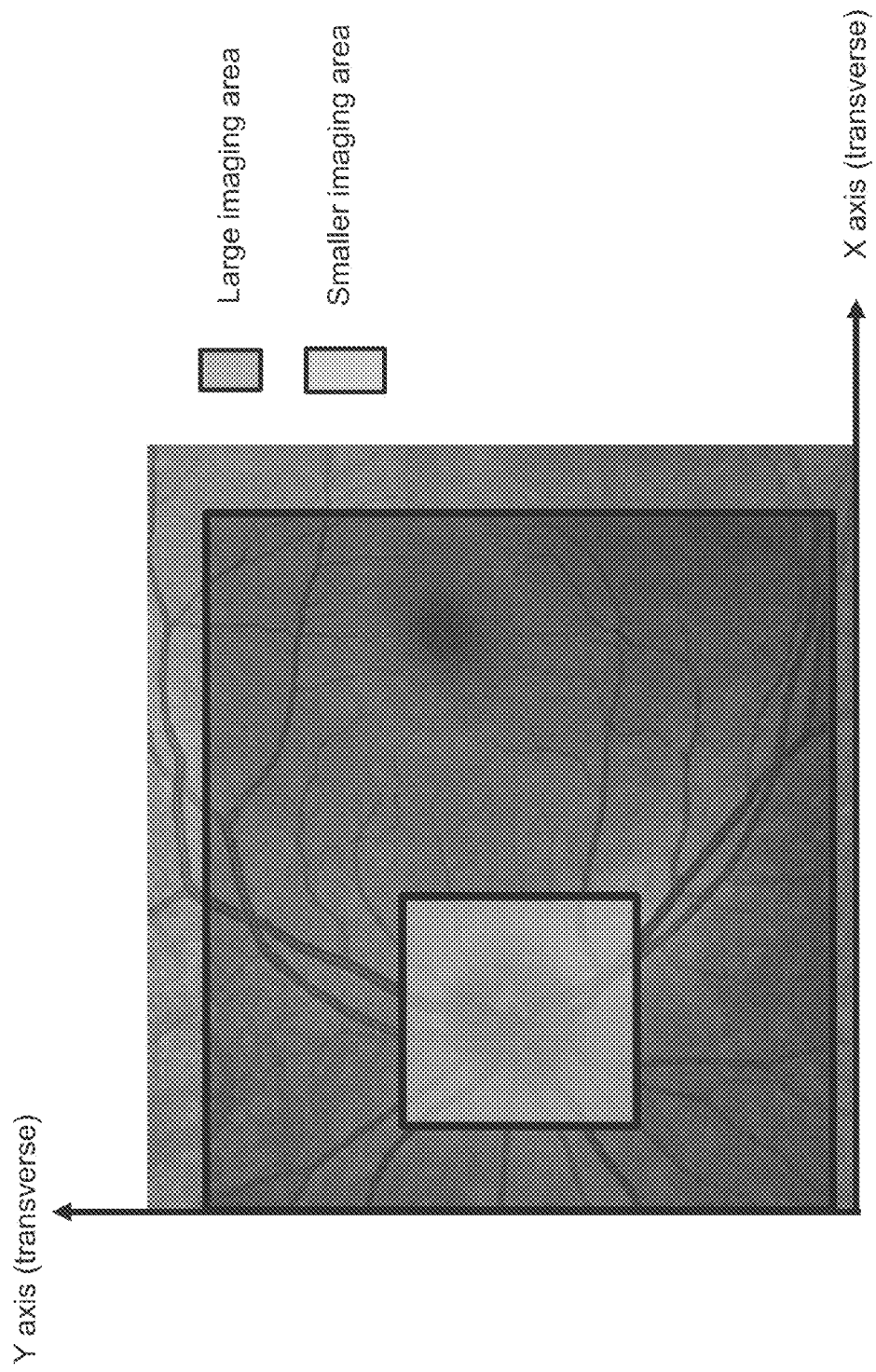
FIG. 31 is an image of a region of a human retina having two overlapping imaging areas.

When a region of interest is defined, all data samples can be tested to see if their scan location is within the region of interest. If this is not the case for a particular sample, it is excluded from further processing. This way processing can optionally focus on important areas. This allows optimized motion correction between OCT images that cover the same area, with a subset of images covering a much larger or much smaller area. FIG. 31 shows an example from the context of retinal imaging of this principle where one dataset covers a much larger region in instrument space than the other. Data samples that are within the intersection of these regions can be selected from both datasets for further processing.

Misalignment Compensation

In specific applications of OCT imaging, such as for ophthalmology, the imaging beam passes through a lens like object such as the cornea and lens of the eye before hitting the actual object of interest such as the retina. In this case, the biological lens will actually focus the OCT beam onto the retina. In such a scenario, the OCT image will show a relatively even (flat) view of the surface of the retina if the OCT beam hits the cornea in the center. On the other hand, if the beam does not hit the cornea in the center, relative optical path length differences occur at the extremes of the transverse scanning range. These length differences lead to a view on the retina that is tilted with respect to the case where the beam would be hitting the cornea in a centered position. Such changes in relative alignment can especially occur between sequential dataset acquisitions, thus causing the surface to look straight in one dataset and tilted in the other. This effect is also enhanced because OCT data is often displayed with a non-uniform aspect ratio where different dimensions in the data set are stretched or compressed in order to better display features of interest. In ophthalmology, OCT images are typically displayed with an expanded scale in the axial direction in order to better display the thin structures of the retina.

The tilting effect causes problems for the motion estimation as it will treat the tilting as a strong axial motion which is penalized by the modeled motion goal. This will cause the motion estimation to fail in severe cases of such misalignment.

In order to avoid problems associated with the tilting effect, a processing step can be added that estimates the tilting, for example by fitting a plane to the dataset. The plane can be fitted to features such as the first highly scattering material that is encountered, or measurements, such as centers of gravity for the brightness information along each A-Scan.

When a plane has been fitted to each dataset the data can be corrected such that the data is aligned and the calculated planes are even. The correction can be achieved by moving the data in the axial direction according to the distance of the measured plane with the even plane. It is recognized that other methods of tilt compensation can also be used.

Motion Estimation

Transform Parameterization

The basic idea of motion correction described herein is to find a set of transforms. There is one distinct transform for every input dataset. The transforms are used to map the data as it was recorded during each dataset acquisition into one single common coordinate system. The governing concept is that data that is mapped into this common space is freed from the distortion effects that the motion produces during each acquisition. Conceptually, this can thought of as moving data samples from the scanner coordinate system to the coordinate system of the object that is being scanned. Also, said object coordinate system can be thought of as an OCT beam instrument coordinate system that is compensated for the effects of relative motion between the scanner and the object in all three dimensions. The single coordinate system is called the registered or motion corrected space or coordinate system.

In this context, scan patterns that acquire predominantly two dimensional datasets are distinguished from scan patterns that acquire a dense 3D sampling pattern. 2D type patterns do not have a dense sampling of a true 2D region in the transverse plane. 3D type patterns cover a significantly two dimensional region of the transversal instrument coordinate system. This differentiation can either be made automatically by analyzing the sampling patterns of each input dataset, by the user, or the designer of the scan pattern. Also, there are boundary cases where the decision can be made arbitrarily. Fundamentally, a dataset is considered 3D type if the sampling of data points is covering a 3D region and is dense enough so that data interpolation techniques can be successfully used to interpolate between neighboring samples in the instrument coordinate system. For example, a dense raster scan would be considered a 3D type scan, while repeated cross-sections covering the same line in the transverse instrument coordinate system would be considered a 2D type scan.

Based on this definition, distinguishing 2D type from 3D type scan patterns, the requirements for the transforms are described. For 2D type scans, one displacement vector is associated with every data sample of the image in question. In the general case, this displacement vector is 3D. In the case that all input images are of 2D type with the same scan pattern, one transversal dimension can be omitted from the displacement vector, resulting in 2D displacement vectors.

From the set of 3D type datasets of the input datasets, a common set of sample positions in the motion corrected space is chosen. As one example, the positions can be chosen as a regularly spaced grid over the region of interest in the instrument coordinate system. In the special case that all 3D type datasets contain the same set of regularly spaced sample points, this set can be chosen directly. This condition can either be met because the sampling points already fit each other. This case can also occur if patterns have different areas and coverage. A different spacing of sample points might also be adapted through the preprocessing steps data sampling selection and dataset rescaling.

The transform associated with each 3D type dataset should be able to associate a 2D or 3D displacement vector, again depending on the shift invariance, to at least each sample point that was chosen in the motion corrected coordinate system. Conceptually, each of these transforms maps data from the associated dataset from its scan coordinate system to the object coordinate system.

Each of the transforms used in motion correction can be parameterized in a number of different ways. Examples include but are not limited to: Direct parameterization as a set of displacement vectors, parameterization using multi-dimensional polynomials, splines, b-splines or similar parameterized in sample time, or rigid or affine transforms in 2D and 3D. For subsets of the set of positions where the transforms should be evaluated, different parameterizations can be used than for other disjoint subsets. In general, any transform that can be evaluated at the locations specified earlier can be used for motion correction, though certain choices may produce better results.

In contrast to the way transform handling is described in the previous description, another principal way of setting up the transforms exists. In this alternative method, the transforms for the 3D type datasets are handled just the way as is the case for the 2D type sets. This has implications on other areas, mostly related to dataset similarity computation. Using this alternative approach, dataset similarity measures do always have to perform sampling on irregular grids, even when the underlying scanning patterns were on regular grids. It is understood that this alternative way of setting up the transforms can be employed by the methods and systems of described herein.

Data Interpolation

Data interpolation techniques are needed for mapping data set values into the common object coordinate system. Values for data must be generated in arbitrary positions where the data is only defined at a finite set of points. This data can, for example, be intensity data that is defined at certain coordinate points in the instrument coordinate system. Also, the time associated with each data sample is in this context considered a data value at each data sample position in the instrument coordinate system.

In general, the sampling point positions for the dataset in the instrument coordinate system for each input dataset and the associated time information as well as the selected set of sample positions in the registration coordinate system form an irregular 2D or 3D grid of data samples. On such a grid, data can be interpolated using a variety of known techniques, such as kriging interpolation or inverse distance weighting, among others. In the specific case that the sets of data point positions specify a regular 2D or 3D grid for at least a portion of the data, standard techniques, such as nearest neighbor, bi- or tri-linear, cubic or higher order spline or b-spline interpolation can be employed, among others.

Global Objective Function

The motion correction methods utilize an objective based approach that can take all available information into account at each step of an optimization scheme to estimate the previously described transforms. These objectives or goals are described in the following. An example of how to combine these objectives is also given.

Image Similarity Goal

Seen in isolation, one goal in motion correction is to find transforms such that the similarity between certain pairs of input or preprocessed datasets is maximized after application of the transforms to move the image data into the motion corrected space. Although this objective or goal is described separately in the following paragraphs, it is recognized that it must be evaluated in combination with another counterbalancing goal which takes into account motion and will be described later.

Depending on the specific dataset pair that is taken into consideration, the approach may differ. If two 3D type datasets are compared, the current transform estimates for each dataset are used to transform the image data from each image into the motion corrected space. Since the same set of data points is chosen for each 3D type dataset, this yields a set of data samples at common positions in the motion corrected space for each dataset of the pair. These transformed images can then be evaluated for similarity considering either pairs of data values from the same sampling positions or neighborhoods in space around each data point pair from the same position. Provided that the specific similarity measure applied to this information treats both sides symmetrically, the whole evaluation of the similarity between two 3D type dataset is symmetric.

In the case that a 3D type dataset is paired with a 2D type dataset, the 3D type dataset is transformed as in the previous case. Then a data interpolation step is performed for each data sample position in the 2D type dataset that samples the 3D type dataset's potentially irregular grid located in the motion corrected space at a position where each data sample from the 2D dataset is mapped into registered space. This results in a data sample to compare with each data sample from the 2D type dataset and also spatial neighborhoods that result from the sampling pattern of the 2D type dataset in the instrument coordinate system. The pairings of data samples created for comparing similarity of a 2D type dataset with a 3D type dataset are the same.

The total set of data pairs possibly including neighborhood information can then be used for similarity evaluation and maximization between the two images. Examples for similarity measures that can be used include: sum of squared differences (SSD), cross-correlation, mutual information and region mutual information, as well as other methods. Without loss of generality, the similarity measure is assumed to produce a real valued value that is greater the more similar the two datasets in question are.

In addition to similarity values that work on pairs of datasets, measures that consider more than two sets of the same type at the once can also be used. One example is of this is to penalize the variance of data set values at corresponding positions in the object space.

Image Pairing Scheme

In the case that the similarity measure that is used only supports measuring the similarity between pairs of datasets, a specific pairing scheme is used to measure certain similarities that are of interest. The simplest possible scheme is to measure all possible combinations between the available datasets. This leads to a number of measurements in the order of N*N for N different datasets.

For registering significantly more than two datasets, the cost of evaluating these measurements can be prohibitive from a computational point of view. Because of this, other schemes can be employed that pair only a subset of the available possibilities. In this context, it is favorable to prioritize pairings of datasets that have substantially complementary scan patterns over pairings of datasets with the same or similar scan patterns.

Limited Motion as Modeled by Transforms Goal

Another objective for motion correction, again seen in isolation, states that a solution to the correction problem is better if the relative motion between OCT scanner and object with respect to time during dataset acquisition as modeled by the transforms which are to be estimated is decreased by some definition. Although this objective or goal is described separately in the following paragraphs, it is recognized that it must be evaluated in combination with the previously described counterbalancing goal which takes into account similarity in the transformed state.

Recall that the transforms are defined to be evaluable at certain sampling points either in object space for 3D type datasets or in the scanning coordinate system for 2D type datasets. Associated with these sampling points is a time value. In the 2D type datasets, the time value is either directly associated when the evaluable points are the original sampling points, or it is generated through interpolating the original time structure information at the necessary positions. In the case of 3D type datasets, the time information can be generated by sampling the original time structure as given by the sampling pattern of the dataset at the coordinates of the evaluable points in the instrument coordinate system.

Since there is now approximate time information available at every point where the transforms need to be evaluated, the set of transforms can be seen as a relation that associates a displacement vector in 2D or 3D to a point in time. In this context, time means absolute time and not time within a single dataset acquisition. This is necessary to support the case of multi beam acquisition. If multi beam scanning is not performed, a relative time, for example relative to the start of each dataset acquisition, is sufficient. In general, approximate times can also be calculated when the OCT device itself does not directly provide this information from generally available information about a scan pattern and device, such as scan area, scan sampling, device acquisition rate, and others. From the reasoning of how the transforms are set up, the restriction that all transforms should produce identical displacement vectors when the time is equal follows. This restriction also allows the mapping to be treated as a 2D or 3D function in time.

Numerical approximation, for example by using a finite difference scheme, can be used to estimate the gradient of this function with respect to time. Since the transform displacement vectors model the relative position between scanner and object at a certain point in time, the gradient expresses the change in relative position and therefore the motion.

It can be assumed that both the imaging device as well as the scanned object have a non-zero mass. This implies that the relative velocity of both objects has an upper bound and that there is a physical limit to the change in relative position within a certain timeframe. Usually further assumptions can be made on the relative velocities that also restrict the expected change in relative position between scanner and object within a certain timeframe. In the case of ophthalmic imaging, eye motion from saccades can occur very rapidly and produce a discontinuous motion in time. However multiple saccades do not occur in rapid sequence and therefore the motion is within certain bounds. The purpose of the second objective which takes into account modeled motion is to assure that the transforms that are estimated are found in such a way that these facts which represent bounds on the motion are taken into consideration.

The most basic measure of the total motion during the complete data acquisition is the integration of a norm on said gradient from the start to the end of the total acquisition time. One approximate way of evaluating this integral is by summing up the resulting value of the norm application weighted by the time difference between sample points. In addition, the desired effect can be maintained for example by applying arbitrary monotonically increasing functions to the individual components of each gradient vector, applying arbitrary monotonically increasing functions to the result of the norm application and applying arbitrary monotonically increasing functions to the time difference weighting factor of each summation part.

This way, a measure can be generated, the minimization of which minimizes the motion as modeled by the transforms during the total acquisition time. Application of any monotonically decreasing function to this measure leads to a maximization problem. The resulting measure is called a regularizer value in the following sections.

Combination of Objectives

In order to be able to reach a good motion correction result, the two previously formulated objectives should not be considered in isolation. Instead, a balance should be found between the two possibly conflicting goals.

One straightforward way of doing this is the summation of the two measurements that result from the evaluation of the objectives. Other example approaches include the quotient of both measurements. In order to provide for a relative weighting between both goals, a positive factor is introduced that is multiplied with one of the measures before summation. Without loss of generality, this factor can be applied to the regularizer measure and is therefore called the regularizer weighting factor.

Figure 32:
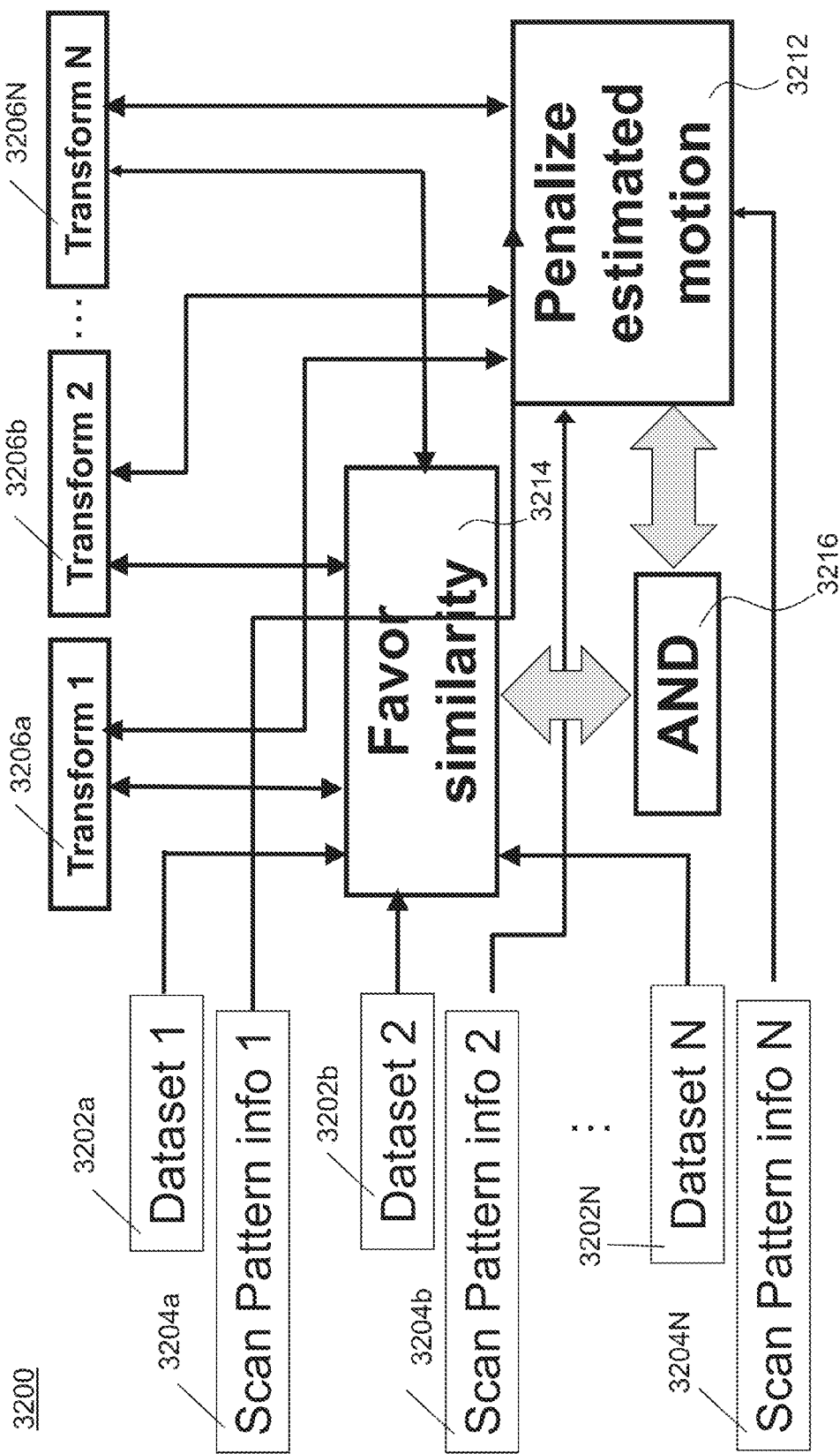
FIG. 32 is a flow chart illustrating an example embodiment of the method of evaluating an objective function by the methods of the present invention.

FIG. 32 is a flow chart showing process 3200 for evaluating an example objective function employed by the methods of the present invention. In steps 3202*a*, 3204*a* and 3206*a*, transform1, data set 1 and scan pattern 1, respectively, are taken as inputs. In steps 3202*b*, 3204*b* and 3206*b*, transform2, data set 2 and scan pattern 2, respectively, are taken as inputs. In step 3212, transform 1 and scan pattern 1 are compared with transform 2 and scan pattern 2 to penalize estimated motion between the object and the scanning instrument. In step 3214, transform 1 and data set 1 are compared with transform 2 and data set 2 to favor similarity between two transforms and two data sets. In step 3216, the objective function is evaluated by assessing the relative strengths of the motion estimation penalty and the similarity.

Process 3200 can include additional steps, operating on transforms c through N, data sets c through N and scan patterns c through N.

Referring to FIG. 32, the similarity maximization or optimization goal will read image datasets and apply the corresponding transforms to the sets. Then, similarity between interpolated sets can be evaluated and maximized. At the same time, the motion constraining or penalizing goal uses input data in the form of the sampling patterns used for the acquisition of each dataset and the current transform for each set.

Through combination of both goals, a set of transforms can be found that will accurately model relative motion during the acquisition of each dataset. The combination also implies that a compromise is made between both goals, as each goal considered alone is not likely to lead to a satisfying solution.

It is understood that the objective function can also incorporate additional goals beyond the two main objectives, as they were described. For example, another term can be used to favor spatial continuity of data values in the transformed state. This can be useful when at least one of the input datasets is a 3D type dataset with dense sampling or oversampling of a certain object area. Because of this dense sampling, the structural information of a correctly motion corrected dataset should be spatially smooth locally. In the case of raster scans, for example, high similarity between neighboring B-Scans in the transformed state can be favored. Additional terms can be incorporated into the objective function similar to how the image similarity and modeled motion goals are combined. It is understood that the methods and systems described herein can employ this and other additional goals.

Multi-Resolution Optimization

Gradient vectors of the objective function can be calculated either analytically or using an approximation technique, such as finite differences. These calculations depend on the specific choice of the transform parameterization, the dataset similarity measurement, the motion minimization goal formulation and other factors.

Based on the available information, the objective function can be optimized, that is minimized or maximized, depending on the specific objective function formulation. For performing this optimization, a variety of iterative nonlinear optimizers such as nonlinear conjugate gradients, Newtonian and pseudo-Newton techniques such as L-BFGS also known as Limited memory Broyden-Fletcher-Goldfarb-Shanno can be employed, among others. It is understood that the use of other optimization methods which do not require the evaluation of the gradient of the objective function can also be employed by the methods and devices described herein.

At the beginning of the optimization, a starting point in parameter space is chosen. One way to initialize the transforms is by starting from a point that implies that no relative motion took place during image acquisition. This implies initializing the transform in a way such that all resulting displacement vectors are assigned the zero vector. Another possibility for initialization is to use the result of a previous motion estimation that was performed with different settings. For example, the initialization could be taken by mapping the solution from an estimation process with different dataset similarity measure settings or different dataset transforms, among others. Using this framework, a motion correction result using only rigid transforms can be used to establish a rough estimate. This can improve the result of the subsequent estimation process. This process can also be performed more often than once. Another way to initialize the transforms to be computed is to employ additional data sources which are suited to provide at least a rough estimate of relative motion between object and scanner in one or more dimensions that took place during acquisition. For example, it is possible to employ a fundus camera built into the OCT device to record two dimensional images of the object being imaged. Here, relative transverse motion will cause the area which is imaged by the fundus camera to move during acquisition. These shifts in imaged area from one frame to the next can be estimated using rigid image registration techniques on sequential fundus images. These shifts can be used to initialize the transform of the simultaneously captured OCT dataset at points corresponding to a certain video frame. Since, in general, the A-Scan rate of the OCT is much higher than the video rate, data interpolation techniques can be used to interpolate displacement values in between time points corresponding to video frame time points in order to provide a completely initialized transform. This and other auxiliary motion measurement systems can help reduce processing time of motion correction and increase its accuracy because the initialization enables the method to make use of additional information about the motion. It is understood that similar initialization schemes can be used in conjunction with data sources other than video fundus cameras.

In general, nonlinear optimization on a non-convex function will only find a local optimum within a certain region of the starting position, the so-called region of attraction. One way to alleviate this problem and potentially decrease the necessary computation is to use so called multi-resolution optimization. Similar in concept to the use of a previous estimation to initialize a subsequent optimization, this embodiment operates on multiple representations of the motion estimation task. A certain number of representations with decreasing complexity are generated from an original representation that is of the desired complexity of the final result. In this context, complexity refers to the number of parameters or degrees of freedom used to describe the dataset transforms at a given level. The amount of data operated on can also be reduced by this technique.

Examples for reducing complexity include, but are not limited to, the selection of successively less common sample points in the registration coordinate system for the set of 3D type datasets. In the case of 2D type datasets, the number of data points that are used for estimation can also be successively reduced by down-sampling the datasets both in the direction that is given by the sampling time increase as well as down-sampling in axial direction in the case of spectral or swept source OCT. Along with the number of sampling points, the number of parameters used for the individual transforms, such as the use of a direct parameterization as a displacement field, can in certain cases be reduced because there are less data points where the transform has to be performed. In addition, each complexity level is allowed to possess a distinct set of configuration parameters for the motion correction optimization procedure.

One requirement for doing multi-resolution optimization is that transforms associated with the same dataset for different complexity levels, transform parameterizations and other settings should be mappable to transforms of another complexity level. The other complexity level possibly also has a different underlying transform parameterization type. One way of accomplishing this is by first transporting the transform from the input configuration to a direct parameterization at the same complexity level. This can be done by evaluating the transform at the set of points where it should be evaluable. The set of the resulting displacement vectors constitutes a direct parameterization. In the following, the direct parameterization can be mapped to a direct parameterization for the set of sampling points in the destination complexity level. This can be accomplished by treating the direct parameterization as two or three channel dataset that is attached to an in general irregular grid. By using data interpolation techniques to sample this dataset at the sampling points defined by the target complexity level, a directly parameterized approximation transform in the target complexity can be obtained. As a last step, this direct transform can be projected using, for example, a least squares approach to the target parameterization. In the concrete case, certain steps of this procedure might be unnecessary or can be combined.

The different complexity levels can be generated beforehand or the necessary sub-data can be computed on demand. A typical multi-resolution procedure then proceeds as follows. Given an initialization set of transforms, the set is mapped to the lowest complexity level. Then, iterative numerical optimization is performed on the lowest complexity level with one of the previously described technique or other techniques. Typically, a certain maximum number of iterations are specified for the optimization after which the last parameter set is used as a result. Alternatively, the optimization may stop before this. For example, when the objective function values or the value resulting from application of a monotonically increasing function to a certain norm on the gradient vector of the objective function do not change significantly anymore from one iteration to the next. Other termination criteria can also be applied. After the optimization on the current level has finished, the resulting transforms are mapped to the complexity and parameterization of the corresponding transforms of the next chosen level. Typically the next level chosen is the one with next higher complexity. However, a solution for a more complex level can also be mapped to the initialization of less complex level again. This process can be repeated multiple times until a solution for the original problem complexity has been reached.

Solution Correction Step

An optional processing step that can be performed is a solution correction step. It can be applied after every numerical optimization iteration, and/or after certain multi-resolution levels have completed optimizing, and/or after the final transform for a given set of input datasets and configuration settings has been found. In general, the solution to the motion correction problem as described in previous sections has three degrees of freedom built in. The degrees of freedom can be modeled as a variable translational part that is common to all transforms and therefore can shift all dataset data samples by a fixed amount in object space. This effect does typically not express very strongly, with the translational vector being close to the zero vector. Still, this effect can be undesired. In this case, the parameters of each transform can be corrected at certain points during the motion correction step so that the resulting common translational part of all transforms is the zero vector. One way of performing this is by calculating the mean translational part over all transforms and updating the parameters of each transform such that this mean component is removed.

Application of Solution Transforms

Once the motion estimation process has found a solution, a final set of datasets in registered space can be generated. This involves application of the transforms to each dataset. In general this data does not have to be the same data that was used for the motion estimation process itself. For example, intensity information or other structural data would preferably be used for assessing similarity in the transformed state. Instead the transforms can also be applied to different data channels calculated from the same dataset acquisition. Such data can include, but is not limited to, different precision representations of intensity data in linear, logarithmic and other scales. The transforms can also be applied to functional imaging information, such as phase shift information obtained by performing Doppler OCT, among others. These are examples of data sets which are derived from the OCT data. Derivative datasets may contain a different set of data channels and the data may have been processed differently from the input datasets.

The application of the transform can be done in the same way as used during the evaluation of the objective function values. Alternatively, a different data interpolation technique may be used. The result is a registered dataset from each input dataset that is located on an in general irregular grid in motion corrected space. In the case of 3D type image data, the set of sampling point positions of the datasets that exist in object space are the same for each dataset.

Description of Data Combination (Merging) for Image Enhancement

After motion correction and application of the resulting transforms to the data channel of interest, a set of datasets are obtained that exist in the same motion corrected space. In the case of 3D type datasets, these sets are also defined at common sampling point positions. Provided that motion correction is performed well, the corresponding data samples from each dataset contain imaging data from the same location of the object.

Depending on the specific type of imaging data, such as intensity information, that is used, it is often desirable to try to combine these registered datasets into a single dataset. For example, this is the case when using OCT intensity data, where the combination will produce better image quality because noise can be reduced. Another example is Doppler OCT phase shift data that can be used for measuring blood flow. Combining multiple samples acquired at different times from the same position can also lead to reduced noise levels. When measuring blood flow using Doppler data, pulsatility can be reduced when combining multiple velocity measurements from different points in time. This allows the generation of a blood flow measure that better approximates a measure, such as flow per minute, which is less dependent on short time effects induced by the pulse.

A natural way to produce a combined dataset is to simply average the data from corresponding sampling point positions. The calculations of variance type measures can also be interesting, for example, in the case of Doppler OCT data. However motion induced distortion can lead to the fact that some areas which are present in one source dataset might not be sampled at all in the other set. If this is the case, averaging is not a good approach because the data from the dataset where the certain area was not present will be filled with substitute data from neighboring areas. Instead, it is possible to employ a technique that mainly uses the data from the dataset where the area was actually present for the merged volume in this case.

Instead of averaging available data samples from each position to produce a final dataset, convex weighted sums of the registered data samples are used to combine the data. In this scheme, each sample of the different data sets at a particular position has a positive real value associated with it. Furthermore, the sum of these weights over all images should be one, with none of the weights being smaller than zero, in order to form a convex combination. Other combination schemes can also be used.

The basic idea to generate the weights comes from the fact that when a certain area is not present in a dataset denoted A, while it is present in dataset B, another area in the original A set will be taken as a substitute so that this substitute area in the original set will be sampled more than once when the registration result of A is generated. In contrast, the original area from B is likely to be only sampled once.

Figure 33:
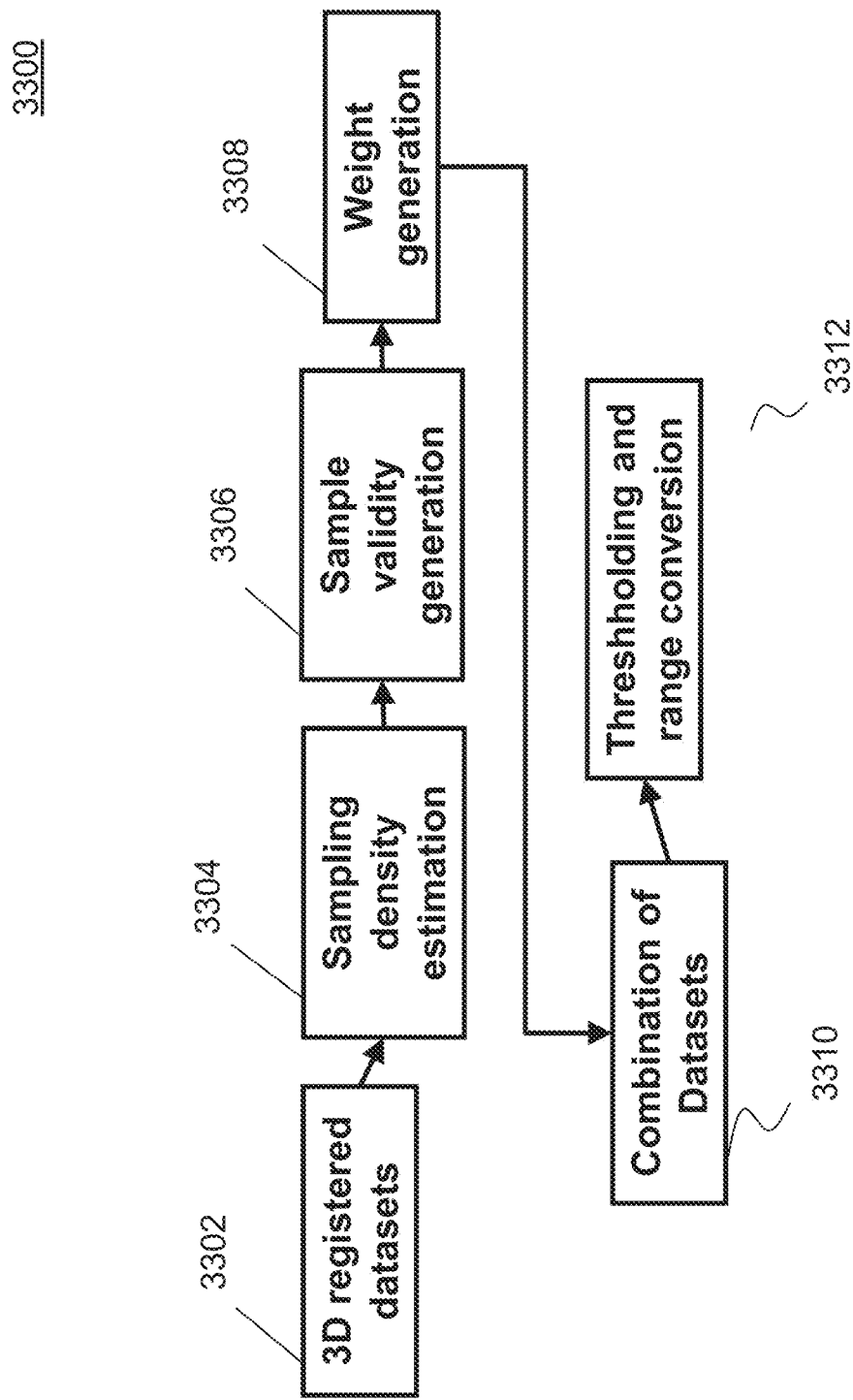
FIG. 33 is a flow chart illustrating an example embodiment of an image combination procedure employed by the methods of the present invention.

FIG. 33 shows an exemplary embodiment of the process 3300 of merging data sets according to the methods described herein. Method 3300 can be executed by, for example, computer 102 of device 100 shown in FIG. 1 or computer 202 of device 200 shown in FIG. 2.

Estimation of Sampling Densities

In order to produce weights, the sampling density is estimated in the original datasets, which represents how often a certain area in the original set was sampled to produce the corresponding registration result.

One way of estimating sampling density for each data sample of a particular dataset consists of a two-step process. First, a so called Parzen estimation step is performed that estimates the density of sampling points for generating the registered result in the original scan coordinate system of each data set. Other techniques for estimating this density can also be used. In the second step, the generated density is sampled as the original dataset was sampled in order to generate the registered set. The resulting value relates to how often the particular area that was sampled to generate a particular sample in the registered dataset was used in total when generating the whole registered set. When this value is higher for a sample from one registered dataset than for the same sample from another set the former sample is assumed to more likely have been used to fill up a hole in the sampling of the former dataset. Subsequently, this is used in the actual weight generation.

Generation of Sample Validity Value

Another source of information that is used to generate the weights is called sample validity. In dataset interpolation, multiple samples are taken into consideration when generating the interpolated result. If some or all of the samples of this footprint are outside the actual volume data as defined by the grid of data points, the validity of the sample is considered to be lower than if all samples were inside the volume. A value is associated to every data sample which is defined to be one if the sample is completely inside the respective source grid and zero if it is outside. If a sample is considered to be partially outside the original sample grid, a value in between 1 and 0 should be assigned. The more the sample is considered outside, the lower this validity value. It is also recognized that other methods can be used to assess sample validity for data set interpolation.

Computation and Application of Weighting Factors

For computation of the final weights used to combine the datasets, each set of samples from the different registered datasets can be considered independently. The weights can be calculated in such a way that when there is no difference in the sampling density and sample validity among the considered samples the embodiment assigns equal weights to each sample. So for N samples, each weight is set to 1/N.

In the general case that there are differences in these values, the following rules apply. If one sample has more than equal share of sampling density, its weight should be lower than equal distribution. Also if a sample has lower sample validity, its weight will also be lower. In total, however, the weights still should add up to one and none of them should be negative.

This way when there is no difference between samples with regard to these measures, equal weights will lead to an averaging effect that reduces noise. If individual samples have been more likely used to fill gaps in a dataset or were sampled from outside of the source dataset to a larger degree with respect to the other samples, their assigned weight will be lower. This leads to the relative or complete exclusion of this sample in the production of the final combined result, therefore possibly removing artifacts.

The final construction of the combined image is then the weighted summation of corresponding data samples. In addition to this, data may also be normalized before the summation to compensate, for example, for differences in brightness when using intensity data.

Additional logic appropriate to the content of the combined data, such as intensity information as opposed to, for example, Doppler shift values, can be incorporated in the weight generation process. For example, when merging Doppler shift data, it makes sense to transform the phase shifts into the complex domain, in which the weighted sum can be performed, and then to transform back to a phase shift. Also the weight generation process can be adapted to handle special imaging scenarios such as blinking during dataset acquisition of the eye. For example, blinking could be detected by looking at an axial sum of intensity values and assigning lower weights to a sample if the axial projection is very dark because when a blink occurs, the A-Scans captured during the blink will not show any structure, and therefore be dark. It is understood that the methods and devices described herein can also employ the simple combination of data values without using sampling density and sample validity. One example would be to average data values. Also, additional properties of the datasets themselves or of the transforms that were used to generate the registered data sets may be used in the combination process.

Noise Reduction

In addition to the noise reduction effect that is achieved by the averaging effects of the weighted sum combination, additional noise reduction techniques can optionally be employed. These can either be applied to individual registered data sets, or to the final combined dataset. In addition, complex noise reduction techniques can be employed that analyze dependencies and correlations between data samples and neighborhoods around them to achieve better noise reduction effects.

Thresholding and Range Conversion

Depending on the output format of the final combined and registered dataset, a conversion between the data format used for the intermediate calculations and the final output data format may be needed. In the example of mapping to an integral data type, a min/max mapping can be performed to adapt the data range of the floating point data to the output format.

Independently of this, a thresholding operation can be performed on the data to remove outliers at both ends of the data range.

Multi-Spot Scanning Apparatus

Traditional OCT instruments image with a single OCT beam and one spot, as shown in FIG. 1 and FIG. 2. The figures illustrate an apparatus for ophthalmic OCT imaging, however, it is recognized that the concepts in the section can be applied to other OCT imaging applications. As one example, an effective increase in imaging speed can be obtained by using multiple OCT beams and multiple spots on the object tissue and performing the image acquisition in parallel. FIG. 34A shows an apparatus that projects two spots on the retina by placing two fiber ends in, or near, the focal plane of the collimating lens.

Alternatively, two separate fibers and collimators could be used and arranged such that the axes of the collimated light beams are non-parallel. Light from the collimator(s) reflects off a two axis beam steering mechanism into the patient interface optics. Beam steering can be performed with a single dual-axis mirror, multiple single axis steering mirrors (e.g. galvanometers), piezo steering elements, or electromagnetic steering elements, etc. Multiple spot arrangements are possible. FIG. 34B shows a raster scan using two imaging spots with the fast scan in the y direction, called YFast. FIG. 34C shows a raster scan using two imaging spots with the fast scan in the x direction, called XFast. In the specific example shown in FIG. 34B and FIG. 34C, the spots are offset at a 45 degree angle to the X and Y scanning directions. With this spot arrangement, XFast data sets can be obtained, YFast data sets can be obtained, and/or other scan patterns can be executed and associated data obtained. During imaging, light back-reflected or backscattered from the object tissue returns to the fiber and proceeds to an interferometer with a separate imaging or detection channel for each OCT beam. In one approach, the spot movements are coupled such that both spots move in the same scan pattern. Multiple sequential data sets can be obtained with the advantage that the total imaging time required per volume is reduced. A second advantage is that the motion affecting both data sets is correlated. Incorporating the motion correlation information into the registration routines improves convergence speeds and accuracy of registration. This concept can be generalized to image with more than two spots.

Figure 35A:
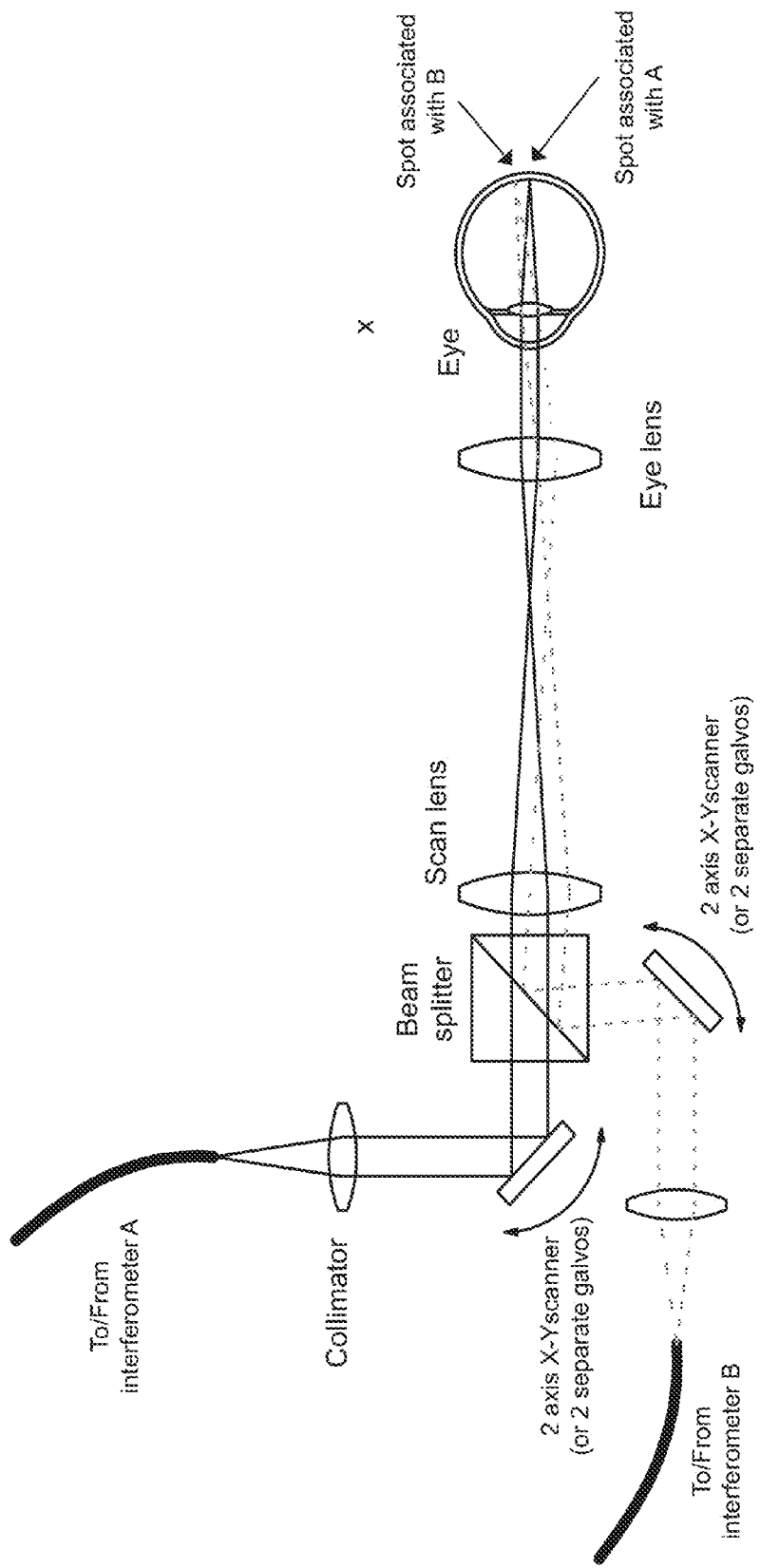
FIG. 35A is a schematic diagram of a two-spot scanning apparatus with independent scan motion that can be used to practice the methods of the present invention.

FIG. 35A shows an imaging apparatus that is capable of scanning two independently controllable beams and projecting two spots on the tissue object.

A beam splitter or similar multiplexing device is placed in the optical path such that light from two or more independently controllable beam steering mechanisms can be combined in the patient interface. Light from a first interferometer (A) is collimated by a first collimator and reflects off a first beam steering mechanism into the patient interface optics through a beam splitter or similar beam combining device. Beam steering can be performed with a single dual axis mirror, multiple single axis steering mirrors (e.g. galvanometers), piezo steering elements, or electromagnetic steering elements, etc. Light from a second interferometer (B) is collimated by a second collimator and reflects of a second beam steering mechanism into the patient interface optics through the before mentioned beam splitter or similar beam combining device. It is recognized that the interferometers may share subsystems such as the light source, provided that they enable independent detection of OCT data from the two spots.

Each spot position on the tissue can be independently controlled to execute a scan pattern. Compared to the a single spot scanning OCT system or the coupled motion multi-spot scanning apparatus, this independently controlled multi-beam, multi-spot scanning approach enables the simultaneous acquisition of two independently scanned datasets in parallel. FIG. 35B shows an example scan pattern that acquires a YFast data set with spot A and an XFast data set with spot B. One advantage is that only one image acquisition has to be performed to obtain two complementary datasets. A second advantage is that the motion affecting both datasets is correlated. Incorporating the motion correlation information into the registration routines improves convergence speeds and accuracy of motion correction. A third advantage of the independently controlled multi-spot scanning apparatus is that the object tissue position between datasets should be more similar than if separate datasets were obtained in sequence, improving convergence and final registration results. This concept can be generalized to image with more than two beam and two spots.

The multi-beam scanning approaches described are synergistic and complementary to the data processing and motion correction described above. However, the data processing and motion correction described above can be practiced separately from the multi-beam scanning. Similarly, the multi-beam scanning can be practiced separately from the data processing, motion correcting, and merging methods as described above.

Accordingly, an example embodiment of the present invention is a method of processing data sets. The method comprises computing, based on a value of an objective function, one or more three-dimensional transforms, each associated with a respective three-dimensional data set, said three-dimensional data sets representing at least partially overlapping regions of an object. Computing includes evaluating the objective function by (a) calculating similarity between (i) two or more three-dimensional data sets in a transformed state, or (ii) two or more preprocessed three-dimensional data sets in the transformed state, and (b) estimating motion of the object relative to an imaging instrument. The method further includes applying at least one three-dimensional transform to its respective three-dimensional data set or to a derivative three-dimensional data set corresponding to the respective three-dimensional data set to obtain at least one motion-corrected data set.

In one example embodiment, evaluating the objective function includes favoring similarity between either (i) the two or more three-dimensional data sets in the transformed state or (ii) the two or more preprocessed three-dimensional data sets in the transformed state.

In another example embodiment, each three-dimensional data set is a set of values of a signal acquired from a region of the object, and wherein favoring similarity between the two or more three-dimensional data sets in the transformed state includes penalizing differences among signal values.

In another example embodiment, evaluating the objective function includes penalizing motion of the object relative to an imaging instrument.

In another example embodiment, computing includes first and second three-dimensional transforms, and wherein said applying comprises applying the first three-dimensional transform to the first three-dimensional data set and applying the second three-dimensional transform to a second three-dimensional data set to obtain first and second motion-corrected data sets, respectively, and further combining data elements of the first and second motion-corrected data sets to obtain a merged motion-corrected data set having improved signal quality relative to the first or second motion-corrected data sets, individually.

In another example embodiment, combining data elements further includes adjusting contributions of data elements of the first and second motion-corrected data sets to the merged motion-corrected data set based on at least one property of the first and the second three-dimensional transforms.

In another example embodiment, the at least one property of the first or the second three-dimensional transform is sampling density.

In another example embodiment, adjusting contributions further includes computing a weighted sum of the data elements of the first and second motion-corrected data sets.

In another example embodiment, the method further includes acquiring a first three-dimensional data set using a first scan pattern and acquiring a second three-dimensional data set using a second scan pattern, wherein the first and the second scan patterns are complementary.

In another example embodiment, the complementary scan patterns are raster scans.

In another example embodiment, the raster scans are orthogonal.

In another example embodiment, the method further comprises iteratively computing the one or more three-dimensional transforms.

In another example embodiment, the method further comprises computing the one or more three-dimensional transforms using numerical optimization methods on said objective function.

In another example embodiment, the method further comprises computing the one or more three-dimensional transforms are computed using multi-resolution numerical optimization methods.

In another example embodiment, the object is selected from the group consisting of the eye, retina, fovea, optic nerve head, or cornea.

In another example embodiment, the method further includes obtaining a first motion-corrected data set associated with a first time point, obtaining a second motion-corrected data set associated with a second time point, and comparing the first and the second motion-corrected data sets to track changes quantitatively between the first and the second time points.

The object can be associated with a patient.

In another example embodiment, the first and the second time points correspond to the first and the second visits by the patient to a healthcare provider, respectively. In another example embodiment, the first and the second time points correspond to the first and the second activities by the patient for scanning the object, respectively.

An example of such activities by the patient can be performing the same or similar activities to those of a healthcare provider. Such activities can be performed at home. The scanning equipment can be the same as that used by a healthcare provider or patient-operated equipment adapted for home use. For example, a scanner can be operably connected to a desktop or laptop computer or even integrated into or connected to a handheld device. One example of such handheld device is a mobile phone.

In another example embodiment, the three-dimensional data set is captured via A-scans and further wherein the one or more three-dimensional transforms are associations of a three-dimensional displacement with each A-scan.

In another example embodiment, the method further comprises preprocessing the three-dimensional data set by a method selected from the group consisting of image resampling, noise reduction, A-scan feature generation, tilt-compensation, and roll-off compensation.

The three-dimensional data set can include at least one of intensity data, Doppler shift data, or polarization data.

In another example embodiment, the derivative three-dimensional data set includes at least one of Doppler shift data, or polarization data.

Another example embodiment of the present invention is a system comprising modules configured to perform the steps of the methods disclosed herein.

Another example embodiment of the present invention is a non-transitory computer-readable medium having thereon a sequence of instructions, which, when executed by a processor, cause the processor to compute, based on a value of an objective function, one or more three-dimensional transforms, each associated with a respective three-dimensional data set, said three-dimensional data sets representing at least partially overlapping regions of an object, wherein the instructions that cause the processor to compute the one or more three-dimensional transforms include instructions to cause the processor to evaluate the objective function by:
(a) calculating similarity between (i) two or more three-dimensional data sets in the transformed state, or (ii) two or more preprocessed three-dimensional data sets in the transformed state, and
(b) estimating motion of the object relative to an imaging instrument.

The sequence of instructions, when executed by a processor, cause further the processor to apply at least one three-dimensional transform to the respective three-dimensional data set or to a derivative three-dimensional data set to obtain at least one motion-corrected data set.

Another example embodiment of the present invention is a method of processing OCT data sets. The method comprises acquiring two or more three-dimensional OCT data sets representing at least partially overlapping regions of an object, wherein at least one data set is acquired using a scan pattern complementary with respect to a scan pattern of at least one other data set, and computing a three-dimensional transform for each data set using an objective function. The objected function
(a) favors computed similarity between the three-dimensional data sets in the transformed state, and (b) penalizing motion of the object relative to an imaging instrument. The method further includes applying at least one three-dimensional transform to its respective data set to obtain at least one motion-corrected data set.

In another example embodiment, the similarity is computed based on at least one of intensity data, amplitude data, phase data, or polarization data.

In another example embodiment, the data used to compute similarity is preprocessed using noise suppression, tilt compensation, OCT signal roll-off correction, data reduction, data normalization, or a combination thereof.

In another example embodiment, the three-dimensional transform is applied to its respective three-dimensional data set by transforming at least one of intensity data, amplitude data, phase data, or polarization data.

In another example embodiment, favoring the computed similarity between the three-dimensional data sets in the transformed state includes penalizing differences between data values selected from the three-dimensional data sets in the transformed state.

In another example embodiment, penalizing the differences between data values includes using the sum of squared differences, variance, sum of absolute values of differences, or a combination thereof.

In another example embodiment, a first three-dimensional transform is applied to a first three-dimensional data set and a second three-dimensional transform is applied to a second three-dimensional data set to obtain first and second motion-corrected data sets, respectively. The method further includes merging the first and the second motion-corrected data sets by combining data elements from the first and second motion-corrected data sets to obtain a merged motion-corrected data set with improved signal quality relative to the first or second motion-corrected data sets individually.

In another example embodiment, the first and the second three-dimensional transforms have properties, and wherein merging the first and the second motion-corrected data sets further includes adjusting contributions of data elements to the merged motion-corrected data set based on at least one property of the first and the second three-dimensional transforms. The at least one property of the first or the second three-dimensional transforms can include sampling density.

In another example embodiment, merging the first and the second motion-corrected data sets includes computing a weighted sum of the data elements of the first and second motion-corrected data sets.

In another example embodiment, the complementary scan patterns are raster scans. The raster scans can be orthogonal.

In another example embodiment, the method further includes iteratively computing the three-dimensional transforms.

In another example embodiment, the method further includes computing the three-dimensional transforms using multi-resolution numerical optimization methods. In another example embodiment, the object is selected from the group consisting of the eye, retina, fovea, optic nerve head, and cornea.

In another example embodiment, at least a first and second data set from a first time point are processed to obtain a first motion-corrected data set associated with the first time point, and at least a third and fourth data set from a second time point are processed to obtain a second motion-corrected data set associated with the second time point; and wherein the method further comprises comparing the motion-corrected data sets or measurements from the motion-corrected data sets to track changes quantitatively over multiple time points.

In another example embodiment, the three-dimensional data sets include A-scans, and further wherein each three-dimensional data set contains a set of data channels, the data channels including at least one of: intensity, amplitude, phase, Doppler shift, or polarization signals, the method further including associating said set of data channels with each A-scan from the OCT data set.

In another example embodiment, the three-dimensional data sets include A-scans and further wherein the three-dimensional transforms are associations of a three-dimensional displacement with each A-scan.

EXEMPLIFICATION

Example 1

Two complementary OCT volumes of the optic nerve head in a human retina were acquired, registered, and merged as shown in FIG. 16A through FIG. 16C. FIGS. 16A and 16B each shows an illustration of a three-dimensional OCT image of the same volume obtained using two orthogonal scan directions. FIG. 16C shows the result of merging the two images using an example embodiment of the method described herein.

A prototype spectral/Fourier domain OCT system with 101 kHz axial scan rate was used to acquire volumes over a region of 6×6 mm with 400×400 axial scans in the transverse directions. Each volume was acquired in approximately two seconds. The first volumetric data set was acquired using a raster scan with the fast scan in the x direction, labeled XFast. The second volumetric data set was acquired using a raster scan with the fast scan in the y direction, labeled YFast. Both the first and second volumetric data sets were acquired in substantially the same region of the retina, but were distorted in both the axial and transverse directions due to eye motion occurring during the acquisition. Application of an example embodiment yielded a final merged data set that had been motion corrected and represents the true undistorted retinal morphology. The processing time applied to this data set was approximately three minutes using graphics card (ATI Radeon 5850) accelerated code on a standard desktop computer. Current commercial OCT systems used in ophthalmic imaging have axial scan rates of 25 to 50 kHz and acquire data sets consisting of 200×200 axial scans in the transverse directions. Therefore processing times will be faster on these smaller data sets. In addition, processing times are expected to increase rapidly with developments in graphic card and computer technology.

Figure 17C:
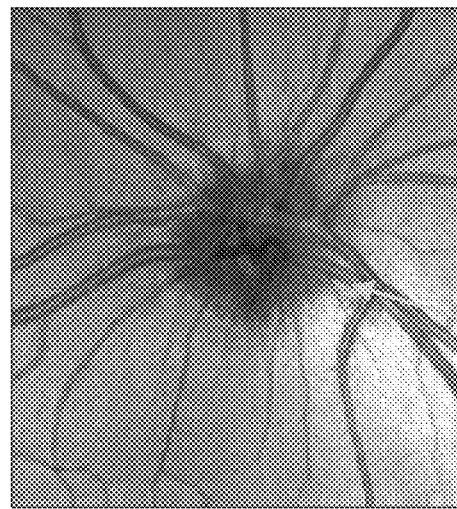
FIGS. 17A through 17C are illustrations of motion correction and data gap filling: panel A is an OCT fundus image of a first 6×6 mm volumetric data set; panel B is an OCT fundus image of a second 6×6 mm volumetric data set; panel C is an OCT fundus image of a merged, motion corrected and data-gap filled volumetric data set.
Figure 17B:
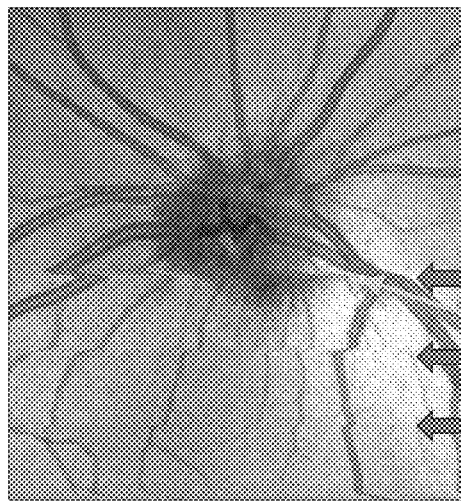
Figure 17A:
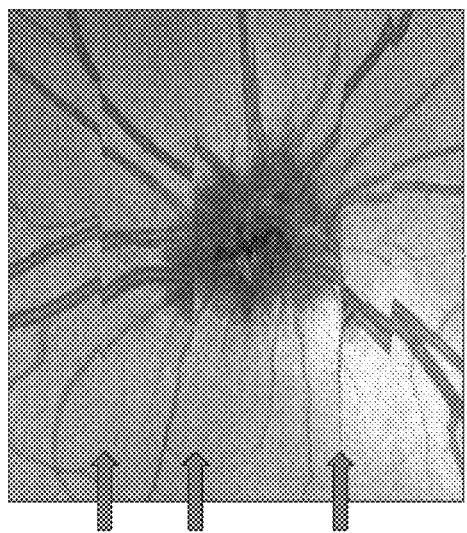

FIG. 17A through 17C illustrate the results of applying the methods described herein. Specifically, FIG. 17A and FIG. 17B each show an OCT fundus views from two volumetric OCT data sets obtained scanning in orthogonal directions. FIG. 17C shows the result of merging the two OCT images according to example methods described herein. The OCT fundus view was generated by summing the axial intensities along each A-scan for each transverse pixel in the image. A prototype spectral/Fourier domain OCT system with 101 kHz axial scan rate was used to acquire volumes over a region of 6×6 mm with 400×400 axial scans in the transverse directions. Each volume was acquired in approximately two seconds. The first volumetric data set was acquired using a raster scan with the fast scan in the x direction (XFast scan) and is shown in FIG. 17A. Motion artifacts due to eye and head motion are visible as horizontal discontinuities in the dataset. The second volumetric dataset was acquired using a raster scan with the fast scan in the y direction (YFast scan) and is shown in FIG. 17B. Motion artifacts due to eye and head motion are visible as vertical discontinuities in the data set. Application of motion compensation yielded a final merged dataset that was motion-corrected. The OCT fundus view generated from the motion corrected dataset is shown in FIG. 17C and represents the true undistorted retinal structure. Gaps in the data present in the original uncorrected input data sets were filled in the registered and merged dataset as long as the data was present in at least one of the input datasets. Finally, because eye motion can be more pronounced for hand held OCT imaging instruments, the example embodiments described herein can be used with a hand held OCT instrument in order to correct for motion distortion, register data sets, and merge multiple datasets.

Figure 18C:
FIGS. 18A through 18C are illustrations of arbitrary cross sectional image extraction and improved signal-to-noise: panel A is a first OCT cross sectional image extracted from a first three dimensional data set; panel B is a second OCT cross sectional image extracted from a second three dimensional data set; panel C is an OCT cross sectional image extracted from a registered and merged three dimensional data set.
Figure 18B:
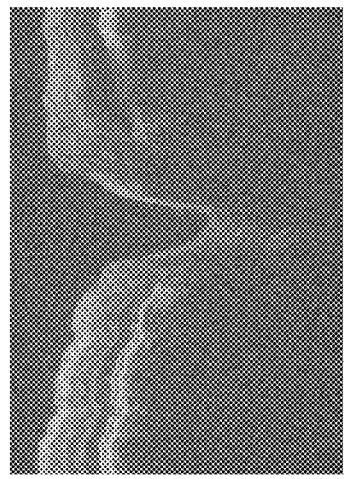
Figure 18A:

FIG. 18A through FIG. 18C show two-dimensional (2D) cross-sectional images that were extracted from a three-dimensional (3D) OCT volume. A 2D image extracted along the slow axis scan direction of a 3D OCT volume (FIG. 18A) that was acquired with the fast scan in the x direction is shown in FIG. 18A. Significant eye motion during the acquisition produced distortion of the retinal structure in the resulting 2D image. A 2D structural image extracted along the slow axis scan direction of a 3D OCT volume (FIG. 18B) that was acquired with the fast scan in the y direction is shown in FIG. 18B. FIG. 18C shows the result of merging the two images according to example methods described herein.

Significant eye motion during the acquisition produced distortion of the retinal structure in the resulting 2D image. By registering and merging intensity data from the first (FIG. 18A) and second (FIG. 18B) data sets, a registered and merged 3D data set was generated. A 2D cross-sectional structural image extracted from the registered and merged 3D data set is shown in FIG. 18C. In addition to showing eye motion corrected retinal morphology, the 2D cross-sectional image extracted from the registered and merged 3D data set showed improved contrast and signal to noise. The random speckle noise of the input volumes was also reduced.

Figure 19A:
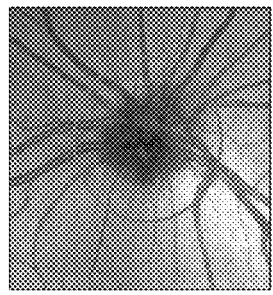
FIGS. 19A through 19C are illustrations of a virtual circular scan extraction from a 6×6 mm 3D-OCT volume: panel A is an image of a region around an optic nerve head; panel B is a first circular cross sectional image extracted from a first three dimensional volume; panel C is a second circular cross sectional image extracted from a second three dimensional volume; panel D is a circular cross sectional image extracted from a registered and merged three dimensional volume.
Figure 19D:
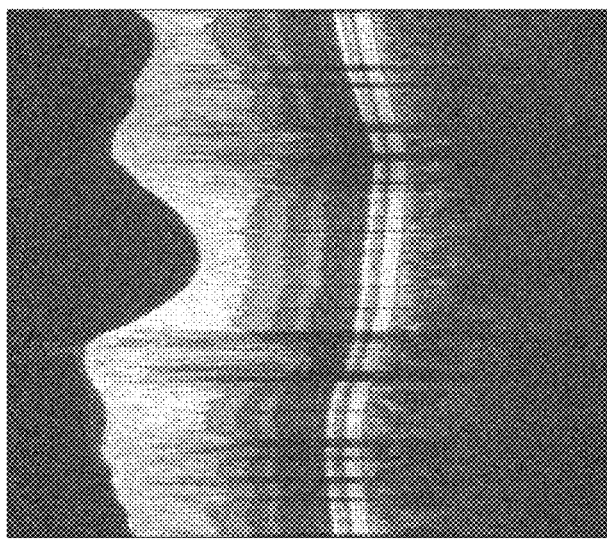
Figure 19C:
Figure 19B:
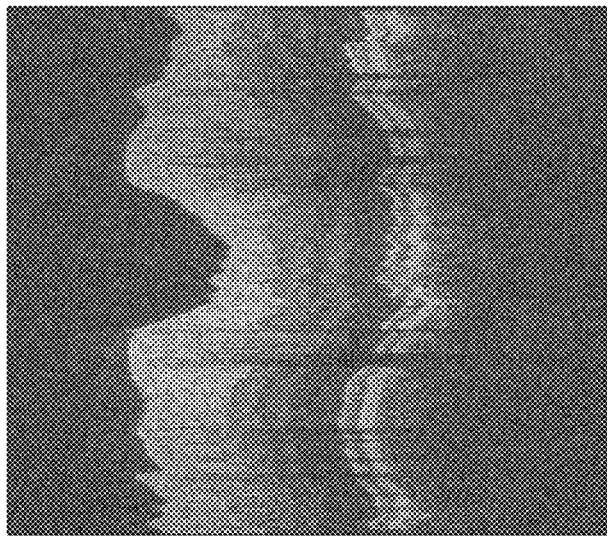

2D cross-sectional images can be extracted from a 3D OCT volume along curved scan trajectories. FIG. 19B through FIG. 19D show 2D data sets extracted along a circular trajectory shown in FIG. 19A. FIG. 19A shows a circle drawn around the optic nerve head in the upper right OCT fundus image.

FIG. 19A and FIG. 19B show 2D circular image obtained by scanning in orthogonal direction. FIG. 19D shows the resulting merged image obtained according to example methods described herein.

Before motion correction and registration, the eye motion distorted the retinal morphology and introduces discontinuities, as shown in the images on the left and middle, which show 2D circular data extractions from a first 3D OCT volume obtained with the fast scan direction in the x direction and a second 3D OCT volume obtained with the fast scan direction in the y direction, respectively. As shown in FIG. 19D, the 2D data set extracted from the motion corrected and merged 3D OCT data set showed continuity of data, motion correction, and improved contrast and signal to noise. In ophthalmic diagnosis and management of glaucoma, a circular scan around the optic nerve head, a so-called circumpapillary scan, is a standard OCT scan pattern. As can be seen in FIG. 19A through FIG. 19D, the virtual circular scan image quality was enhanced by the multiple volume registration and merging process. The virtual scan was compensated for motion distortion in three dimensions and had improved signal, lower speckle noise and improved continuity of layers. This improvement in image quality would further improve the performance of automated registration, which was used to determine the position of the circumpapillary scan for automatic extraction from the volumetric dataset. Registered and combined datasets can also be processed using automatic morphometry analysis such as segmentation which identifies and quantitatively measures retinal layers, such as the nerve fiber layer. Improvements in dataset quality will improve the reproducibility of automated segmentation and other morphometric measurements. Example embodiments combined with quantitative measurement of features such as lesion structure and size, including lesions such as drusen, subretinal fluid or choroidal neovascular membranes can be used for the diagnosis and monitoring of disease progression in age related macular degeneration or diabetic retinopathy.

Figure 20:
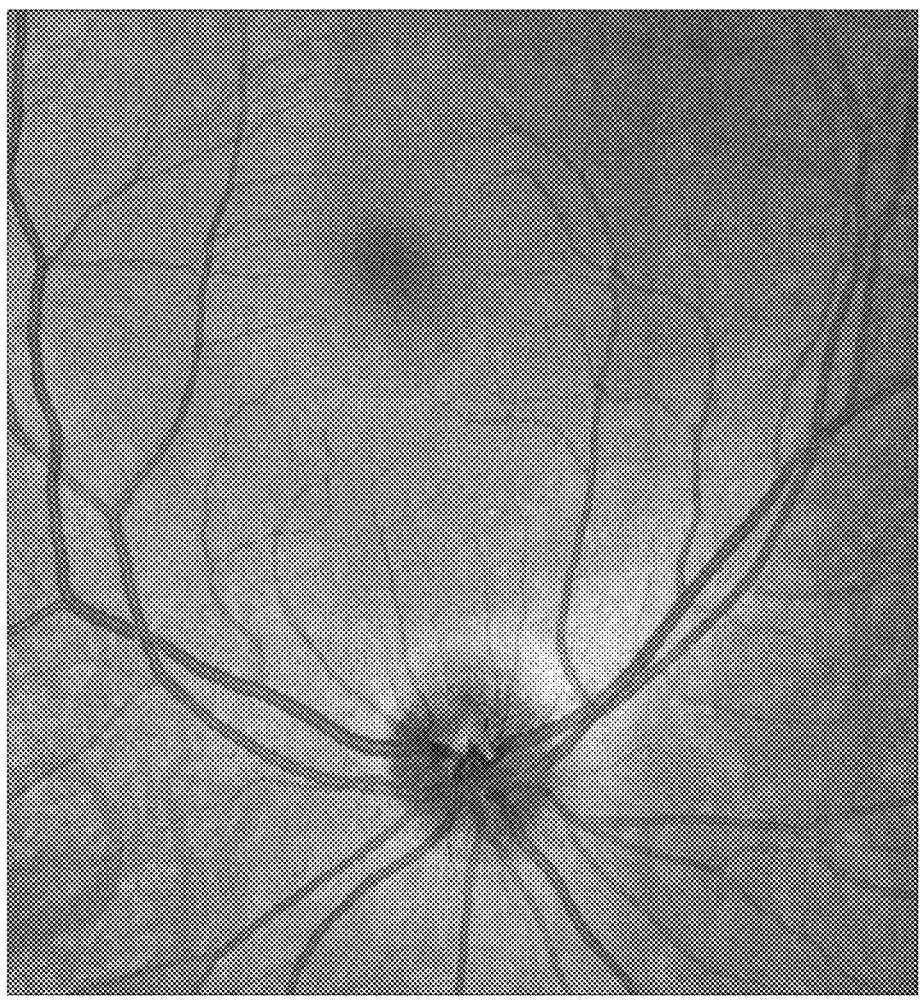
FIG. 20 is an OCT fundus image of a wide field of view (12×12 mm) three dimensional data set.
Figure 21C:
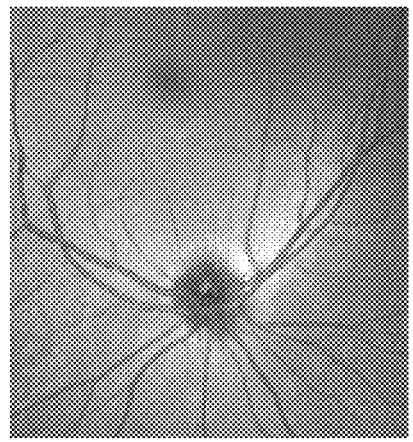
FIGS. 21A through 21C are illustrations of gap filling of missing data due to blinking during image acquisition: panel A is an OCT fundus image from a first three dimensional data set, panel B is a second OCT fundus image from a second three dimensional data set, panel C is an OCT fundus image of the three dimensional data set resulting from registering and merging the first and the second volumetric data sets.
Figure 21B:
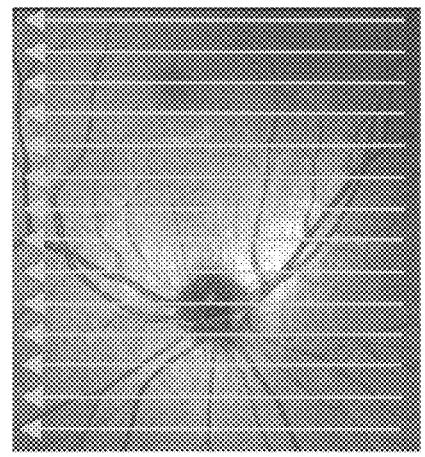
Figure 21A:
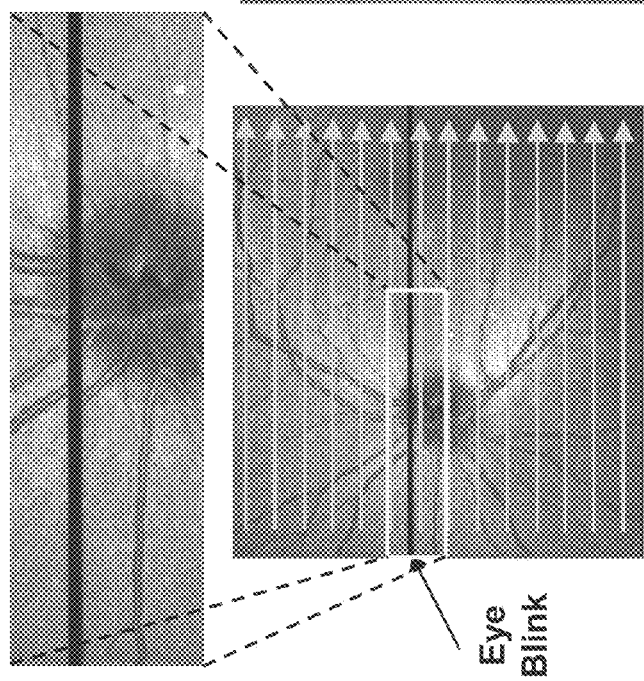

A large data set of the human retina spanning 12 mm×12 mm with 1100×1100 transverse pixels is shown in FIG. 20. A 200 kHz axial scan rate swept source/Fourier domain OCT imaging system operating at 1050 nm and with approximately 5 μm axial resolution was used to obtain multiple 3D OCT volumetric data sets. The acquisition time of approximately 6.4 seconds was longer than typically used in ophthalmic applications because eye movement and blinking limit acquisition times. As shown in FIG. 21A, a first 3D data set obtained by raster scanning with the fast scan in the x direction showed an eye blinking event occurring during the acquisition. The eye blink manifested itself as a long dark region associated with a gap in the retinal data in the OCT fundus image. As shown in FIG. 21B, a second 3D data set obtained by raster scanning with the fast scan in the y direction showed small image distortions. As shown in FIG. 21C, application of an example embodiment yielded a motion corrected volume, such that the gap associated with the first volume (XFast raster) in the retinal image was filled with data from the second volume with complementary scan pattern (YFast raster) to produce an appropriately reconstructed and motion corrected data set. Example embodiments enabled the acquisition of larger data sets and the use of longer acquisition times than previously possible by compensating for motion distortion effects as well as missing data or gaps in datasets.

It is also possible to register and merge more than two data sets using an example embodiment. FIG. 22A shows a 2D cross sectional image extracted from a 12 mm×12 mm 3D OCT data set with 1100×1100 axial scans in the transverse direction. Significant eye motion and dataset discontinuities can be seen in the example of the uncorrected OCT fundus image. A total of six volumes, consisting of three XFast and three YFast raster scan patterns, were acquired in sequence. Application of an example embodiment produced a motion corrected and merged 3D data set incorporating information from all six data sets simultaneously. FIG. 22B shows a 2D cross sectional image extracted from the motion corrected and merged. The resulting image showed the true retinal contour, fills in gaps in the data, and demonstrates significantly improved contrast and signal to noise. The processing time for these datasets was 90 minutes using a graphics card (GPU). The OCT fundus image of the dataset shows that comprehensive structural information covering both the optic nerve head and the fovea can be provided with one merged volume.

Results described above show that it is possible to extract a 2D image from a 3D data set along an arbitrary trajectory and with potentially arbitrary orientation. In addition to extracting a 2D image, 3D data subsets can also be extracted from a larger volume. It is sometimes useful to define the region to be extracted based on a feature contained within the data set.

Figure 23:
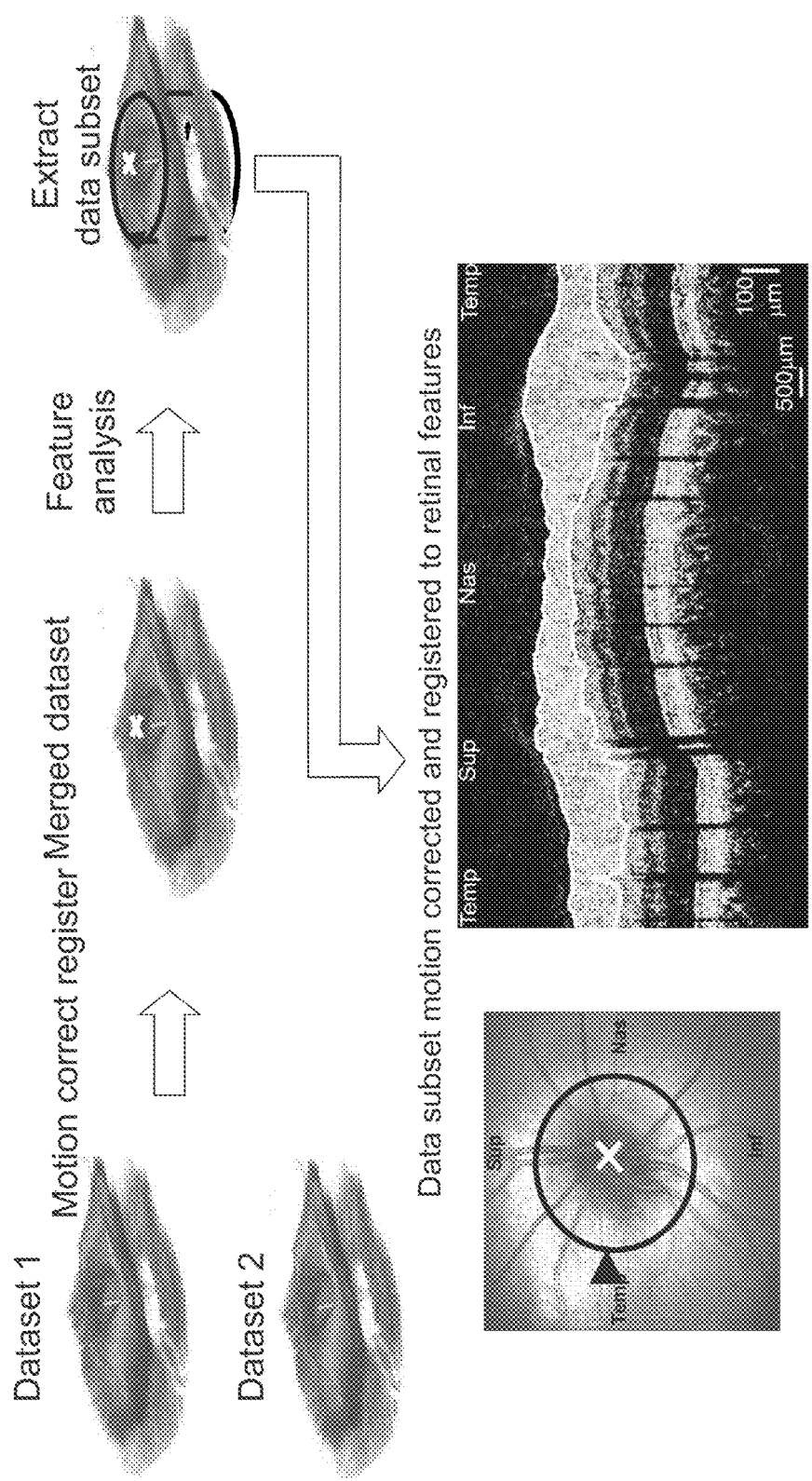
FIG. 23 is a flow chart illustrating data extraction, segmentation, and quantitative analysis according to an example embodiment of the present invention.

FIG. 23 is a flow chart illustrating the process of acquiring, motion correcting, and merging two 3D OCT data sets (Dataset 1 and Dataset 2). A feature of interest, the optic nerve head, is identified within the motion corrected and merged data set. From the position and/or orientation of the identified feature (or features), a data subset to be extracted is defined. An analysis or processing of the extracted data can be performed, including segmentation. A quantitative analysis of the data or processed data can be performed, such as nerve fiber layer thickness measurements, as shown in FIG. 23, lower right. Nerve fiber layer thickness measurement is used for the diagnosis of monitoring of glaucoma.

Since measurement variation from eye motion is currently a significant source of error for morphometric measurements such as retinal nerve fiber layer thickness, this example embodiment improves sensitivity for diagnosis of disease and tracking disease progression. Registration and merging can also be used in combination with morphometric feature assessment for other major eye diseases such as age-related macular degeneration and diabetic retinopathy. This enables the creation of datasets which represent true retinal structure without motion distortion and also enables repeated registration of datasets to retinal features. This repeated registration enables assessment of features and comparison of changes over time, such as from examination to examination.

FIG. 24A through FIG. 24C show input data (on top) and motion corrected and merged results (bottom) from three independent pairs of 3D datasets. Each pair of datasets (i.e. FIG. 24A, FIG. 24B and FIG. 24C) contains one each X fast and Y fast raster scanned dataset. The three pairs of 3D dataset were obtained in sequence and from the same eye.

Figure 25:
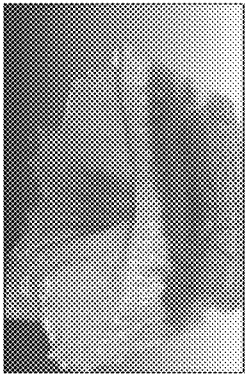
FIGS. 25A through 25F are illustrations of extracting circular cross sectional data sets from registered and merged three dimensional data sets. Panel A is a rendering of a registered and merged first three dimensional data set from FIG. 24 Panel A. Panel B is a rendering of a registered and merged second three dimensional data set from FIG. 24 Panel B. Panel C is a rendering of a registered and merged third three dimensional data set from FIG. 24 Panel C. Panel D is an OCT fundus image of the three dimensional data of Panel FIG. 25A with a circle superimposed indicating the location of where data is extracted to generate a first circular OCT cross sectional image of the tissue around the optic nerve head. Panel E is an OCT fundus image of the three dimensional data of Panel FIG. 25B with a circle superimposed indicating the location of where data is extracted to generate a second circular OCT cross sectional image of the tissue around the optic nerve head. Panel F is an OCT fundus image of the three dimensional data of Panel FIG. 25C with a circle superimposed indicating the location of where data is extracted to generate a third circular OCT cross sectional image of the tissue around the optic nerve head.
Figure 25:
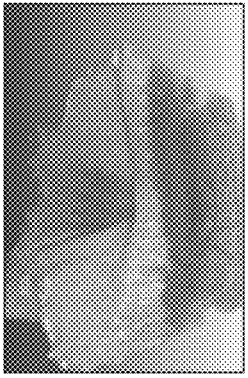
Figure 25:
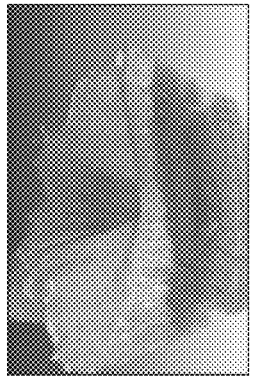
Figure 25:
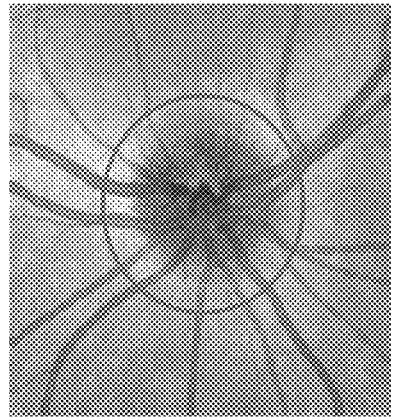
Figure 25:
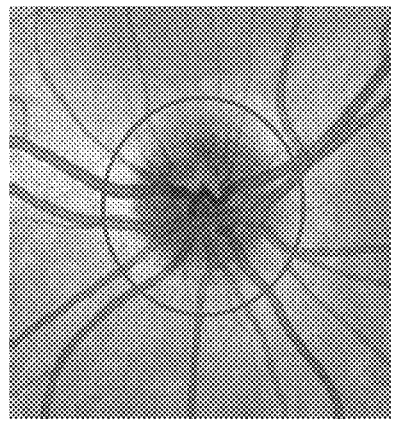
Figure 25:
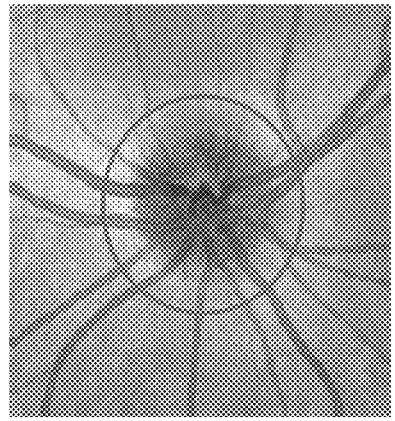

After merging, the location of the optic nerve head was identified and a circumpapillary 2D image extracted from the 3D data set, as shown in FIG. 25A through FIG. 25C. FIGS. 25A, 25B and 25C show 3D renderings of registered and merged 3D datasets originating from disjoint sets of input datasets. FIGS. 25D, 25E and 25F show the extraction of virtual circumpapillary circular scans from each of these datasets, visualized using the en face fundus projection with a circle drawn in.

Figure 26A:
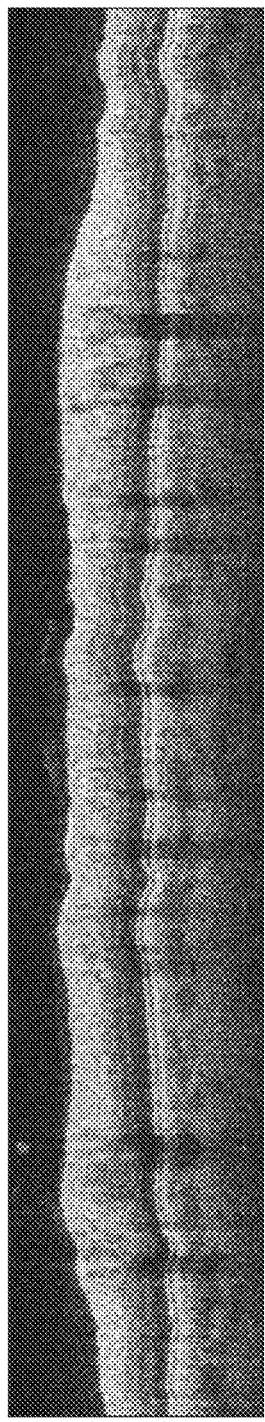
FIG. 26A is a circular OCT cross sectional image around the optic nerve head extracted from a first XFAST input dataset (FIG. 24A).
Figure 26B:
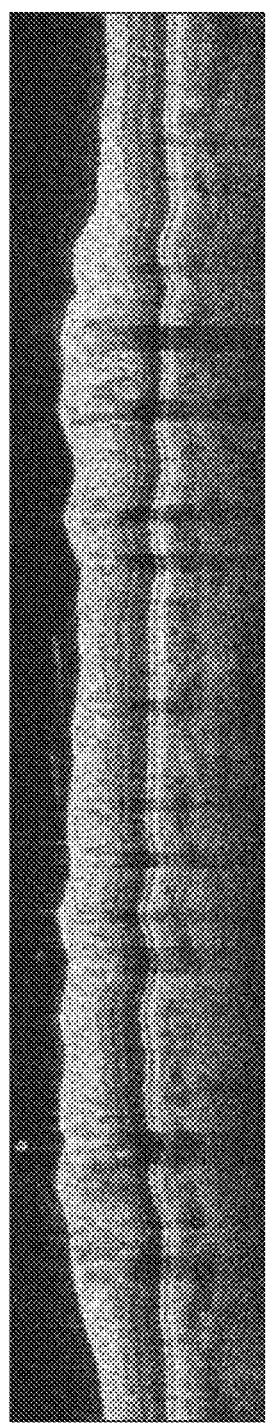
FIG. 26B is a circular OCT cross sectional image around the optic nerve head extracted from a second XFAST input dataset (FIG. 24B).
Figure 26C:
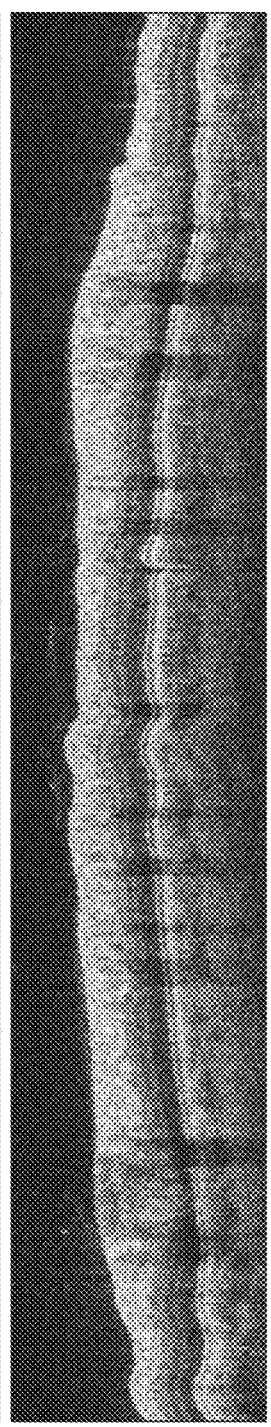
FIG. 26C is a circular OCT cross sectional image around the optic nerve head extracted from a third XFAST input dataset (FIG. 24C).
Figure 27A:
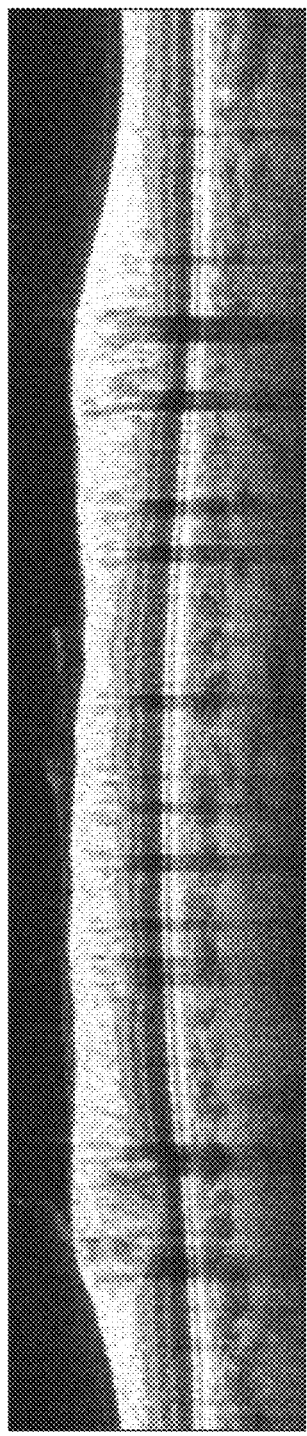
FIG. 27A is a circular OCT cross sectional image around the optic nerve head extracted from a first motion corrected and merged dataset (FIG. 25A).
Figure 27B:
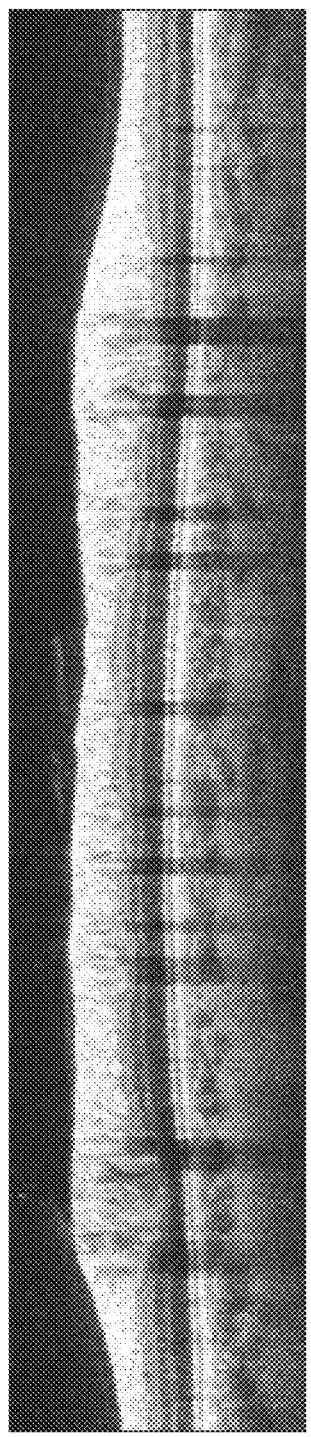
FIG. 27B is a circular OCT cross sectional image around the optic nerve head extracted from a second motion corrected and merged dataset (FIG. 25B).
Figure 27C:
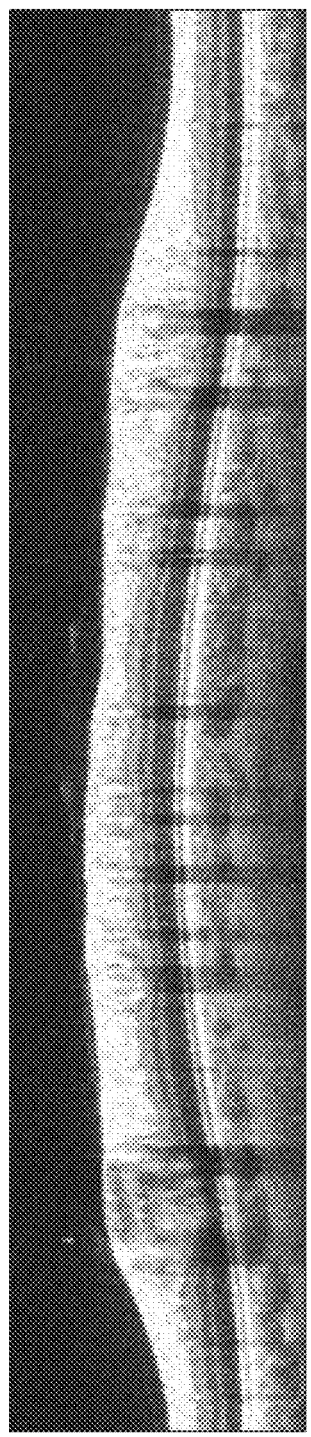
FIG. 27C is a circular OCT cross sectional image around the optic nerve head extracted from a third motion corrected and merged dataset (FIG. 25C).

2D data extracted from the associated unregistered input data sets is shown in FIG. 26A through FIG. 26C, while the same data extracted from the motion corrected and merged data is shown in FIG. 27A through FIG. 27C. FIGS. 26A, 26B and 26C show extracted virtual circumpapillary scans corresponding to the)(FAST datasets shown in FIGS. 24A, 24B and 24C. FIGS. 27A, 27B and 27C show extracted virtual circumpapillary scans corresponding to the registered and merged datasets shown in FIGS. 24A, 24B and 24C. The scans extracted from the registered and merged datasets show less variance among the three scans compared to the scans extracted from the XFAST input dataset. This indicates that reproducibility can be improved by the method.

Before motion correction and merging (FIG. 26A through FIG. 26C), there are considerable motion artifacts and gaps in the data. Note that the vertical lines drawn in the image help show the relative location of blood vessels within the image. The blood vessels are not well aligned, indicating that eye motion results in errors in the desired position of the images. After motion correction and merging (FIG. 27A through FIG. 27C), the data sets show the true retinal morphology and there is enhanced contrast and improved signal to noise. Note that the vertical lines drawn in the image help show the relative location of blood vessels. The blood vessels in the motion corrected image are well aligned, indicating the improved registration with respect to retinal structure and improved reproducibility between OCT datasets.

Example 2

The example is for the case of motion correcting and merging a pair of three dimensional OCT data sets which are acquired using orthogonal raster scan patterns. An example method for motion correction is described in mathematical detail, including the construction of the objective function, calculation of transforms and merging motion corrected 3D-OCT data sets. Examples of regularization, multi-resolution methods, preprocessing and acceleration using a graphic card are also presented.

1.1 Basic Operation

In time domain OCT a depth scan is performed by moving the mirror which reflects the reference beam. Dependent on how far away the reference arm mirror is a different portion of the depth profile of the tissue can be reconstructed using the detector. Therefore, time domain OCT involves sweeping the reference arm mirror over a certain range to generate a depth or axial scan. In Fourier or frequency domain OCT, on the other hand, a depth scan can be obtained at once by using broadband interference. A detector array and a dispersive element are used to record the spectra of the interfering waves. From these the depth scan information can be reconstructed. As the need to move the reference arm mirror is removed in the case of Fourier domain OCT scanning speed can be improved considerably. Swept source OCT systems using a swept laser have similar characteristics and operate at high speeds.

The scanning of a single axial scan or A-Scan can be modeled as a function of a position $\vec{p}=(x,y,z)^T$ and time t $$AScan(\vec{p},t): \Re^4 \mapsto \Re^{d^{(V)}} \tag{1}$$

where $d^{(V)} \in N$ is the number of values an A-Scan contains. The returned A-Scan represents a discretized version of the one dimensional profile ranging from $(x,y,z)^T$ to $(x, y, z+range_z)^T$ in coordinates relative to the scanning device. Here $range_z$ relates to the penetration depth of the OCT device and marks the range that is captured in Z direction.

The latest versions of frequency domain OCT devices can scan up to 300,000 A-Scans per second (Potsaid, B. and Gorczynska, I. and Srinivasan, V. J. and Chen, Y. and Jiang, J. and Cable, A. and Fujimoto, J. G. Ultrahigh speed spectral/Fourier domain OCT ophthalmic imaging at 70,000 to 312,500 axial scans per second. *Opt. Express*, 16:15149-15169, 2008.). This enables the dense sampling of 3D volume data from axial scans in a matter of seconds.

1.2 Volume Scanning Process

The volume can be described as an image $$V_{i,j,k}, 1 \leq i \leq w^{(V)}, 1 \leq j \leq j^{(V)}, 1 \leq k \leq d^{(V)} \tag{2}$$

where i, j and k are the discrete indices for the three spacial dimensions. $w^{(V)}$ denotes the number of samples in x, $h^{(V)}$ in y and $d^{(V)}$, as before, in z direction. The simplest method to sample a 3D volume, which is also used in this example, is to sample A-Scans on a two dimensional grid. The grid can be defined using two vectors $\vec{d} \in \Re^3$ and $\vec{d}_{slow}^{(V)} \in \Re^3$ which are orthogonal to each other.

The acquisition of the volume data then works as follows. The grid is then traversed by first taking $w^{(V)}$ A-Scans along along the so called fast axis $\vec{d}_{fast}^{(V)}$. The time taken to scan one A-Scan and position to the next A-Scan position is denoted $t_{AScan} \in \Re^+$. The two dimensional data resulting from this linear scan is called B-Scan, in reference to the fact that it is composed of A-Scans. If a B-Scan is completed the light beam is moved back to the starting position along $\vec{d}_{fast}^{(V)}$ while at the same time moving one unit along $\vec{d}_{slow}^{(V)}$ to reach the starting position for scanning the next B-Scan. This time called flyback time takes $t_{flyback} \in \Re^+$ seconds. This process is then repeated $h^{(V)}$ times until the whole grid has been sampled.

The information about the time structure of the sampling process can be compactly represented using a two dimensional image called $STIME_{i,j}^{(V)}$, which associates a time to a position (i,j) on the sampling grid. The image can be defined as $$STIME_{i,j}^{(V)}, 1 \leq i \leq w^{(V)}, 1 \leq j \leq j^{(V)} \tag{3}$$

with $$STIME_{i,j}^{(V)} = t_{start} + (i-1)t_{AScan} + (j-1)(w^{(V)}t_{AScan} + t_{flyback}) \tag{4}$$

assuming that the time of the first sample $STIME_{1,1}^{(V)}$ is $t_{start}^{(V)}$.

From this formulation the distinction between $\vec{d}_{fast}^{(V)}$ and $\vec{d}_{slow}^{(V)}$ becomes clear. Along the fast axis, $\vec{d}_{fast}^{(V)}$, which is mapped to the first index of the volume and the sample time image, neighboring samples are only $$\delta t_{fast} = t_{AScan} \tag{5}$$

apart in time. On the other hand along $\vec{d}_{slow}^{(V)}$, which becomes the second index, neighboring elements are $$\delta t_{slow} = w^{(V)} t_{AScan} + t_{flyback} \tag{6}$$

apart. This fact becomes important when taking movement between scanner and sample during acquisition into account in section 3.

The resulting volume data at the index triplet (i,j,k) can thus be generally expressed as $$V_{i,j,k}=A\text{Scan}(\vec{p}_0^{(V)}+\vec{d}_{fast}^{(V)}(i-1)+\vec{d}_{slow}^{(V)}(j-1),\text{STIME}_{i,j}^{(V)})^T\cdot\vec{e}^k \quad (7)$$

with the initial sampling position being $\vec{p}_0^{(V)}$. $\vec{e}^k$ denotes the k-th unit basis vector used here to select the k-th component of the vector produced by the AScan function.

1.3 Movement Artifacts

The typical time to scan a volume using the latest OCT technology is in the order of several seconds (Potsaid, B. and Gorczynska, I. and Srinivasan, V. J. and Chen, Y. and Jiang, J. and Cable, A. and Fujimoto, J. G. Ultrahigh speed spectral/Fourier domain OCT ophthalmic imaging at 70,000 to 312,500 axial scans per second. *Opt. Express*, 16:15149-15169, 2008.). It is assumed that the OCT device itself remains stationary during this time. However, multiple sources of motion cannot be avoided in the concrete case of scanning the retina background of a living person. The first motion component is created by the respiration of the patient. It manifests as a comparatively slow and smooth drifting movement, mainly in z direction.

On the other hand there is movement of the eye itself, either voluntary or involuntary. There are many different reasons and corresponding types of eye movement but for purposes of this example they can be divided into slow drifting movements and fast large scale movements. The large scale movements are mainly caused by so called saccades. Both of these types of movement take place as angular movements of the eye which approximately map to movement in x and y direction.

As scanning of OCT volume data does not happen at a single fixed point in time movement during acquisition presents a challenge in sampling spatially consistent data which is necessary for example in a medical context to make an accurate diagnosis.

To explain the problem of movement artifacts in detail the movement that takes place during acquisition is modeled first. For this it is assumed that the function AScan can be sampled over the the whole grid at one fixed point of time, which is arbitrarly chosen to be the point in time t=0. Naturally an imaginary volume sampled at one fixed time only would not have any motion as motion requires time to pass. One can therefore define the AScan at a certain position $\vec{p}$ and time $t \in \mathfrak{R}_0^+$ relative to the function at t=0 as $$A\text{Scan}(\vec{p},t)=A\text{Scan}(\vec{p}-\text{disp}^{(V)}(t),0) \quad (8)$$

by introducing a function $\text{disp}^{(V)}(t): \mathfrak{R} \mapsto \mathfrak{R}^3$ that models the position in space of the object to be scanned at time t relative to the object's position at the fixed point in time t=0. For example if the object would not be moving at all during acquisition the displacement would always be the same vector. If in addition the object did not move from the time t=0 to the start of the acquisition the displacement would always be the zero vector.

But since no eye tracking or similar hardware is employed the values of $\text{disp}^{(V)}$ at the sampling points are unknown. However it is assumed that $\text{disp}^{(V)}(t)$ is differenciatable and inhibits a certain smoothness. This smoothness can be expressed as $$P\nabla\text{disp}^{(V)}(t)P \leq c_{smooth}, \forall t \in \mathfrak{R}_0^+ \quad (9)$$

using a norm of the gradient $P\nabla\text{disp}^{(V)}(t)P$ of the displacement function and an unknown but fixed constant $c_{smooth}$. The smoothness assumption is reasonable when interpreting it physically: It states that the speed of the object has an upper bound. The object movement leads to a distorted volume relative to what the volume would look like if no movement took place. Specifically some areas of the object might be sampled multiple times while others will not be sampled at all. In general the voxels of the volume may not correspond to samples taken from the expected area of the object.

Also since the movement is assumed to posses a certain smoothness in time the distortion manifests differently along fast and slow axis.

When looking at raster scans the image data will generally be relatively intact when looking at slice along the fast scan direction. In the orthogonal slow direction, however in the slow direction motion artefacts are much more pronounced.

This difference can be explained by looking at the time differences between adjacent samples along the fast axis and slow axis in conjunction with the smoothness assumption of the movement. In general the value of the displacement function $\text{disp}^{(V)}(t)$ at a point in time $t_0+\delta t$ can be expressed as $$\text{disp}^{(V)}(t_0+\delta t)=\text{disp}^{(V)}(t_0)+\int_{t_0}^{t_0+\delta t}\nabla\text{disp}^{(V)}(t)dt. \quad (10)$$

By employing the smoothness assumption of equation (9) the norm of the change in displacement within the time $\delta t$ can be bounded by $$P\text{disp}^{(V)}(t_0+\delta t)-\text{disp}^{(V)}(t_0)P \leq c_{smooth}\cdot\delta t. \quad (11)$$

Because the time taken from one grid sample point to the next along the slow axis $\delta t_{slow}$ (see equation 6) is typically many times longer than the respective time along the fast axis $\delta t_{fast}$ (factor of about 500, for example) it follows from equation 11 that the change in displacement and by this the distortion is also allowed to be much higher along the slow axis.

1.4 Provided Data

The basic idea which is reflected in the provided data is to use two volumes which were sampled with orthogonal fast axis directions to correct for motion artifacts. As seen before, distortion along the fast axis is supposed to be low. In conjunction with the presence of two volumes where these fast axis and therefore the low distortion have different orientations in space this is to be used to find the distortions as represented by the displacement functions. The displacement information is then to be used to reconstruct one motion corrected volume from the two distorted versions.

The first type of volume, called XFAST is a volume that is sampled as detailed before with the fast axis direction being $$\vec{d}_{fast}^{(XFAST)} = (1, 0, 0)^T \frac{range_{xy}}{w^{(XFAST)}} \quad (12)$$

and the slow direction $$\vec{d}_{slow}^{(XFAST)} = (0, 1, 0)^T \frac{range_{xy}}{h^{(XFAST)}} \quad (13)$$

where $\vec{d}_{fast}^{(XFAST)}$, $\vec{d}_{slow}^{(XFAST)}$, $w^{(XFAST)}$ and $h^{(XFAST)}$ have their equivalents in $\vec{d}_{fast}$, $\vec{d}_{slow}$, w and h that were described in section 2. $range_{xy}$ is the range over which the scanning takes place, both in x and y direction, in world coordinates.

Similarly the two directions for the volume YFAST are $$\vec{d}_{fast}^{(YFAST)} = (1, 0, 0)^T \frac{range_{xy}}{w^{(YFAST)}} \tag{14}$$

and $$\vec{d}_{slow}^{(YFAST)} = (0, 1, 0)^T \frac{range_{xy}}{h^{(YFAST)}} \tag{15}$$

thereby being oriented so that the two volumes have orthogonal fast axis direction in space.

After providing an in depth look on the relevant parts of OCT volume scanning the following describes the methods used to solve the movement artifact correction challenge.

2. Method

This section focuses on the methods developed to solve the movement artifact reduction task. The basic concept of treating the problem as a special kind of registration problem is deduced in section 2.1 (below). The Objective Function (2.2), a multi-resolution representation of the problem (2.3), the optimization strategy (2.4) and the merging of the registration results (2.5) are treated in the subsequent sections. Finally the practical aspects of preprocessing (section 2.6, below), volume interpolation (section 2.7, below) and acceleration using OpenGL (section 2.8, below) are treated.

2.1 Deduction

As input two volumes $XFAST_{i,j,k}$ and $YFAST_{i,j,k}$ as described above are acquired. In addition the timing information of the scan process is known for both scans. This information relating a time to each sample in the scan grid is conveyed by two images $STIME_{i,j}^{(XFAST)}$ and $STIME_{i,j}^{(YFAST)}$, one for each volume (see equations (3) and (4)).

Since the same object is scanned the voxels of the two volumes can be expressed using the same function $AScan(\vec{p}, t)$ (see equation (7)) which can be reduced to the value at a fixed point in time $AScan(\vec{p}, 0)$ by employing two unknown displacement functions $disp^{(XFAST)}(t)$ and $disp^{(YFAST)}(t)$ (see equation (8)). Put differently $$XFAST_{i,j,k} = AScan\left(\vec{p}_0^{(XFAST)} + \vec{d}_{fast}^{(XFAST)}(i-1) + \vec{d}_{slow}^{(XFAST)}(j-1) - disp^{(XFAST)}(STIME_{i,j}^{(XFAST)}), 0\right)^T \cdot \vec{e}^k \tag{16}$$

and $$YFAST_{i,j,k} = AScan\left(\vec{p}_0^{(YFAST)} + \vec{d}_{fast}^{(YFAST)}(i-1) + \vec{d}_{slow}^{(YFAST)}(j-1) - disp^{(YFAST)}(STIME_{i,j}^{(YFAST)}), 0\right)^T \cdot \vec{e}^k. \tag{17}$$

By using transposition and flipping operations on the volume as well as the STIME image (see section 2.6) it is possible to change the meaning of the indices of YFAST to relate to the same basis as XFAST. The resulting volume and time functions are called YFASTR and the sampling time image is called $STIME_{i,j}^{(YFAsTR)}$ The equations then become $$XFAST_{i,j,k} = AScan\left(\vec{p}_0^{(XFAST)} + \vec{d}_{fast}^{(XFAST)}(i-1) + \vec{d}_{slow}^{(XFAST)}(j-1) - disp^{(XFAST)}(STIME_{i,j}^{(XFAST)}), 0\right)^T \cdot \vec{e}^k \tag{18}$$

and $$YFASTR_{i,j,k} = AScan\left(\vec{p}_0^{(XFAST)} + \vec{d}_{fast}^{(XFAST)}(i-1) + \vec{d}_{slow}^{(XFAST)}(j-1) - disp^{(YFAST)}(STIME_{i,j}^{(YFASTR)}), 0\right)^T \cdot \vec{e}^k. \tag{19}$$

Now it is assumed that XFAST and YFASTR are not only defined at grid points but that there are two functions $Xint(\vec{p}): \Re^3 \mapsto \Re^d$ and $Yint(\vec{p}): \Re^3 \mapsto \Re^d$ that interpolate the volume data and use the same coordinate system as the AScan function. For $$\vec{p}_{i,j} = \vec{p}_0^{(XFAST)} + \vec{d}_{fast}^{(XFAST)}(i-1) + \vec{d}_{slow}^{(XFAST)}(j-1) \tag{20}$$

the equations $$Xint(\vec{p}_{i,j}) = AScan(\vec{p}_{i,j} - disp^{(XFAST)}(STIME_{i,j}^{(XFAST)}), 0) \tag{21}$$

and $$Xint(\vec{p}_{i,j}) = AScan(\vec{p}_{i,j} - disp^{(YFAST)}(STIME_{i,j}^{(YFASTR)}), 0) \tag{22}$$

hold. By using variable substitution the displacement functions can be moved to the left side of the equations giving $$Xint(\vec{p}_{i,j} + disp^{(XFAST)}(STIME_{i,j}^{(XFAST)})) + \vec{\epsilon}_x = AScan(\vec{p}_{i,j}, 0). \tag{23}$$

and $$Yint(\vec{p}_{i,j} + disp^{(YFAST)}(STIME_{i,j}^{(YFASTR)})) + \vec{\epsilon}_y = AScan(\vec{p}_{i,j}, 0). \tag{24}$$

Since by these substitutions the functions Xint and Yint do no more necessarily sample from positions that are exactly on the original grid points of the volumes two unknown error vectors $\vec{\epsilon}_x \in \Re^d$ and $\vec{\epsilon}_y \in \Re^d$ are introduced. These error vectors model the difference between interpolating the provided volume data in contrast to what the result would be like if it was possible to sample the AScan function at that certain point. As both the right sides of these equations are equal one can examine the difference or residual vector $\vec{R}_{i,j} \in \Re^d$ at the grid point (i,j) with $$\vec{R}_{i,j} = Xint(\vec{p}_{i,j} + disp^{(XFAST)}(STIME_{i,j}^{(XFAST)})) - Yint(\vec{p}_{i,j} + disp^{(YFAST)}(STIME_{i,j}^{(YFASTR)})) + \vec{\epsilon}_x - \vec{\epsilon}_y. \tag{25}$$

If both displacement function values at the grid point (i,j) were known the values interpolated by Xint and Yint would have to be similar as they would be a noisy version of essentially the same AScan function value at the same time and position. Assuming that the two noise components $\epsilon_x$ and $\epsilon_y$ are small compared to the actual data components of Xint and Yint and tend to cancel out results in the idea that any vector length like measure of the residual would have to be minimal for the right values of the two displacement functions.

When all grid points are considered together a first version to find the displacement fields can be formulated as $$disp^{(XFAST)}, disp^{(YFAST)} = \operatorname{argmin}_{disp^{(XFAST)},disp^{(YFAST)}} \sum_i \sum_j Dist(\vec{R}_{i,j}) \quad (26)$$

with $Dist(\vec{v}): \Re^d \mapsto \Re$ being some kind of distance measure (see section 2.2).

What this formulation is still lacking is any notion of the fact that the displacement functions are supposed to be smooth in time (see equation (9)). For this a regularizing term is added to the equation that favors smooth displacement functions by penalizing high gradients of the displacement functions with respect to time. Corresponding to $\vec{R}_{i,j}$ every grid point can be associated with two gradients, one for each displacement function. These are $$\hat{G}_{i,j}{}^x = \nabla disp^{(XFAST)}(STIME^{(XFAST)}) \quad (27)$$

for the XFAST Volume and $$\hat{G}_{i,j}{}^y = \nabla disp^{(YFAST)}(STIME^{(YFASTR)}) \quad (28)$$

for YFASTR. These vectors are again fed into a distance measure $Reg(\vec{v}): \Re^3 \mapsto \Re$. Also to allow for adjustment of the relative importance between the volume distance part and the regularizer part of the equation a regularizer weighting factor $\alpha \in \Re^+$ is introduced. The optimization task then becomes $$disp^{(XFAST)}, \quad (29)$$

$$disp^{(YFAST)} = \operatorname{argmin}_{disp^{(XFAST)},disp^{(YFAST)}} \sum_i \sum_j \left( Dist(\vec{R}_{i,j}) + \alpha \left( Reg(\vec{G}_{i,j}^x) + Reg(\vec{G}_{i,j}^y) \right) \right)$$

where the continuous functions which minimize the objective function are sought.

However, for evaluating the objective function it is only necessary to have values for the displacement functions at the finite number of time steps corresponding to the grid points. Therefore a direct parameterization of the displacement fields as the values at the grid points is used in this example. The displacement field for a volume V is then $$DISP_{i,j}{}^{(V)} = disp^{(V)}(STIME_{i,j}{}^{(V)}) \quad (30)$$

with $STIME_{i,j}{}^{(V)}$ being the sample time image as defined in equation $STIME_{i,j}{}^{(V)}$, at the index pair (i,j) and $disp^{(V)}(t): \Re \mapsto \Re^3$ the original continuous displacement function. Using this parameterization the volume residual can be expressed as $$\vec{R}_{i,j} = X \operatorname{int}(\vec{p}_{i,j} + DISP_{i,j}{}^{(XFAST)}) - Y \operatorname{int}(\vec{p}_{i,j} + DISP_{i,j}{}^{(YFASTR)}) + \vec{\epsilon}_x - \vec{\epsilon}_y. \quad (31)$$

For the finite parameterization of the displacement fields the gradients of the fields along time as described in equations (27) and (28) are expressed using finite differences between the grid points. The equations become $$\vec{G}_{i,j}^x = \frac{DISP_{Nexti(i),Nextj(j)}^{(XFAST)} - DISP_{i,i}^{(XFAST)}}{STIME_{Nexti(i),Nextj(j)}^{(XFAST)} - STIME_{i,j}^{(XFAST)}} \quad (32)$$

and $$\vec{G}_{i,j}^y = \frac{DISP_{Nexti(i),Nextj(j)}^{(YFASTR)} - DISP_{i,i}^{(YFASTR)}}{STIME_{Nexti(i),Nextj(j)}^{(YFASTR)} - STIME_{i,j}^{(YFASTR)}} \quad (33)$$

where the two functions Nexti(i) and Nextj(j) provide a way to find the indices in the grid where the next sample after the sample at (i,j) is located. Such a function can easily be pre-generated, for example by sorting the time values of the sample time image and remembering the index pairs associated to the times. For completeness, both gradients are defined to be the zero vector if the current index corresponds to the last sample and therefore there is no next position defined.

Putting these changes together the optimization task becomes $$DISP^{(XFAST)}, DISP^{(YFASTR)} = \operatorname{argmin}_{DISP^{(XFAST)},DISP^{(YFASTR)}} \frac{1}{wh} \quad (34)$$

$$\sum_i \sum_j \left( Dist(\vec{R}_{i,j}) + \alpha \left( Reg(\vec{G}_{i,j}^x) + Reg(\vec{G}_{i,j}^y) \right) \right)$$

which is the formulation to be used throughout the rest of this example. Also note the new factor $$\frac{1}{wh}$$

which is added to provide a way to compare the results between versions of the objective function with different number of parameters and volume sizes which is favorable in the context of multi-resolution optimization (see section 2.3).

2.2 Objective Function

This section will focus on practical details related to the objective function and its optimization.

2.2.1 Time Modeling

First of all the time structure of the process as represented by $STIME_{i,j}{}^{(V)}$ is considered. Looking at equation (4) which is $$STIME_{i,j}{}^{(V)} = t_{start} + (i-1)t_{AScan} + (j-1)(w^{(V)}t_{AScan} + t_{flyback})$$

a scaling operation is performed on $t_{AScan}$ and $t_{flyback}$ so that the time $w^{(V)}t_{AScan}$ which is the time it takes to perform one B-Scan not including flyback, is normalized to equal 1. This way the time structure relates directly to the sampling coordinate system where the distance from one edge of the volume to the other is also one (see section 2.7). Also a factor called $fac_{flyback} \in \Re_0^+$ is introduced that provides a way to scale the relative time the flyback takes in contrast to the time for a B-Scan. The standard setting for this factor is $fac_{flyback} = 1$ so that no change with respect to the original situation is made. However changing the factor provides a way to tune the registration process, specifically the regularizer, by allowing room for more or less change in displacement between B-Scans.

2.2.2 Distance Measure

Reconsidering equation (34)

$$DISP^{(XFAST)}, DISP^{(YFASTR)} = \operatorname{argmin}_{DISP^{(XFAST)}, DISP^{(YFASTR)}} \frac{1}{wh}$$

$$\sum_i \sum_j \left( Dist(\vec{R}_{i,j}) + \alpha \left( Reg(\vec{G}^x_{i,j}) + Reg(\vec{G}^y_{i,j}) \right) \right)$$

the distance measure $Dist(\vec{R}_{i,j})$ as well as the concrete regularizing function $Reg(\vec{v})$ are still undefined.

Since the data from both volumes results from the same scanning process a case of unimodal registration is present. A commonly used distance measure in this case is the sum of squared differences or SSD measure. It is defined as $$Dist_{SSD}(\vec{R}_{i,j}) = \vec{R}_{i,j}{}^T \vec{R}_{i,j}. \tag{35}$$

The gradient of the function which is necessary for optimization is $$\nabla Dist_{SSD}(\vec{R}_{i,j}) = 2\vec{R}_{i,j} \tag{36}$$

2.2.3 Regularization

The purpose of the regularization function $Reg(\vec{v}): \Re^3 \mapsto \Re$ is to penalize high gradients of the displacement fields with respect to time, that is to produce a high output value. In addition to the general regularizer weighting factor $\alpha$ a factor $fac_{regzscale} \in \Re_0^+$ is added which allows for a distinction between movement in x/y direction and z direction. A factor of one results in the same penalization for all directions. By increasing the factor z direction movement can be penalized more, decreasing it allows for more freedom.

2.2.3.1 SSD Regularizer

The first regularization function is again using the squared length of the vector as before with the SSD distance measure. The function is $$Reg_{SSD}(\vec{v}) = \vec{v}_x^2 + \vec{v}_y^2 + fac_{regzscale} \vec{v}_z^2 \tag{37}$$

with the gradient being $$\nabla Reg_{SSD}(\vec{v}) = (2\vec{v}_x, 2\vec{v}_y, 2fac_{regzscale} \vec{v}_z)^T. \tag{38}$$

One important property of this function is that it is not a norm. Specifically the linearity under a scalar scaling factor does not hold as $$Reg_{SSD}(s\vec{v}) = s^2 Reg_{SSD}(\vec{v}) \tag{39}$$

for a factor $s \in \Re$. Because of this the function penalizes high gradients more than a norm would. This results in a tendency to produce smoother solutions as displacement fields as the regularizer favors many small increments in displacement compared to a single big increment, with the total size of the increments being the same.

2.2.3.2 L1 Regularizer

The second regularizer used in this work is based on the L1 norm which for a three-dimensional vector as is the case here is defined as $$L1(\vec{v}) = |\vec{v}_x| + |\vec{v}_z| + |\vec{v}_z|. \tag{40}$$

Unfortunately the derivative of the absolute function is not smooth and the second derivative is not even defined. Therefore using the L1 norm directly would pose serious problems for optimizing the objective function using standard gradient based techniques.

In order to circumvent this problem the L1 norm is approximated with a smooth function based on a parameter $\epsilon_{l1reg} \Re^+$. The resulting regularizer is $$Reg_{L1}(\vec{v}) = \sqrt{\vec{v}_x^2 + \epsilon_{l1reg}} + \sqrt{\vec{v}_y^2 + \epsilon_{l1reg}} + fac_{regzscale}$$
$$\sqrt{\vec{v}_z^2 + \epsilon_{l1reg}} - ((2 + fac_{regzscale}) \epsilon_{l1reg}) \tag{41}$$

with the derivative being $$\nabla Reg_{L1}(\vec{v}) = \tag{42}$$

$$\left( \frac{\vec{v}_x}{\sqrt{\vec{v}_x^2 + \epsilon_{l1reg}}}, \frac{\vec{v}_y}{\sqrt{\vec{v}_y^2 + \epsilon_{l1reg}}}, fac_{regzscale} \frac{\vec{v}_z}{\sqrt{\vec{v}_z^2 + \epsilon_{l1reg}}} \right)^T.$$

The smaller $\epsilon_{l1reg}$ the closer the regularization function is to the true L1 norm, but the harder it is to optimize as the derivative becomes less smooth. In practice $\epsilon_{l1reg}$ is chosen to be 0.05.

In contrast to the SSD regularizer this version does not (in the case of true L1) or not as strongly (in the epsilon version) penalize outliers more than linearly. The result of this is that the solution will only be smooth if the counterweight to the regularizer, namely the distance measure, favors a smooth solution. It is in this respect more data driven and can for example model discontinuities resulting from saccadic movement more easily. On the other hand the function is more non-linear and generally harder to optimize.

2.3 Multi-Resolution Representation

The optimization task as presented here is a nonlinear optimization problem. The problem is also large-scale, for example when registering two volumes with 400 times 400 A-Scans each the dimensionality of the parameter space is 400·400·2·3=960000. In general standard optimization techniques for such a problem will result in solution that is only a local minimum of the objective function (Nocedal, J. and Wright, S. J. *Numerical optimization.* Springer, 1999.). Only when the starting point of the optimization is sufficiently close to the global minimum a good solution can be reached.

One way to both improve the globality of the solution as well as improve algorithm running time is to employ a multi-resolution representation of the optimization problem as used for example in Lu, W. and Chen, M. L. and Olivera, G. H. and Ruchala, K. J. and Mackie, T. R. Fast free-form deformable registration via calculus of variations. *Physics in Medicine and Biology,* 49(14):3067-3087, 2004. Here multiple versions of the optimization problem with increasing complexity are used. Also a mapping between of the result of a lower complexity solution to a higher complexity initialization must be defined. The optimization then starts with the simplest version of the problem which is comparatively easy to optimize. The result of the simple problem is then used as an initialization for the next harder problem which is again optimized. This process is repeated until the original problem has been optimized.

The useful aspect of this technique is that a solution of the coarse problem should easily map to an initialization for the next harder problem which is already close to the global optimum for this problem. This way ultimately a good solution for the original complex optimization problem can be reached. For the optimization problem of this example a direct solution of the original problem is usually not feasible which is why multi-resolution techniques are always employed.

2.3.1 Resolution Pyramid Generation

One component of the successive simplification of the optimization problem is the reduction in the amount of data the objective function operates on. For this purpose a certain number $N_{pyramid}$ of levels of a resolution pyramid is created for both volumes. The base level with index 0 consists of the original XFAST and YFASTR volumes. Until the level $N_{pyramid}-1$ is reached the volumes for the next level are generated by down sampling the volume from the previous level by a factor of 2 in each direction. This down sampling can be performed using a simple 2×2×2 box filter.

Because of the way the original volumes were generated this uniform scaling operation is actually problematic from a sampling theoretic point of view. The box filter will average values from two adjacent B-Scans. Because of the big sample time difference between those samples and the resulting possibility for a big displacement between them these samples need not necessarily be close in space. This problem could be avoided for example by non-uniform down sampling of the volume so that the number of pixels is only reduced in direction of the fast axis. However this method would provide only a reduction in data of a factor of 4 from one level to the next compared to 8 as is the case in uniform down sampling. Because of this, the uniform version performs better in practice than the theoretically more correct non-uniform version.

2.3.2 Time Modeling

Corresponding to down sampling the volume data a coarser version of the time structure of the scanning process is provided as represented by the $STIME_{i,j}^{(XFAST)}$ and $STIME_{i,j}^{(YFASTR)}$ images. These images are generated by successively bi linearly down sampling the original sample time images. This corresponds to the way the volume data itself is scaled down when the resolution pyramid is built. Another advantage is that this method can be done without knowing how the principal type of scan protocol was (for example a collection of linear scans) and is therefore very flexible.

2.3.3 Objective Function Adaptation

To provide additional room for tuning of the registration process the association of a distinct regularizer weighting factor $\alpha_i$ to the objective function of each multi resolution level is enabled. Given the weighting factor of the coarsest level $\alpha_{N_{pyramid}-1}$ the finer factors are generated by applying a grow factor $grow_{alpha}$ so that $$\alpha_i = \alpha_{i+1} \cdot grow_{alpha}. \tag{43}$$

2.3.4 Mapping of Results Between Levels

For the coarsest level the displacement fields are initialized to be all zero in this example which lets the optimization start in the original situation as given by the two scanned volumes.

Assuming the optimization has been finished for a level with index i+1 the solution must be mapped into the higher dimensional parameter space of level i. The volume sampling coordinate system is scale invariant (see section 2.7) therefore the displacement vectors themselves which make up the solution can be directly used in the finer level without modification. The finer initialization is therefore generated by simply bi linearly re sampling the displacement image from the lower resolution to the finer one.

2.4 Optimization Strategy

This section focuses on the actual optimization that needs to be performed for each multi-resolution level and ultimately for the original objective function.

2.4.1 General

Without loss of generality optimization problem can be expressed in the form $$\vec{x}^* = \arg\min_{\vec{x}} f(\vec{x}), \vec{x} \in \mathfrak{R}^{N_{param}} \tag{44}$$

with the objective function mapped to the function $f(\vec{x})$: $\mathfrak{R}^{N_{param}} \mapsto \mathfrak{R}$ and x being the vector of variables with dimensionality $N_{param}$. This can easily be achieved by defining an ordering how to map the two displacement field images of the original objective function into the parameter vector $\vec{x}$, for example by using a lexicographic ordering. The starting position for the optimization algorithm is $x_0 \in \mathfrak{R}^{N_{param}}$.

The optimization problem for the registration can be classified as a non-linear, unconstrained and continuous optimization problem. Non-linear because the objective function value itself does not depend on the parameters in a linear fashion.

Unconstrained because possible solutions are not restricted to a certain subspace of the parameter space but instead the solution can be in all of $\mathfrak{R}^{N_{param}}$. Finally the problem is continuous because possible solutions are not restricted to for example a fixed number of integer values for the solution vector but each component of the solution can be in all of $\mathfrak{R}$. In addition at least the original optimization problem must be considered large-scale with a number of parameters $N_{param}=960000$ for the example data.

For these kinds of problems an analytic solution cannot be given, except for trivial cases, which is why optimization will be performed using iterative numerical algorithms. These algorithms are in general only able to find local extreme values of the function as they only try to fulfill the first order necessary conditions for a minimizer, that is that the gradient of the function is the zero vector. Put differently, they look for a solution $\vec{x}^*$ so that $$\nabla f(\vec{x}^*) = \vec{0}. \tag{45}$$

The optimization algorithms can be divided into two classes, depending on which basic strategy they use. The first strategy is called line search. Here the algorithm chooses a search direction $\vec{d}_{it}$ and searches along the line from the current iterate $\vec{x}_{it}$ in direction of the search direction. This search can be described as finding a step length $\alpha_{step,it}$ that approximately solves the problem $$\alpha_{step,it} = _a f(\vec{x}_{it} + a\vec{d}_{it}). \tag{46}$$

The result of iteration is then $\vec{x}_{it+1} = \vec{x}_{it} + \alpha_{step,it}\vec{d}_{it}$ which is used as the starting point for the next iteration. In this strategy a fixed direction is chosen and a step length is searched for.

In contrast, so called trust region methods make use of a model of the objective function in the neighborhood of the current value. This model is trusted up to a certain fixed distance away from the current value. The next iterate is then generated by looking for the direction which minimizes the model when looking up to the distance as defined by the trust region (Nocedal, J. and Wright, S. J. *Numerical optimization*. Springer, 1999.).

Multiple optimizers were tested regarding their suitability for the optimization problem at hand. At first a local Newton method as in Lu, W. and Chen, M. L. and Olivera, G. H. and Ruchala, K. J. and Mackie, T. R. Fast free-form deformable registration via calculus of variations. *Physics in Medicine and Biology,* 49(14):3067-3087, 2004 was tried but was found to converge too slowly. The standard line search algorithms of gradient descent and nonlinear conjugate gradients Nocedal, J. and Wright, S. J. *Numerical optimization.* Springer, 1999 performed much better but ultimately limited memory BFGS was found to be the fasted and also the most robust of the tested optimizers.

2.4.2 Limited Memory BFGS

Limited memory Broyden-Flechter-Goldfarb-Shanno or short L-BFGS is a line search based algorithm that can further be categorized as a quasi Newton algorithm. In the original BFGS algorithm, gradient information of all previous evaluations is used to construct an estimate of the Hessian matrix $\hat{H}_{it}$. Using this estimate, a search direction $\vec{d}_{it}$, is constructed by employing Newton's method as the solution of the linear system $$\vec{d}_{it} = -[H_{it}f(\vec{x}_{it})]^{-1}\nabla f(\vec{x}_{it}) \tag{47}$$

and used in the line search. For large-scale problems the storage requirements of storing all previous gradients or a dense estimate of the Hessian is prohibitive, for a 400 times 400 problem with dimensionality $N_{param}=960000$ a single gradient vector already takes up almost 8 MB of memory space.

Limited memory BFGS addresses this problem by storing only a finite small number of gradients from which the Hessian approximation is calculated. In the VNL Library implementation that is used in this example this storage parameter is set to 5. The method still retains the benefit of superlinear convergence though.

Another benefit of the method is that by construction the search direction $\vec{d}_{it}$ is well-scaled most of the time. Well-scaled means that directly using the search direction added to the current iterate without any scaling results in an iterate satisfying the Wolfe conditions for a sufficient decrease of the objective function (Nocedal, J. and Wright, S. J. *Numerical optimization.* Springer, 1999.). Because of this the line search often already succeeds without performing any search at all. This fact can tremendously reduce the number of function and gradient evaluations needed to optimize the objective function.

In practice the amount of time spent optimizing by restricting the number of function and gradient evaluations that may be performed in each level of the multi-resolution optimization is limited. The parameter that controls this amount is called MaxEvals$_{lvl}$ where lvl is the index of the multi-resolution level. Another practical aspect is that the optimization can fail because a wrong search direction was chosen or because of numerical inaccuracies. In this case the optimization is restarted as long as the budget for evaluations has not been exhausted, convergence is not reached and each restart still produces a significant improvement in objective function value.

2.5 Volume Merging 2.5.1 Basic Model

After the registration itself is finished two registration result volumes called XREG and YREG can be generated by simply applying the displacement fields of the solution to the original volume data. The resulting volume data is $$XREG_{i,j,k} = X\text{int}(\vec{p}_{i,j} + DISP_{i,j}^{(XFAST)})^T \cdot \vec{e}^k \tag{48}$$

and $$YREG_{i,j,k} = Y\text{int}(\vec{p}_{i,j} + DISP_{i,j}^{(YFASTR)})^T \cdot \vec{e}^k. \tag{49}$$

Implicitly both these volumes were already used as part of the residual used in the objective function (see equation (25)). They appear in the volume residual part of the objective function. Because of this it can be assumed that both volumes are similar if the registration itself worked.

The natural way to produce a merged volume would therefore be to simply average the volume data. However distortion can lead to the fact that some areas which are present in one volume might not be sampled at all in the other volume. If this is the case averaging is not a good approach as the data from the volume where the certain area was not present will be filled with substitute data from neighboring areas. Instead it is proposed to mainly use the data from the volume where the area was actually present for the merged volume.

This decision process is modeled by generating the data for the merged volume MERGED as a convex weighted sum of the two registration results as $$MERGED_{i,j,k} = w(i,j,k)XREG_{i,j,k} + (1-w(i,j,k))YREG_{i,j,k}))YREG_{i,j,k} \tag{50}$$

by using a weight function $w(i,j,k): N^3 \mapsto [0,1]$ that determines how to sum the two volumes for each voxel.

The basic idea to generate the weights comes from the fact that when a certain area is not present in volume A while it is present in volume B another area in the original A volume will be taken as a substitute so that this substitute area in the original volume will be sampled more than once when the registration result of A is generated. In contrast the original area from B is likely to be only sampled once.

2.5.2 Sampling Density Estimation

In order to produce weights by exploiting this fact the sampling density in the original volumes is estimated, that is how often a certain area in the original volume was sampled to produce the corresponding registration result. For this a kind of two dimensional discretized parzen window estimation with finite support is used.

An image with a size being a multiple (for example 4 times) of the x/y size of the corresponding volume is generated and initialized to a very small positive value $\epsilon_{parzen}$. The bigger size of this image is used to achieve a certain degree of subpixel accuracy, for example a factor 4 will provide 2 bits. This image represents the two dimensional area of the original volume corresponding to the two dimensional grid of A-Scans. Estimation is done by additively drawing a kernel into this image for each sample that is taken to generate the registration result.

As a kernel a two dimensional Gaussian kernel with standard a deviation $\sigma_{parzen}$ and finite half size hs$_{parzen}$ is used, with both constants corresponding to pixel sizes in the original image. The normal distribution is evaluated for every grid point of the kernel and then a scaling is done so that the sum of all values of the kernel equals one.

The drawing itself is done by centering the kernel onto the position the sample was taken and adding the kernel values to the density estimation image values. If the kernel is partly outside of the image the values are still added at the nearest edge pixel in order to mirror the behavior in the volume sampling routines itself.

2.5.3 Mapping of Density into Common Space

In order be able to relate the estimated sampling densities of the two volumes the density estimates must be brought into the common registration space. For this two images XDEST and YDEST are created. This image data at the grid point (i,j) is generated by bi linearly sampling the parzen estimation image at the position corresponding to where the data was sampled to generate the registration result in the first place.

2.5.4 Sample Validity

Another source of information that is used to generate the weights is what is called sample validity. In volume interpolation multiple voxels are taken into consideration when generating the interpolated result. Now if some or all of the voxels of this footprint are outside the actual volume data as defined by the grid of data points considered the validity of the sample to be lower than if all samples were inside. By associating a value to every voxel of the interpolation footprint which is defined to be one if the voxel is inside the grid and zero if it is outside it can be defined the validity at each grid point (i,j,k) of the registration results as the average of this value over the footprint used for interpolation. This data is contained in the volumes named XVAL and YVAL, for XREG and YREG respectively.

2.5.5 Weight Generation

Using the sampling density and validity the weights of the XREG volume at the position (i,j,k) can be generated as $$\text{weight}(i, j, k) = \frac{YDEST_{i,j,k}(1 - YVAL_{i,j,k})}{YDEST_{i,j,k}(1 - YVAL_{i,j,k}) + XDEST_{i,j,k}(1 - XVAL_{i,j,k})}. \tag{51}$$

The effect of this function is that when there is no difference in sample validity and sampling density between the two registration results the resulting weight is 0.5 which leads to an averaging of the volume data which also provides speckle noise reduction. However if the sampling density for one volume is higher, or the validity is lower the weight for the other volume will increase. This way the influence of bad samples in the merged volume is effectively reduced.

2.6 Preprocessing

In preprocessing the goal is to perform operations on the raw data that is provided by the OCT scanner in order to generate volumes that are more suitable for the registration process. As input two raw volumes called XFASTRAW and YFASTRAW are given. These two volumes are fed through a series of stages which are and will be explained in the following. The notion here is that the output of one preprocessing operation, which is a volume, is the input for the next stage. In a concrete stage the input is denoted XIN or IN corresponding to FAST YFAST respectively. If the treatment is symmetric for for both volume types the input is called VIN. The output of a stage is called XOUT YOUT or VOUT The outputs of the last stage are then the volume FAST and YFASTR as described in section 1.

Since only a part of the range covered in z direction contains interesting information each volume is cropped in axial direction. However care must be taken that the resulting axial dimension is equal for both volumes. The raw intensity data is log-transformed in order to reduce its high dynamic range. Also a min/max range conversion and thresholding is applied. For all voxels (i,j,k) of each volume the output can be defined as $$VOUT_{i,j,k} = \frac{\min\left(\max\left(\frac{(\log(VIN_{i,j,k}) - \min^{(XIN,YIN)})}{\max^{(XIN,YIN)} - \min^{(XIN,YIN)}}, \text{thresh}_{min}\right), \text{thresh}_{max}\right) - \text{thresh}_{min}}{\text{thresh}_{max} - \text{thresh}_{min}} \tag{52}$$

with $\min^{(XIN,YIN)}$ and $\max^{(XIN,YIN)}$ being the minimum and maximum of all the voxel data of both volumes after application of the log function. This way the data is moved to the range [0;1] after log conversion. Afterwards a thresholding operation using $\text{thresh}_{min}$ and $\text{thresh}_{max}$ is performed to remove intensity outliers. Finally, the data is again moved into the interval [0,1]. Note that by computing the minimum and maximum from all data exactly the same operation is performed on all values.

In order to reduce the speckle noise that is present in the raw OCT data a one dimensional median filter of size $N_{median}$ (see for example Niemann, H. Klassifikation von Mustern. Springer Verlag, Berlin, 1983) is applied to each A-Scan in the volume independently. This way any negative effects that could result from the distortion if multiple A-Scans were used can be avoided while still providing a reduction in speckle noise levels.

Another preprocessing step which can be used both for further noise reduction as well as to reduce storage and processing power requirements is the down sampling of both volumes in the axial direction. This process is optional and is performed $N_{zscaledown}$ times on both volumes. The size of the output volume remains the same, except in z direction which is halved, so $$d^{(VOUT)} = \left\lfloor \frac{d^{(VIN)}}{2} \right\rfloor, \tag{53}$$

the volume data itself can be created by simply averaging two values in z direction with a box filter.

Normalization of the data is performed by doing a so called Z-Transform on each volume, independently. The volume data is transformed so that the mean value of the resulting voxels is zero and the variance becomes 1. For this the mean $\mu^{(VIN)}$ and variance $\text{var}^{(VIN)}$ of the input volume voxel intensities are computed. The output volume data is then $$VOUT_{i,j,k} = \frac{VIN_{i,j,k} - \mu^{(VIN)}}{\sqrt{\text{var}^{(VIN)}}}. \tag{54}$$

This transform brings the volume data into a defined range and can also correct differences in general brightness between the two volumes.

Before registration it is first necessary to transform the YFAST volume and corresponding sample time image $STIME_{i,j}^{(YFAST)}$ so that the indices in x and y direction (i,j) relate to the same basis as XFAST. This can be achieved by two steps which are done with the volume data as well as the sample time image. First a transposition is done, that is the indices i and j are swapped. The second step consists of flipping the data in y direction.

2.7 Volume Interpolation

One useful part of a working registration algorithm is the implementation of the volume interpolation functions $\text{Xint}(\vec{p})$ and $\text{Yint}(\vec{p})$ which are supposed to interpolate the volume data of the XFAST and YFASTR volumes, respectively (see equations (21), (22)). The way of interpolation is the same for both volumes so it is assumed that a volume called is to be interpolated with the function $$\text{Vint}(\vec{p}_{int}): \mathfrak{R}^3 \mapsto \mathfrak{R}^{d_{int}^{(V)}} \tag{55}$$

where $\vec{p}_{int}=(x_{int},y_{int},z_{int})^T \in \Re^3$ is a vector in a special interpolation coordinate system. $d_{int}^{(V)}$ is the dimensionality of the returned vector. Note that the interpolation function does not just sample the volume at one place but instead will sample at $d_{int}^{(V)}$ different locations in z direction to generate the interpolated equivalent of an A-Scan. The interpolation done by Vint($\vec{p}_{int}$) can therefore be decomposed into multiple operations that interpolate the volume data along a line in z direction. This process can be described by introducing a function which Vsample($\vec{p}_{sample}$): $\Re^3 \mapsto \Re$ which interpolates the volume data a the location $\vec{p}_{sample}$, producing a single intensity value. Using this notion the i-th component of the result vector from Vint($\vec{p}_{int}$), can be defined to be $$Vint(\vec{p}_{int})^T \cdot \vec{e}^i = VSample(\vec{p}_{start,sample}+(i-1) \vec{p}_{inc,sample}) \quad (56)$$

by employing a to be defined start vector $\vec{p}_{start,sample}$ in the sampling coordinate system, and a sampling increment vector $\vec{p}_{inc,sample}$ that defines the increment in z direction from one component of the result vector to the next.

2.7.1 Sampling Coordinate System

The coordinate system used for interpolating the volume data is not the world coordinate system, based on physical units, as used before. Instead a scale invariant system is preferred where the volume data lies in the [0,1] unit cube. One such coordinate system is the OpenGL coordinate system (Segal, M. and Akeley, K. The OpenGL graphics system: A specification (version 2.0). *Silicon Graphics*, Mountain View, Calif., 2004.). It was chosen here because it is widely used, well defined and also because in the concrete program implementation OpenGL is used to accelerate the volume interpolation process. The scale invariance also has benefits for the multi-resolution approach (see section 2.3).

In the OpenGL coordinate system the coordinates of the center of the voxel $V_{i,j,k}$ at the indices (i,j,k) are $$pcenter_{i,j,k} = \left(\frac{0.5+(i-1)}{w^{(v)}}, \frac{0.5+(j-1)}{h^{(v)}}, \frac{0.5+(k-1)}{d^{(v)}}\right)^T. \quad (57)$$

If one of the components of the result vector of the interpolation function comes from sampling at such a voxel center the result should be exactly the intensity data of the original discrete volume at the indices (i,j,k). Put differently $$VSample(pcenter_{i,j,k})=V_{i,j,k} \quad (58)$$

should be satisfied by any concrete interpolation function VSample

By looking at equation (57) it can be seen that the increment vector $\vec{p}_{inc,sample}$ from equation (56) for moving exactly one pixel in z direction should be $$\vec{p}_{inc,sample} = \left(0, 0, \frac{1}{d^{(v)}}\right)^T. \quad (59)$$

For solving the optimization problem it is necessary that the interpolation function is defined in all of $\Re^3$, not just in the [0,1] unit cube. If a sample point $\vec{p}_{sample} \in \Re^3$ lies outside the unit cube in any coordinate the result is as if the sample location would be moved inside the unit cube in that particular direction to lie directly on the pixel center that is nearest to the edge of the unit cube in this direction. In OpenGL this behaviour when sampling textures is associated with the GL_CLAMP_TO_EDGE identifier.

Normally, since the interpolation function should generate A-Scan equivalents, one would assume that the dimensionality of the interpolated vector $d_{int}^{(V)}$ should equal $d^{(V)}$. However it is possible by symmetrically cropping the resulting vector at the start and end positions, corresponding to minimal and maximal z coordinates of the samples, to reduce computational effort as well as effects that result from sampling outside of the unit cube. By introducing a factor called $frac_{border} \in [0; 0.5]$ which specifies the fraction of the original dimensionality of the interpolated vector to remove at both sides the resulting vector size becomes $$d_{int}^{(V)}=d^{(V)}-2\lfloor d^{(V)}frac_{border} \rfloor. \quad (60)$$

Also the start sampling position from equation (56) is generated from the input of the outer sampling function $\vec{p}_{int}$ and the sampling border information as $$\vec{p}_{start,sample} = \vec{p}_{int} + \left(0, 0, \frac{0.5+\lfloor d^{(v)}frac_{border} \rfloor}{d^{(v)}}\right)^T \quad (61)$$

which means that the first sample is moved $\lfloor d^{(V)}frac_{border} \rfloor$ samples towards positive z. In practice a typical setting is to remove 5 percent of the samples at both ends, so that $frac_{border}=0.05$.

2.7.2 Interpolation Methods

As concrete interpolation methods trilinear as well as cubic spline interpolation were implemented. Trilinear interpolation is widely used for volume interpolation purposes. This can be attributed to the relative speed, simplicity and robustness of the method. In linear interpolation, which is the one dimensional basis of the trilinear variant, interpolation is done by connecting a straight line between two data points. This interpolation method has the benefit that the interpolated value is guaranteed to be within the range that is given by the two data points.

Trilinear interpolation is the extension of linear interpolation to three dimensions. It can be performed by doing multiple one dimensional interpolations in the cube defined by the eight nearest samples to the interpolation point. In the concrete sampling pattern of interpolating axial scan equivalents this process can be optimized by first doing two dimensional interpolations in x/y direction for all values along the z direction. The resulting line of values can then be interpolated linearly according to the fractional coordinate in z direction. This way the amortized number of voxel values that need to be processed is reduced from eight to four.

In order to be able to optimize the objective function partial derivatives of the volume interpolation functions must be provided. Unfortunately, the trilinear interpolation scheme does not provide continuous derivatives as the derivative which is the slope of the line segments can snap from one value to another at pixel centers. Because of this derivatives are approximated by using a finite difference scheme. In order to capture more information about the function a central difference scheme is preferred to a forward difference scheme. Using a constant $\epsilon_{centraldiff}$ the partial derivatives at a sample point $\hat{p}_{sample}$ can be approximated as $$\frac{\delta VSample(\vec{p}_{sample})}{\delta \vec{e}^{dim}} \approx \frac{VSample\left(\vec{p}_{sample} + \varepsilon_{centraldiff}\vec{e}^{dim}\right) - VSample\left(\vec{p}_{sample} - \varepsilon_{centraldiff}\vec{e}^{dim}\right)}{2\varepsilon_{centraldiff}} \qquad (62)$$

where $\vec{e}^{dim}$ denotes the unit basis vector for the dimension denoted with index dim. $\varepsilon_{centraldiff}$ would ideally be chosen to be as small as possible as this would provide the best approximation. However numerical precision issues that result from choosing the constant too small must be considered. In practice the epsilon is chosen to equal 0.01 the distance from one pixel center to the next.

Because of the problems of linear interpolation related to derivatives a second interpolation scheme using cubic Hermite splines was implemented. This method provides a way to analytically compute smooth derivatives. Again the method can be explained by looking at the one dimensional case. For a cubic spline the support, that is the number of pixels that are taking into consideration when interpolation is four, compared to two for the linear case.

One disadvantage of this interpolation method is that in contrast to linear interpolation an interpolated value can be outside of the range of values as given by the data points. These so called overshoot effects can be produced when high frequency content is present in the data which is for example the case with speckle noise. Therefore spline interpolation is in this example only used in conjunction with noise reduction methods.

2.8 Acceleration Using Graphics Hardware

One useful aspect for practical usability of the motion artifact correction algorithm is execution speed. For the optimization which is the main part of the algorithm the objective function and its gradient must be evaluated repeatedly. Especially for the original complexity level this requires a lot of computation, mainly for interpolating the two OCT volumes. When looking at the objective function itself it can be seen that it is composed of a sum of independent expressions.

Advantage is taken of this potential for parallelization by moving the volume interpolation and residual computation including gradients to the graphics card while keeping the regularizer part on the CPU side for flexibility reasons. Both trilinear as well as cubic spline interpolation is supported. The implementation uses OpenGL in conjunction with the OpenGL Shading Language. This way the code is both vendor as well as operating system independent. Comparing the speed of the accelerated version using an ATI Radeon 4850 with the standard version on an Intel Core 2 Duo with 2.16 Ghz a speedup of the optimization process of a factor of about 60 is gained. This dramatically lowers the time needed for the whole algorithm and therefore increases the feasibility for practical clinical use.

It should be understood that certain embodiments or portions thereof may be implemented in hardware, firmware, or software. If implemented in software, the software may be any language that can cause a processor to be configured in a manner to perform embodiments discussed herein or equivalents thereof. The software may be in the form of executable instructions and stored on any non-transient, computer-readable medium that can be loaded and executed by a general purpose or application-specific processor.

While the methods and devices described herein have been particularly shown and described with references to example embodiments thereof, it will be understood by those skilled in the art that various changes in form and details may be made therein.

What is claimed is:

1. A non-transitory computer-readable medium having thereon a sequence of instructions, which, when executed by a processor:
   cause an optical coherence tomography (OCT) imaging device to acquire at least a first three-dimensional data set and a second three-dimensional data set representing overlapping regions of an object with the OCT imaging instrument;
   optionally, cause the processor to compute at least one of a first derivative three-dimensional data set corresponding to the first three-dimensional data set, a second derivative three-dimensional data set corresponding to the second three-dimensional data set, a first preprocessed three-dimensional data set corresponding to the first three-dimensional dataset, or a second preprocessed three-dimensional data set corresponding to the second three-dimensional dataset;
   for at least the first and the second three-dimensional data sets, cause the processor to compute a first three-dimensional transform and a second three-dimensional transform respectively;
   cause the processor to apply the first three-dimensional transform to one of: the first three-dimensional data set, the first derivative three-dimensional data set, or the first preprocessed three-dimensional data set, thereby producing a first three-dimensional data set in the transformed state;
   cause the processor to apply the second three-dimensional transform to one of: the second three-dimensional data set, the second derivative three-dimensional data set, or the second preprocessed three dimensional data set, thereby producing a second three-dimensional data set in the transformed state
   cause the processor to evaluate an objective function by calculating similarity between the first three-dimensional data set in the transformed state and the second three-dimensional data set in the transformed state and estimate motion of the object relative to the OCT imaging instrument; and
   cause the processor to apply at least one three-dimensional transform to at least one of the first or the second three-dimensional data sets, the first or the second derivative three-dimensional data sets, or the first or the second preprocessed three-dimensional data sets to obtain at least one motion-corrected data set representing the object.

2. The computer-readable medium of claim 1, wherein the sequence of instructions causes the processor to evaluate the objective function by favoring similarity between the first and the second three-dimensional data sets in the transformed state.

3. The computer-readable medium of claim 2, wherein each three-dimensional data set is a set of values of a signal acquired from a region of the object, and wherein favoring similarity between the first and the second three-dimensional data sets in the transformed state includes penalizing differences among signal values of the first and the second three-dimensional data sets in the transformed state.

4. The computer-readable medium of claim 1, wherein the sequence of instructions causes the processor to evaluate the objective function by penalizing motion of the object relative to the imaging instrument.

5. The computer-readable medium of claim 1, wherein the sequence of instructions causes the processor
to apply at least one three-dimensional transform by applying the first three-dimensional transform to the first three-dimensional data set, the first derivative three-dimensional data set, or the first preproccessed three-dimensional data set and by applying the second three-dimensional transform to the second three-dimensional data set, the second derivative three-dimensional data set, or the second preprocessed three-dimensional data set to obtain first and second motion-corrected data sets, respectively, and
to combine data elements of the first and second motion-corrected data sets to obtain a merged motion-corrected data set having improved signal quality relative to the first or second motion-corrected data sets, individually.

6. The computer-readable medium of claim 5, wherein the sequence of instructions causes the processor to combine data elements by adjusting contributions of data elements of the first and second motion-corrected data sets to the merged motion-corrected data set based on at least one property of the first and the second three-dimensional transforms.

7. The computer-readable medium of claim 6, wherein the at least one property of the first or the second three-dimensional transform is sampling density.

8. The computer-readable medium of claim 6, wherein said adjusting further includes computing a weighted sum of the data elements of the first and second motion-corrected data sets.

9. The computer-readable medium of claim 1, wherein the first three-dimensional data set is acquired using a first scan pattern and the second three-dimensional data set is acquired using a second scan pattern, wherein the first and the second scan patterns are complementary.

10. The computer-readable medium of claim 9, wherein the complementary scan patterns are raster scans.

11. The computer-readable medium of claim 10, wherein the raster scans are orthogonal.

12. The computer-readable medium of claim 1, wherein the sequence of instructions causes the processor to iteratively compute the first three-dimensional transform and the second three-dimensional transform.

13. The computer-readable medium of claim 1, wherein the sequence of instructions causes the processor to compute the first three-dimensional transform and the second three-dimensional transform using a numerical optimization method.

14. The computer-readable medium of claim 1, wherein the sequence of instructions causes the processor to compute the first three-dimensional transform and the second three-dimensional transform using a multi-resolution numerical optimization method.

15. The computer-readable medium of claim 1, wherein the object is selected from the group consisting of the eye, retina, fovea, optic nerve head, or cornea.

16. The computer-readable medium of claim 1, wherein the sequence of instructions causes the processor to:
obtain a first motion-corrected data set representing the object at a first time point,
obtain a second motion-corrected data set representing the object at a second time point, and
compare the first and the second motion-corrected data sets to quantitatively track changes in the object between the first and the second time points.

17. The computer-readable medium of claim 5, wherein the sequence of instructions causes the processor to:
obtain a first merged motion-corrected data set representing the object at a first time point,
obtain a second merged motion-corrected data set representing the object at a second time point, and
compare the first and the second merged motion-corrected data sets to quantitatively track changes in the object between the first and the second time points.

18. The computer-readable medium of claim 16, wherein the object is associated with a patient.

19. The computer-readable medium of claim 18, wherein the first and the second time points correspond to the first and the second visits by the patient to a healthcare provider, respectively.

20. The computer-readable medium of claim 18, wherein the first and the second time points correspond to the first and the second activities by the patient for scanning the object, respectively.

21. The computer-readable medium of claim 1, wherein the sequence of instructions causes the processor to capture the three-dimensional data set via A-scans and to associate three-dimensional displacements with A-scans, thereby forming representations of the two or more three-dimensional transforms.

22. The computer-readable medium of claim 1, wherein the sequence of instructions causes the processor to compute the first preprocessed three-dimensional data set or the second preprocessed data set or both by at least one method selected from the group consisting of: image resampling, noise reduction, A-scan feature generation, tilt-compensation, and roll-off compensation.

23. The computer-readable medium of claim 1, wherein the sequence of instructions causes the processor to acquire at least one three-dimensional data set that includes at least one of intensity data, Doppler shift data, or polarization data.

24. The computer-readable medium of claim 1, wherein the sequence of instructions causes the processor to compute at least one derivative three-dimensional data set that includes at least one of Doppler shift data or polarization data.

25. A computer-implemented method of correcting a data set representing an object for the object's motion relative to an optical coherence tomography (OCT) imaging instrument, comprising:
acquiring at least a first three-dimensional data set and a second three-dimensional data set representing overlapping regions of an object with the OCT imaging instrument;
optionally, computing at least one of a first derivative three-dimensional data set corresponding to the first three-dimensional data set, a second derivative three-dimensional data set corresponding to the second three-dimensional data set, a first preprocessed three-dimensional data set corresponding to the first three-dimensional dataset, or a second preprocessed three-dimensional data set corresponding to the second three-dimensional dataset,
for at least the first and the second three-dimensional data sets, computing a first three-dimensional transform and a second three-dimensional transform respectively;
applying the first three-dimensional transform to one of: the first three-dimensional data set, the first derivative three-dimensional data set, or the first preprocessed three dimensional data set, thereby producing a first three-dimensional data set in the transformed state;
applying the second three-dimensional transform to one of: the second three-dimensional data set, the second derivative three-dimensional data set, or the second preprocessed three dimensional data set, thereby producing a second three-dimensional data set in the transformed state;

evaluating an objective function by calculating similarity between the first three-dimensional data set in the transformed state and the second three-dimensional data set in the transformed state and estimating motion of the object relative to the OCT imaging instrument; and applying at least one three-dimensional transform to at least one of the first or the second three-dimensional data sets, the first or the second derivative three-dimensional data sets, or the first or the second preprocessed three-dimensional data sets to obtain at least one motion-corrected data set representing the object, further comprising:

computing the first three-dimensional transform and the second three-dimensional transform using a numerical optimization method; and initializing the first three-dimensional transform and the second three-dimensional transform with information from an additional data source, wherein the additional data source provides a rough estimate of the relative motion between the object and the optical coherence tomography imaging instrument.

26. The method of claim 25, wherein the additional data source comprises a fundus camera.

27. An optical coherence tomography (OCT) system correcting a data set representing an object for the object's motion relative to an OCT imaging instrument, comprising:
a memory configured to store at least one three-dimensional data set;
an acquisition module comprising an OCT imaging instrument, the acquisition module configured to acquire at least a first three-dimensional data set and a second three-dimensional data set representing overlapping regions of an object;
a computing module configured to:
(i) optionally, compute at least one of a first derivative three-dimensional data set corresponding to the first three-dimensional data set, a second derivative three-dimensional data set corresponding to the second three-dimensional data set, a first preprocessed three-dimensional data set corresponding to the first three-dimensional dataset, or a second preprocessed three-dimensional data set corresponding to the second three-dimensional dataset;
(ii) for at least the first and the second three-dimensional data sets, compute a first three-dimensional transform and a second three-dimensional transform respectively;
(iii) apply the first three-dimensional transform to one of: the first three-dimensional data set, the first derivative three-dimensional data set, or the first preprocessed three dimensional data set, thereby producing a first three-dimensional data set in the transformed state;
(iv) apply the second three-dimensional transform to one of: the second three-dimensional data set, the second derivative three-dimensional data set, or the second preprocessed three dimensional data set, thereby producing a second three-dimensional data set in the transformed state;
(v) evaluate an objective function by calculating similarity between the first three-dimensional data set in the transformed state and the second three-dimensional data set in the transformed state and estimate motion of the object relative to the OCT imaging instrument; and
a motion-correction module configured to apply at least one three-dimensional transform to at least one of the first or the second three-dimensional data sets, the first or the second derivative three-dimensional data sets, or the first or the second preprocessed three-dimensional data set to obtain at least one motion-corrected data set representing the object,
wherein the computing module is configured to compute the first three-dimensional transform and the second three-dimensional transform using a numerical optimization method,
the system further comprising an additional data source, wherein the computing module is configured to initialize the first three-dimensional transform and the second three-dimensional transform with information from the additional data source, wherein the additional data source provides a rough estimate of the relative motion between the object and the optical coherence tomography imaging instrument.

28. The system of claim 27, wherein the additional data source comprises a fundus camera.

* * * * *